United States Patent
Akino et al.

(10) Patent No.: US 9,735,374 B2
(45) Date of Patent: Aug. 15, 2017

(54) METAL COMPLEX AND LIGHT-EMITTING DEVICE CONTAINING THE METAL COMPLEX

(71) Applicants: Sumitomo Chemical Company, Limited, Tokyo (JP); National Institute of Advanced Industrial Science and Technology, Tokyo (JP)

(72) Inventors: Nobuhiko Akino, Ibaraki (JP); Taichi Abe, Ibaraki (JP); Hideo Konno, Ibaraki (JP); Shigeru Shimada, Ibaraki (JP); Kazuhiko Sato, Ibaraki (JP)

(73) Assignees: SUMITOMO CHEMICAL COMPANY, LIMITED, Tokyo (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 336 days.

(21) Appl. No.: 14/371,844

(22) PCT Filed: Jan. 10, 2013

(86) PCT No.: PCT/JP2013/050267
§ 371 (c)(1),
(2) Date: Jul. 11, 2014

(87) PCT Pub. No.: WO2013/108699
PCT Pub. Date: Jul. 25, 2013

(65) Prior Publication Data
US 2015/0014669 A1    Jan. 15, 2015

(30) Foreign Application Priority Data

Jan. 18, 2012 (JP) ................................ 2012-008118

(51) Int. Cl.
*H01L 51/54* (2006.01)
*C09K 11/06* (2006.01)
(Continued)

(52) U.S. Cl.
CPC ...... *H01L 51/0085* (2013.01); *C07F 15/0033* (2013.01); *C08K 5/0091* (2013.01);
(Continued)

(58) Field of Classification Search
None
See application file for complete search history.

(56) References Cited

U.S. PATENT DOCUMENTS 7,659,010 B2   2/2010 Burn et al.
8,216,699 B2   7/2012 Burn et al.
(Continued)

FOREIGN PATENT DOCUMENTS

EP   1 325 671 B1   10/2012
JP   2007-123392 A   5/2007
(Continued)

OTHER PUBLICATIONS

Int'l Search Report issued Mar. 26, 2013 in Int'l Application No. PCT/JP2013/050267.
(Continued)

*Primary Examiner* — Marie R. Yamnitzky
(74) *Attorney, Agent, or Firm* — Panitch Schwarze Belisario & Nadel LLP

(57) ABSTRACT

A metal complex exhibits blue light emission of high color purity and has a color purity of small temperature dependence, particularly in the blue region. Specifically, the metal complex is represented by Formula (1a):

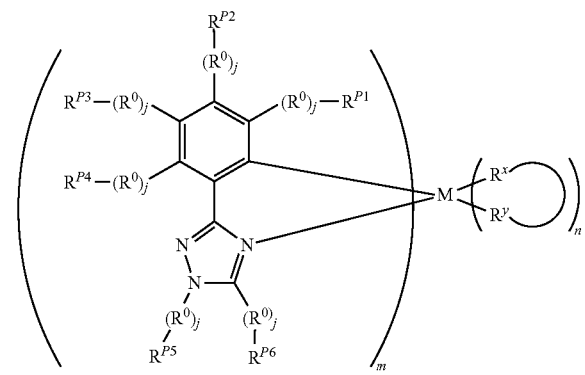

(1a)

wherein M is a metal atom; $R^0$ is a divalent linking group; each j independently represents 0 or 1; $R^{P1}$, $R^{P2}$, $R^{P3}$, $R^{P4}$ and $R^{P6}$ each independently represents a hydrogen atom or the like; $R^{P5}$ represents a halogen atom or the like; m is an integer of from 1 to 3, n is an integer of from 0 to 2, and m+n is 2 or 3; and the portion represented by Formula (2):

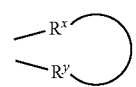

(2)

represents a bidentate ligand; wherein $R^x$ and $R^y$ are an atom bonding to the metal atom M, and each independently represents a carbon atom, an oxygen atom or a nitrogen atom.

23 Claims, No Drawings

(51) Int. Cl.
  *H01L 51/00* (2006.01)
  *C07F 15/00* (2006.01)
  *C08K 5/00* (2006.01)
  *H05B 33/10* (2006.01)
  *H01L 51/50* (2006.01)

(52) U.S. Cl.
  CPC .............. *C09K 11/06* (2013.01); *H05B 33/10* (2013.01); *C09K 2211/1007* (2013.01); *C09K 2211/1011* (2013.01); *C09K 2211/1059* (2013.01); *C09K 2211/185* (2013.01); *H01L 51/5012* (2013.01); *H01L 51/5016* (2013.01)

(56) References Cited

U.S. PATENT DOCUMENTS

| | | | |
|---|---|---|---|
| 9,406,894 B2 * | 8/2016 | Inoue et al. | ........ H01L 51/0067 |
| 2006/0000867 A1 | 1/2006 | Shelton et al. | |
| 2006/0008670 A1 | 1/2006 | Lin et al. | |
| 2009/0102370 A1 * | 4/2009 | Taka et al. | ........... C07D 233/58 313/504 |
| 2009/0239000 A1 | 9/2009 | Sugita et al. | |
| 2012/0305896 A1 | 12/2012 | Inoue et al. | |

FOREIGN PATENT DOCUMENTS

| | | |
|---|---|---|
| JP | 2008-084913 A | 4/2008 |
| JP | 2009-096861 A | 5/2009 |
| JP | 2011-253980 A | 12/2011 |
| JP | 2013-010752 A | 1/2013 |
| JP | 2013147551 A | 8/2013 |
| WO | 0215645 A1 | 2/2002 |
| WO | 2004101707 A1 | 11/2004 |
| WO | 2007052431 A1 | 5/2007 |
| WO | 2013191086 A1 | 12/2013 |
| WO | 2013191088 A1 | 12/2013 |

OTHER PUBLICATIONS

Office Action issued Dec. 8, 2015 in JP Application No. 2012008118.

* cited by examiner

METAL COMPLEX AND LIGHT-EMITTING DEVICE CONTAINING THE METAL COMPLEX

CROSS-REFERENCE TO RELATED APPLICATION

This application is a Section 371 of International Application No. PCT/JP2013/050267, filed Jan. 10, 2013, which was published in the Japanese language on Jul. 25, 2013, under International Publication No. WO 2013/108699 A1, and the disclosure of which is incorporated herein by reference.

TECHNICAL FIELD

The present invention relates to a metal complex and a light-emitting device containing the metal complex.

BACKGROUND ART

For light-emitting materials used for a light-emitting layer of an organic electroluminescent device (hereinafter may be referred to as a "light-emitting device"), metal complexes exhibiting light emission from a triplet excited state can be expected to have a higher luminous efficiency than fluorescent materials exhibiting light emission from a singlet excited state. As a blue light-emitting metal complex exhibiting light emission from a triplet excited state (phosphorescent light emission), there are known, for example, FIrpic which is a metal complex having an iridium atom as a metal atom (Patent Document 1) and a metal complex having a triazole ring-containing ligand (Patent Document 2).

RELATED ART DOCUMENT

Patent Document

Patent Document 1: WO 2002/15645
Patent Document 2: WO 2004/101707

SUMMARY OF THE INVENTION

Problem to be Solved by the Invention

For practical use of an organic electroluminescent device or the like using metal complexes, it is desired to develop a metal complex which is useful for the manufacture of a light-emitting device having an excellent luminous efficiency and an excellent lifetime property in three primary colors of red, green and blue. It is desired to develop a metal complex exhibiting blue light emission of high color purity and having a color purity of small temperature dependence, particularly in a blue region in comparison with red and green. Hence, an object of the present invention is to provide a metal complex exhibiting blue light emission of high color purity and having a color purity of small temperature dependence, particularly in a blue region. It is also an object of the present invention is to provide a light-emitting device using the metal complex.

Means for Solving Problem

Firstly, the present invention provides a metal complex represented by Formula (1a):

[Chem. 1]

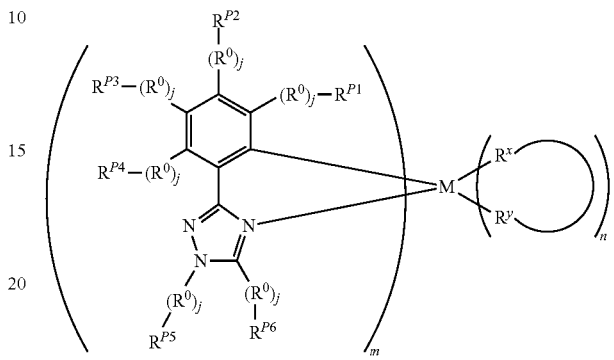

(1a)

wherein

M is a metal atom selected from the group consisting of a ruthenium atom, a rhodium atom, a palladium atom, an osmium atom, an iridium atom and a platinum atom;

each $R^0$ is independently a divalent linking group selected from the group consisting of a group represented by Formula (L-1), a group represented by Formula (L-2) and a group represented by Formula (L-3):

[Chem. 2]

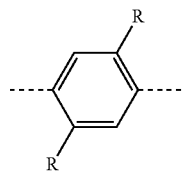

(L-1)

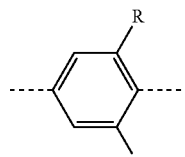

(L-2)

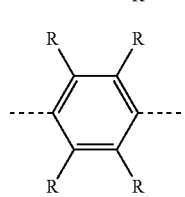

(L-3)

wherein each R independently represents an alkyl group; each j independently represents 0 or 1;

$R^{P1}$, $R^{P2}$, $R^{P3}$, $R^{P4}$ and $R^{P6}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group;

$R^{P5}$ represents a halogen atom, an alkyl group, an alkyloxy group, an aryl group or a monovalent heterocyclic group;

$R^{P1}$ and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure;

m is an integer of from 1 to 3, n is an integer of from 0 to 2, and m+n is 2 or 3; and the portion represented by Formula (2):

[Chem. 3]

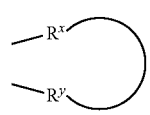

(2)

represents a bidentate ligand;

wherein $R^x$ and $R^y$ are an atom bonding to the metal atom M, and each independently represent a carbon atom, an oxygen atom or a nitrogen atom.

Secondly, the present invention provides a metal complex represented by Formula (1b):

[Chem. 4]

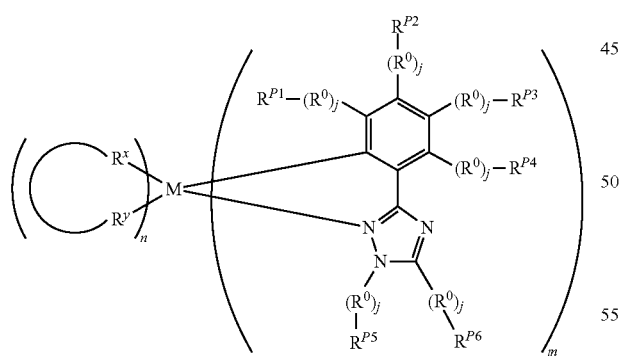

(1b)

wherein

M is a metal atom selected from the group consisting of a ruthenium atom, a rhodium atom, a palladium atom, an osmium atom, an iridium atom and a platinum atom;

each $R^0$ is independently a divalent linking group selected from the group consisting of a group represented by Formula (L-1), a group represented by Formula (L-2) and a group represented by Formula (L-3):

[Chem. 5]

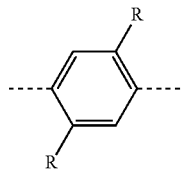

(L-1)

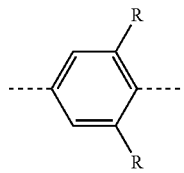

(L-2)

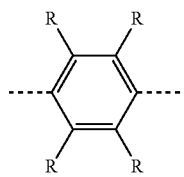

(L-3)

wherein each R independently represents an alkyl group;

each j independently represents 0 or 1;

$R^{P1}$, $R^{P2}$, $R^{P3}$, $R^{P4}$ and $R^{P6}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group;

$R^{P5}$ represents a halogen atom, an alkyl group, an alkyloxy group, an aryl group or a monovalent heterocyclic group;

$R^{P1}$ and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure;

m is an integer of from 1 to 3, n is an integer of from 0 to 2, and m+n is 2 or 3; and the portion represented by Formula (2):

[Chem. 6]

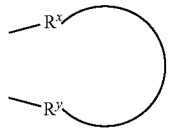

represents a bidentate ligand;

wherein $R^x$ and $R^y$ are an atom bonding to the metal atom M, and each independently represent a carbon atom, an oxygen atom or a nitrogen atom.

Thirdly, the present invention provides a metal complex represented by Formula (1c):

[Chem. 7]

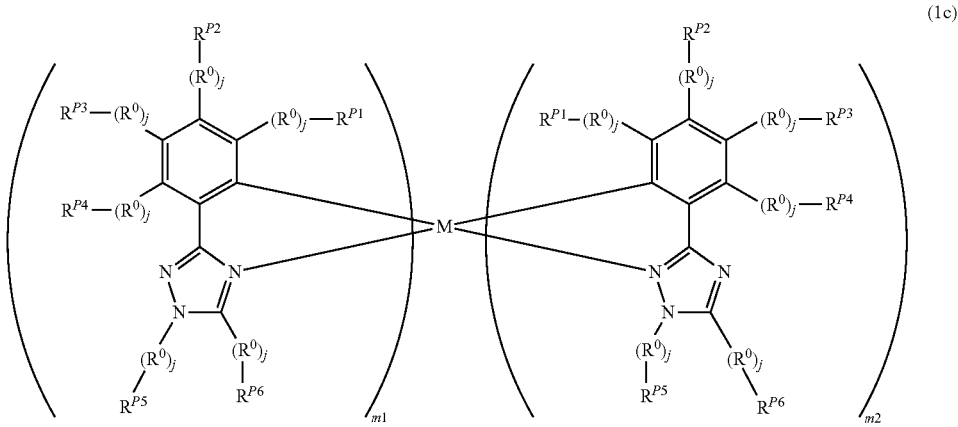

(1c)

wherein

M is a metal atom selected from the group consisting of a ruthenium atom, a rhodium atom, a palladium atom, an osmium atom, an iridium atom and a platinum atom;

each $R^0$ is independently a divalent linking group selected from the group consisting of a group represented by Formula (L-1), a group represented by Formula (L-2) and a group represented by Formula (L-3):

[Chem. 8]

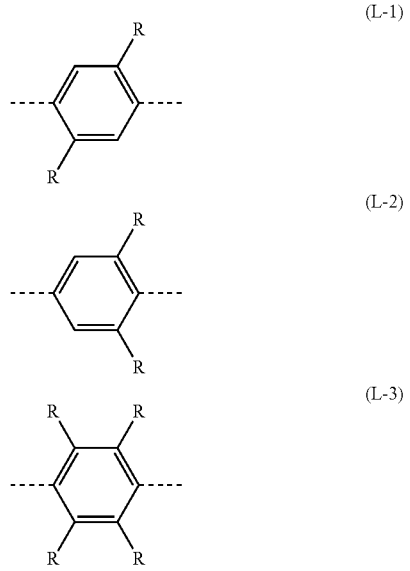

wherein each R independently represents an alkyl group; each j independently represents 0 or 1;

$R^{P1}$, $R^{P2}$, $R^{P3}$, $R^{P4}$ and $R^{P6}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, and $R^{P1}$, $R^{P2}$, $R^{P3}$, $R^{P4}$ and $R^{P6}$, which are plurally present, may be the same or different;

$R^{P5}$ represents a halogen atom, an alkyl group, an alkyloxy group, an aryl group or a monovalent heterocyclic group, and a plurality of $R^{P5}$ may be the same or different;

$R^{P1}$ and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure; and m1 and m2 are each independently 1 or 2, and m1+m2 is 2 or 3.

Fourthly, the present invention provides a composition comprising the metal complex and a charge transport compound.

Fifthly, the present invention provides a film containing the metal complex or the composition.

Sixthly, the present invention provides a light-emitting device that includes (is equipped with) electrodes composed of an anode and a cathode, and the metal complex or the composition provided between the electrodes.

Seventhly, the present invention provides a planar light source and illumination apparatus that includes (is equipped with) the device.

Effect of Invention

The metal complex of the present invention exhibits blue light emission of high color purity and is excellent in temperature dependence of the color purity. Accordingly, the metal complex of the present invention is useful for the manufacture of a light-emitting device (particularly, a blue light-emitting device).

EMBODIMENTS FOR CARRYING OUT THE INVENTION

The present invention will be described in detail below.
<Metal Complex>

The metal complex of the present invention is described.

The metal complex of the present invention is a metal complex having m ligand(s) containing a phenyl ring and a triazole ring, specifically, a metal complex represented by Formula (1a) or (1b).

The metal complexes represented by Formulae (1a) and (1b) contain ligand(s) the number of which is defined by the subscript m and bidentate ligand(s) represented by Formula (2) the number of which is defined by a subscript n. Hereinafter, a simple expression "ligand" means both the ligand the number of which is defined by the subscript m and the bidentate ligand the number of which is defined by the subscript n.

In Formulae (1a) and (1b), m is an integer of from 1 to 3, and n is an integer of from 0 to 2, preferably n is 0 or 1, and more preferably n is 0. However, m+n, the total number of ligands which can be bonded to the metal atom M, meets the valence of the metal atom M. For example, when the metal atom is an iridium atom, m is 1, 2 or 3, n is 0, 1 or 2, and m+n is 3. Preferably, m=3 and n=0, or m=2 and n=1, and more preferably, m=3 and n=0. The metal atom M can be coordinately bonded to a nitrogen atom of the triazole ring and can be covalently bonded to a carbon atom of the benzene ring. The solid lines extending from M indicate such bonds (the same shall apply hereinafter).

The metal complex represented by Formula (1a) is preferably a metal complex represented by Formula (1aa) below (that is, n=0):

[Chem. 9]

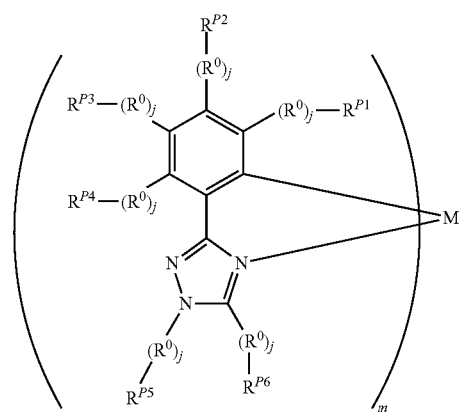

(1aa)

wherein M, $R^0$, $R^{P1}$, $R^{P2}$, $R^{P3}$, $R^{P4}$, $R^{P5}$, $R^{P6}$, j and m have the same meaning as above.

Similarly, a metal complex represented by Formula (1b) is preferably a metal complex represented by Formula (1bb) below (that is, n is 0):

[Chem. 10]

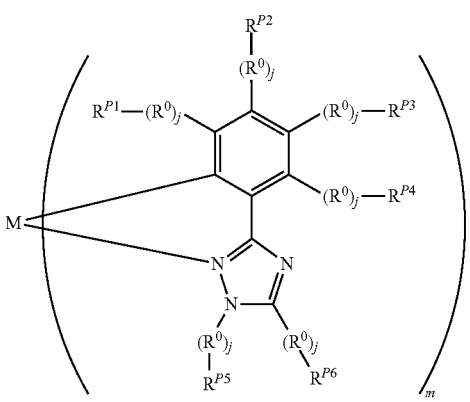

(1bb)

wherein M, $R^0$, $R^{P1}$, $R^{P2}$, $R^{P3}$, $R^{P4}$, $R^{P5}$, $R^{P6}$, j and m have the same meaning as above.

In the metal complex of the present invention, $R^{P1}$, $R^{P2}$, $R^{P3}$, $R^{P4}$, and $R^{P6}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group; and $R^{P5}$ represents a halogen atom, an alkyl group, an alkyloxy group, an aryl group or a monovalent heterocyclic group. $R^{P1}$ and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure.

Preferably, at least one of $R^{P1}$ to $R^{P4}$ and $R^{P6}$ is an alkyl group, an alkyloxy group, an aryl group having an alkyloxyphenyl group or an alkylphenyl group, or a monovalent heterocyclic group having a substituent (for example, an alkyloxyphenyl group or an alkylphenyl group).

More preferably, at least one of $R^{P1}$ to $R^{P4}$ and $R^{P6}$ is an alkyl group, an aryl group having an alkylphenyl group, or a monovalent heterocyclic group having a substituent, and $R^{P5}$ is an alkyl group, an aryl group, or a monovalent heterocyclic group.

In the metal complex of the present invention, at least one of $R^{P1}$, $R^{P2}$, $R^{P3}$, $R^{P4}$, $R^{P5}$ and $R^{P6}$ is preferably a dendron, an alkyl group substituted with an electron-acceptor group, or an aryl group substituted with an electron-acceptor group, and more preferably a dendron, from at least one viewpoint of the following:
(1) enhancing the solubility and the application and film formation properties;
(2) introducing further functionalities (for example, charge transport property); and
(3) controlling the emission color.

The dendron is a group having a branching structure and makes it possible to impart various functions to the metal complex. A highly branched large molecule having dendrons may be referred to as a dendrimer. Such molecule is described in, for example, WO02/066575, WO02/066552 and WO02/067343, and is designed and synthesized for the purpose of imparting various functions to the metal complex.

Specifically, the dendron is a group having a branching structure attributed to a substituent that the group has, and the dendron is preferably an aryl group having two or more substituents or a monovalent heterocyclic group having two or more substituents, more preferably an aryl group having two or more substituents, and further preferably a phenyl group having two or more substituents. As a substituent that an aryl group, a monovalent heterocyclic group or a phenyl group as the dendron has, preferred is an alkyl group or an alkyloxy group, and more preferred is an alkyl group. The details of the aryl group and the monovalent heterocyclic group are the same as those described below. The substituent that an aryl group, a monovalent heterocyclic group or a phenyl group as the dendron has is the same as that described below.

When the metal complex of the present invention has a structure in which the ligand is substituted with one or more dendrons, the substitution position of the dendron on the phenyl ring in the ligand may be any of $R^{P1}$, $R^{P2}$, $R^{P3}$ and $R^{P4}$ so long as the coordination of the ligand to the metal atom is not hindered, and the substitution position is preferably $R^{P2}$ or $R^{P3}$, and further preferably $R^{P3}$. The substitution position of the dendron on the triazole ring in the ligand may be any of $R^{P5}$ and $R^{P6}$ so long as the coordination of the ligand to the metal atom is not hindered, and the substitution position is preferably $R^{P5}$. Further preferably, $R^{P3}$ and $R^{P5}$ are the dendron.

When the ligand is substituted with an alkyl group or aryl group substituted with one or more electron-acceptor groups in the metal complex of the present invention, the substitution position of the alkyl group or aryl group on the phenyl ring in the ligand may be any of $R^{P1}$, $R^{P2}$, $R^{P3}$ and $R^{P4}$ so long as the coordination of the ligand to the metal atom is not hindered, and the substitution position is preferably $R^{P2}$ or $R^{P3}$. The substitution position on the triazole ring in the ligand may be any of $R^{P5}$ and $R^{P6}$ so long as the coordination of the ligand to the metal atom is not hindered.

As the electron-acceptor group, a fluorine atom or a substituent containing a fluorine atom is preferred. In the present invention, the substituent containing a fluorine atom represents a monovalent group indicated by $C_pF_qH_rO_s$. The substituent containing a fluorine atom is preferably an alkyl group substituted with an electron-acceptor group or an aryl group substituted with an electron-acceptor group. The alkyl group substituted with an electron-acceptor group or the aryl group substituted with an electron-acceptor group represents a monovalent group indicated by $C_pF_qH_r$. Here, p represents an integer selected from 1 to 10, q represents an integer selected from 1 to (2p+1), and r represents an integer selected from 0 to (2p+1). Specifically, groups represented by Formulae (F1) to (F13) are shown as examples thereof.

[Chem. 11]

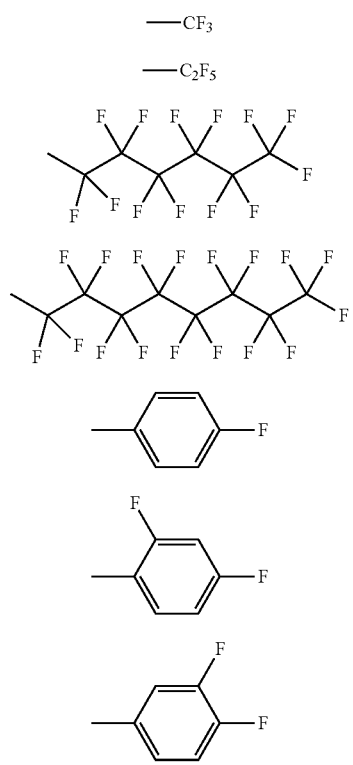

(F1)

(F2)

(F3)

(F4)

(F5)

(F6)

(F7)

-continued

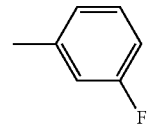 (F8)

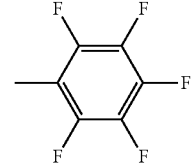 (F9)

 (F10)

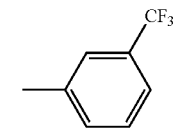 (F11)

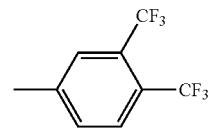 (F12)

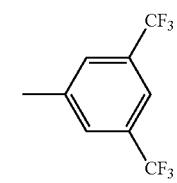 (F13)

Although a peak wavelength of emission spectrum of the metal complex of the present invention is not particularly limited, it is preferably from 430 nm to 630 nm, more preferably from 430 nm to 580 nm, further preferably from 430 nm to 530 nm, and particularly preferably from 430 nm to 510 nm.

The peak of emission spectrum of the metal complex of the present invention can be evaluated, for example, by dissolving the metal complex in an organic solvent such as xylene, toluene, chloroform and tetrahydrofuran to prepare a dilute solution (the concentration of the metal complex in the organic solvent is in a range of, for example, from $1\times10^{-6}$ to $1\times10^{-7}$ mol/L), and measuring a PL spectrum of the dilute solution.

The metal atom M in the metal complex of the present invention is a metal atom selected from the group consisting of a ruthenium atom, a rhodium atom, a palladium atom, an osmium atom, an iridium atom and a platinum atom. These metal atoms involve spin-orbit interaction in the metal complex and can produce an intersystem crossing between a singlet state and a triplet state. The metal atom M is preferably an osmium atom, an iridium atom or a platinum atom, further preferably an iridium atom or a platinum atom, and particularly preferably an iridium atom.

$R^O$ is a divalent linking group between the ligand and the group represented by $R^{P1}$, $R^{P2}$, $R^{P3}$, $R^{P4}$, $R^{P5}$ and $R^{P6}$ and each $R^O$ is independently selected from a group represented by Formula (L-1), a group represented by Formula (L-2), and a group represented by Formula (L-3). The divalent linking group is preferably a group represented by Formula (L-1) or (L-2), and more preferably a group represented by Formula (L-2).

j representing the number of the linking group $R^0$ is 0 or 1, and preferably 0.

In Formulae (L-1), (L-2) and (L-3), R represents an alkyl group. The alkyl group may be any of linear, branched and cyclic, and is preferably linear or branched, more preferably linear. The linear alkyl group has usually 1 to 10 carbon atoms, preferably 1 to 6 carbon atoms, more preferably 1 to 3 carbon atoms, and further preferably 1 carbon atom. The branched and cyclic alkyl groups have usually 3 to 10 carbon atoms, and preferably 3 to 6 carbon atoms.

Examples of the halogen atom represented by $R^{P2}$, $R^{P3}$, $R^{P4}$, $R^{P5}$ and $R^{P6}$ include a fluorine atom, a chlorine atom, a bromine atom and an iodine atom, and the halogen atom is preferably a fluorine atom.

The alkyl group represented by $R^{P1}$, $R^{P2}$, $R^{P3}$, $R^{P4}$, $R^{P5}$ and $R^{P6}$ may be any of linear, branched and cyclic. The linear alkyl group has usually 1 to 12 carbon atoms, and preferably 3 to 10 carbon atoms. The branched and cyclic alkyl groups have usually 3 to 12 carbon atoms, and preferably 3 to 10 carbon atoms. The alkyl group may have a substituent. The number of carbon atoms described above does not include the number of carbon atoms of the substituent.

Examples of such alkyl group include a methyl group, an ethyl group, a propyl group, an iso-propyl group, a butyl group, an iso-butyl group, a tert-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoroethyl group, a perfluorobutyl group, a perfluorohexyl group and a perfluorooctyl group. Among them, a pentyl group, a hexyl group, an octyl group, a 2-ethylhexyl group, a decyl group and a 3,7-dimethyloctyl group are preferred.

The alkyloxy group represented by $R^{P1}$, $R^{P2}$, $R^{P3}$, $R^{P4}$, $R^{P5}$ and $R^{P6}$ may be any of linear, branched and cyclic. The linear alkyloxy group has usually 1 to 12 carbon atoms, and preferably 3 to 10 carbon atoms. The branched and cyclic alkyloxy groups have usually 3 to 12 carbon atoms, and preferably 3 to 10 carbon atoms. The alkyloxy group may have a substituent. The number of carbon atoms described above does not include the number of carbon atoms of the substituent.

Examples of such alkyloxy group include a methyloxy group, an ethyloxy group, a propyloxy group, an iso-propyloxy group, a butyloxy group, an iso-butyloxy group, a tert-butyloxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethyloxy group, a pentafluoroethyloxy group, a perfluorobutyloxy group, a perfluorohexyloxy group, a perfluorooctyloxy group, a methyloxymethyloxy group and a 2-methyloxyethyloxy group. Among them, a pentyloxy group, a hexyloxy group, an octyloxy group, a 2-ethylhexyloxy group, a decyloxy group and a 3,7-dimethyloctyloxy group are preferred.

The alkylthio group represented by $R^{P1}$, $R^{P2}$, $R^{P3}$, $R^{P4}$ and $R^{P6}$ may be any of linear, branched and cyclic. The linear alkylthio group has usually 1 to 12 carbon atoms, and preferably 3 to 10 carbon atoms. The branched and cyclic alkylthio groups have usually 3 to 12 carbon atoms, and preferably 3 to 10 carbon atoms. The alkylthio group may have a substituent. The number of carbon atoms described above does not include the number of carbon atoms of the substituent.

Examples of such alkylthio group include a methylthio group, an ethylthio group, a propylthio group, an iso-propylthio group, a butylthio group, an iso-butylthio group, a tert-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group. Among them, a pentylthio group, a hexylthio group, an octylthio group, a 2-ethylhexylthio group, a decylthio group and a 3,7-dimethyloctylthio group are preferred.

The aryl group represented by $R^{P1}$, $R^{P2}$, $R^{P3}$, $R^{P4}$, $R^{P5}$ and $R^{P6}$ has usually 6 to 60 carbon atoms, and preferably 7 to 48 carbon atoms. The aryl group may have a substituent. The number of carbon atoms described above does not include the number of carbon atoms of the substituent.

Examples of such aryl group include a phenyl group, a $C_1$ to $C_{12}$ alkyloxyphenyl group ("$C_1$ to $C_{12}$ alkyloxy" means that the alkyloxy moiety has 1 to 12 carbon atoms, and the same shall apply hereinafter), a $C_1$ to $C_{12}$ alkylphenyl group ("$C_1$ to $C_{12}$ alkyl" means that the alkyl moiety has 1 to 12 carbon atoms, and the same shall apply hereinafter), a 1-naphthyl group, a 2-naphthyl group, a 1-anthracenyl group, a 2-anthracenyl group, a 9-anthracenyl group and a pentafluorophenyl group. Among them, a $C_1$ to $C_{12}$ alkyloxyphenyl group and a $C_1$ to $C_{12}$ alkylphenyl group are preferred. Here, the aryl group is an atomic group remaining after removing one hydrogen atom from an aromatic hydrocarbon. The aromatic hydrocarbon includes a compound having a fused ring and a compound in which two or more selected from among an independent benzene ring and/or a fused ring are bonded with each other either directly or through a group such as a vinylene group.

The above $C_1$ to $C_{12}$ alkyl is alkyl having 1 to 12 carbon atoms, and is the same as described and exemplified above in regard to the alkyl group. Accordingly, examples of $C_1$ to $C_{12}$ alkyloxy in the group include methyloxy, ethyloxy, propyloxy, iso-propyloxy, butyloxy, iso-butyloxy, tert-butyloxy, pentyloxy, hexyloxy, cyclohexyloxy, heptyloxy, octyloxy, 2-ethylhexyloxy, nonyloxy, decyloxy, 3,7-dimethyloctyloxy and lauryloxy. Examples of $C_1$ to $C_{12}$ alkylphenyl in the group include methylphenyl, ethylphenyl, dimethylphenyl, propylphenyl, mesityl, methylethylphenyl, iso-propylphenyl, butylphenyl, iso-butylphenyl, tert-butylphenyl, pentylphenyl, isoamylphenyl, hexylphenyl, heptylphenyl, octylphenyl, nonylphenyl, decylphenyl and dodecylphenyl. The same shall apply hereinafter.

The aryloxy group represented by $R^{P1}$, $R^{P2}$, $R^{P3}$, $R^{P4}$ and $R^{P6}$ has usually 6 to 60 carbon atoms, and preferably 7 to 48 carbon atoms. The aryloxy group may have a substituent. The number of carbon atoms described above does not include the number of carbon atoms of the substituent.

Examples of such aryloxy group include a phenyloxy group, a $C_1$ to $C_{12}$ alkyloxyphenyloxy group, a $C_1$ to $C_{12}$ alkylphenyloxy group, a 1-naphthyloxy group, a 2-naphthyloxy group and a pentafluorophenyloxy group. Among them, a $C_1$ to $C_{12}$ alkyloxyphenyloxy group and a $C_1$ to $C_{12}$ alkylphenyloxy group are preferred.

The arylthio group represented by $R^{P1}$, $R^{P2}$, $R^{P3}$, $R^{P4}$ and $R^{P6}$ has usually 6 to 60 carbon atoms, and preferably 7 to 48 carbon atoms. The arylthio group may have a substituent. The number of carbon atoms described above does not include the number of carbon atoms of the substituent.

Examples of such arylthio group include a phenylthio group, a $C_1$ to $C_{12}$ alkyloxyphenylthio group, a $C_1$ to $C_{12}$ alkylphenylthio group, a 1-naphthylthio group, a 2-naphthylthio group and a pentafluorophenylthio group. Among them, a $C_1$ to $C_{12}$ alkyloxyphenylthio group and a $C_1$ to $C_{12}$ alkylphenylthio group are preferred.

The arylalkyl group represented by $R^{P1}$, $R^{P2}$, $R^{P3}$, $R^{P4}$ and $R^{P6}$ has usually 7 to 60 carbon atoms, and preferably 7 to 48 carbon atoms. The arylalkyl group may have a substituent. The number of carbon atoms described above does not include the number of carbon atoms of the substituent.

Examples of such arylalkyl group include a phenyl-$C_1$ to $C_{12}$ alkyl group, a $C_1$ to $C_{12}$ alkyloxypheny-$C_1$ to $C_{12}$ alkyl group, a $C_1$ to $C_{12}$ alkylphenyl-$C_1$ to $C_{12}$ alkyl group, a 1-naphthyl-$C_1$ to $C_{12}$ alkyl group and a 2-naphthyl-$C_1$ to $C_{12}$ alkyl group. Among them, a $C_1$ to $C_{12}$ alkyloxyphenyl-$C_1$ to $C_{12}$ alkyl group and a $C_1$ to $C_{12}$ alkylphenyl-$C_1$ to $C_{12}$ alkyl group are preferred.

The arylalkyloxy group represented by $R^{P1}$, $R^{P2}$, $R^{P3}$, $R^{P4}$ and $R^{P6}$ has usually 7 to 60 carbon atoms, and preferably 7 to 48 carbon atoms. The arylalkyloxy group may have a substituent. The number of carbon atoms described above does not include the number of carbon atoms of the substituent.

Examples of such arylalkyloxy group include a phenyl-$C_1$ to $C_{12}$ alkyloxy group such as a phenylmethyloxy group, a phenylethyloxy group, a phenylbutyloxy group, a phenylpentyloxy group, a phenylhexyloxy group, a phenylheptyloxy group and a phenyloctyloxy group; a $C_1$ to $C_{12}$ alkyloxyphenyl-$C_1$ to $C_{12}$ alkyloxy group; a $C_1$ to $C_{12}$ alkylphenyl-$C_1$ to $C_{12}$ alkyloxy group; a 1-naphthyl-$C_1$ to $C_{12}$ alkyloxy group; and a 2-naphthyl-$C_1$ to $C_{12}$ alkyloxy group. Among them, a $C_1$ to $C_{12}$ alkyloxyphenyl-$C_1$ to $C_{12}$ alkyloxy group and a $C_1$ to $C_{12}$ alkylphenyl-$C_1$ to $C_{12}$ alkyloxy group are preferred.

The arylalkylthio group represented by $R^{P1}$, $R^{P2}$, $R^{P3}$, $R^{P4}$ and $R^{P6}$ has usually 7 to 60 carbon atoms, and preferably 7 to 48 carbon atoms. The arylalkylthio group may have a substituent. The number of carbon atoms described above does not include the number of carbon atoms of the substituent.

Examples of such arylalkylthio group include a phenyl-$C_1$ to $C_{12}$ alkylthio group, a $C_1$ to $C_{12}$ alkyloxyphenyl-$C_1$ to $C_{12}$ alkylthio group, a $C_1$ to $C_{12}$ alkylphenyl-$C_1$ to $C_{12}$ alkylthio group, a 1-naphthyl-$C_1$ to $C_{12}$ alkylthio group and a 2-naphthyl-$C_1$ to $C_{12}$ alkylthio group. Among them, a $C_1$ to $C_{12}$ alkyloxyphenyl-$C_1$ to $C_{12}$ alkylthio group and a $C_1$ to $C_{12}$ alkylphenyl-$C_1$ to $C_{12}$ alkylthio group are preferred.

The acyl group represented by $R^{P1}$, $R^{P2}$, $R^{P3}$, $R^{P4}$ and $R^{P6}$ has usually 2 to 20 carbon atoms, and preferably 2 to 18 carbon atoms. The acyl group may have a substituent. The number of carbon atoms described above does not include the number of carbon atoms of the substituent.

Examples of such acyl group include an acetyl group, a propionyl group, a butyryl group, an isobutyryl group, a pivaloyl group, a benzoyl group, a trifluoroacetyl group and a pentafluorobenzoyl group.

The acyloxy group represented by $R^{P1}$, $R^{P2}$, $R^{P3}$, $R^{P4}$ and $R^{P6}$ has usually 2 to 20 carbon atoms, and preferably 2 to 18 carbon atoms. The acyloxy group may have a substituent. The number of carbon atoms described above does not include the number of carbon atoms of the substituent.

Examples of such acyloxy group include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The carbamoyl group represented by $R^{P1}$, $R^{P2}$, $R^{P3}$, $R^{P4}$ and $R^{P6}$ may have a substituent and has, including the number of carbon atoms of the substituent, usually 1 to 20 carbon atoms, and preferably 2 to 18 carbon atoms (that is, the carbamoyl group is represented by a general formula: $NR^aR^b$—CO— wherein $R^a$ and $R^b$ each independently represent a hydrogen atom or a substituent).

Examples of such carbamoyl group include an aminocarbonyl group, a methylaminocarbonyl group, a dimethylaminocarbonyl group, an ethylaminocarbonyl group, a propylaminocarbonyl group and a butylaminocarbonyl group.

The amido group represented by $R^{P1}$, $R^{P2}$, $R^{P3}$, $R^{P4}$ and $R^{P6}$ may have a substituent and has, including the number of carbon atoms of the substituent, usually 1 to 20 carbon atoms, and preferably 2 to 18 carbon atoms (that is, the amido group is represented by a general formula: $R^c$—CO—$NR^d$— wherein $R^c$ and $R^d$ each independently represent a hydrogen atom or a substituent).

Examples of such amido group include a formamido group, an acetamido group, a propioamido group, a butyramido group, a benzamido group, a trifluoroacetamido group, a pentafluorobenzamido group, a diformamido group, a diacetamido group, a dipropioamido group, a dibutyramido group, a dibenzamido group, a ditrifluoroacetamido group and a dipentafluorobenzamido group.

The acid imido group represented by $R^{P1}$, $R^{P2}$, $R^{P3}$, $R^{P4}$ and $R^{P6}$ means a monovalent residue that is obtained by removing, from an acid imide, one hydrogen atom bonded to a nitrogen atom thereof. The acid imido group has usually 2 to 60 carbon atoms, and preferably 2 to 48 carbon atoms. The acid imido group may have a substituent. The number of carbon atoms described above does not include the number of carbon atoms of the substituent.

Examples of such acid imido group include groups indicated by structural formulae below.

[Chem. 12]

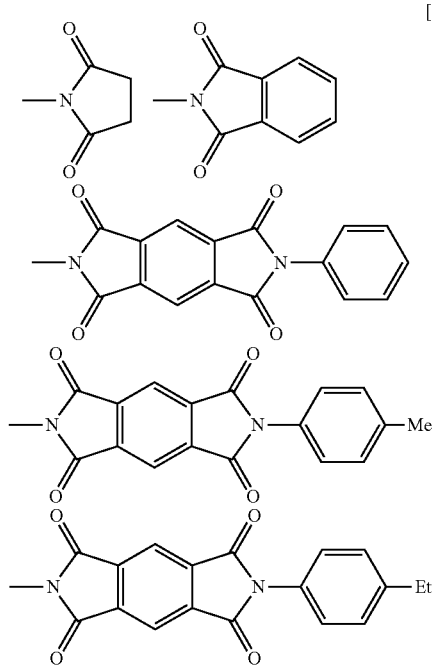

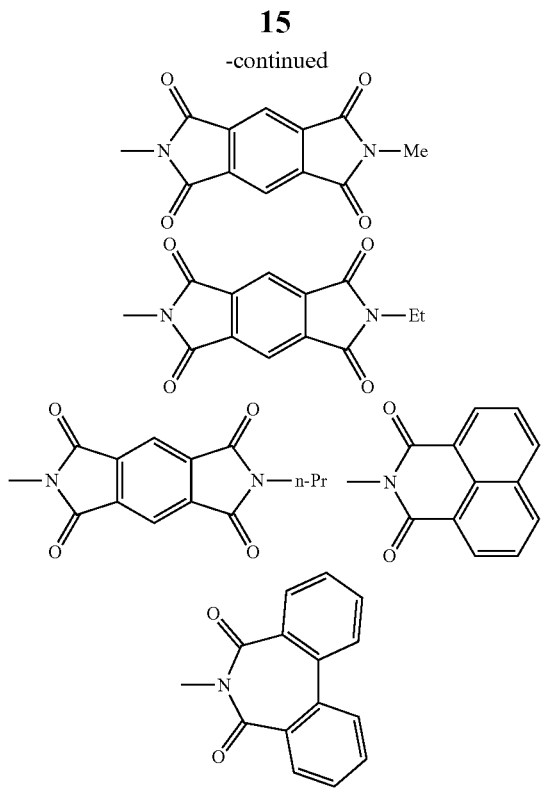

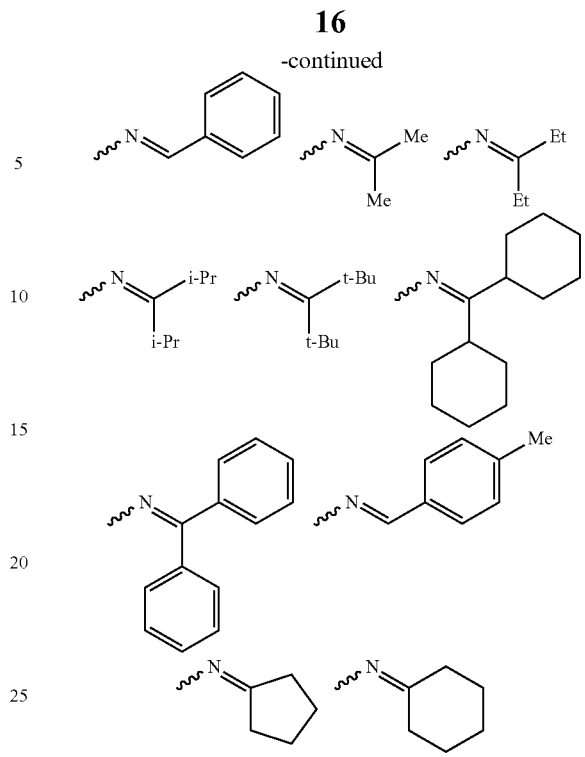

In the formulae, a line extending from a nitrogen atom represents a bond, Me represents a methyl group, Et represents an ethyl group, and n-Pr represents an n-propyl group. The same shall apply hereinafter.

The imine residue represented by $R^{P1}$, $R^{P2}$, $R^{P3}$, $R^{P4}$ and $R^{P6}$ means a monovalent residue remaining after removing one hydrogen atom from an imine compound (that is, an organic compound having —N=C— in the molecule thereof. Examples thereof include aldimine, ketimine, and a compound in which a hydrogen atom bonded to a nitrogen atom in the molecule thereof is substituted with an alkyl group or the like). The imine residue has usually 2 to 20 carbon atoms, and preferably 2 to 18 carbon atoms. The imine residue may have a substituent. The number of carbon atoms described above does not include the number of carbon atoms of the substituent.

Examples of such imine residue include groups indicated by structural formulae below.

[Chem. 13]

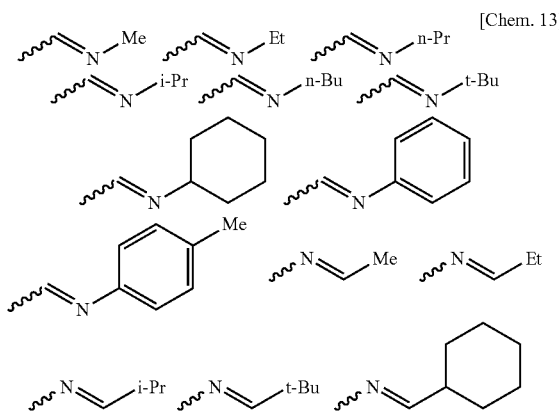

In the formulae, i-Pr represents an iso-propyl group, n-Bu represents an n-butyl group, and t-Bu represents a tert-butyl group. A bond indicated by a wavy line means that the bond is a "bond represented by a wedge-shape" and/or a "bond represented by a broken line". Here, the "bond represented by a wedge-shape" means a bond projecting from the surface of the paper toward the front, and the "bond represented by a broken line" means a bond projecting from the surface of the paper toward the back.

The substituted amino group represented by $R^{P1}$, $R^{P2}$, $R^{P3}$, $R^{P4}$ and $R^{P6}$ means an amino group in which one or two hydrogen atoms of an amino group are substituted with one or two groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted amino group. The substituted amino group has usually 1 to 60 carbon atoms, and preferably 2 to 48 carbon atoms.

Examples of such substituted amino group include a methylamino group, a dimethylamino group, an ethylamino group, a diethylamino group, a propylamino group, a dipropylamino group, an iso-propylamino group, a diisopropylamino group, a butylamino group, an iso-butylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a $C_1$ to $C_{12}$ alkyloxyphenylamino group, a di($C_1$ to $C_{12}$ alkyloxyphenyl) amino group, a di($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl-$C_1$ to $C_{12}$ alkylamino group, a $C_1$ to $C_{12}$ alkyloxyphenyl-$C_1$ to $C_{12}$ alkylamino group, a $C_1$ to $C_{12}$ alkylphenyl-$C_1$ to $C_{12}$ alkylamino group, a di($C_1$ to $C_{12}$ alkyloxyphenyl-$C_1$ to $C_{12}$ alkyl)amino group, a di($C_1$ to $C_{12}$ alkylphenyl-$C_1$ to $C_{12}$ alkyl)amino group, a 1-naphthyl-$C_1$ to $C_{12}$ alkylamino group and a 2-naphthyl-$C_1$ to $C_{12}$ alkylamino group.

The substituted silyl group represented by $R^{P1}$, $R^{P2}$, $R^{P3}$, $R^{P4}$ and $R^{P6}$ means a silyl group in which one, two or three hydrogen atoms of a silyl group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silyl group. The substituted silyl group has usually 1 to 60 carbon atoms, and preferably 3 to 48 carbon atoms.

Examples of such substituted silyl group include a trimethylsilyl group, a triethylsilyl group, a tripropylsilyl group, a tri-iso-propylsilyl group, a dimethyl-iso-propylsilyl group, a diethyl-iso-propylsilyl group, a tert-butylsilyldimethylsilyl group, a pentyldimethylsilyl group, a hexyldimethylsilyl group, a heptyldimethylsilyl group, an octyldimethylsilyl group, a 2-ethylhexyl-dimethylsilyl group, a nonyldimethylsilyl group, a decyldimethylsilyl group, a 3,7-dimethyloctyl-dimethylsilyl group, a lauryldimethylsilyl group, a phenyl-$C_1$ to $C_{12}$ alkylsilyl group, a $C_1$ to $C_{12}$ alkyloxyphenyl-$C_1$ to $C_{12}$ alkylsilyl group, a $C_1$ to $C_{12}$ alkylphenyl-$C_1$ to $C_{12}$ alkylsilyl group, a 1-naphthyl-$C_1$ to $C_{12}$ alkylsilyl group, a 2-naphthyl-$C_1$ to $C_{12}$ alkylsilyl group, a phenyl-$C_1$ to $C_{12}$ alkyldimethylsilyl group, a triphenylsilyl group, a tri-p-xylylsilyl group, a tribenzylsilyl group, a diphenylmethylsilyl group, a tert-butyldiphenylsilyl group and a dimethylphenylsilyl group.

The substituted silyloxy group represented by $R^{P1}$, $R^{P2}$, $R^{P3}$, $R^{P4}$ and $R^{P6}$ means a silyloxy group in which one, two or three hydrogen atoms of a silyloxy group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silyloxy group. The substituted silyloxy group has usually 1 to 60 carbon atoms, and preferably 3 to 48 carbon atoms.

Examples of such substituted silyloxy group include a trimethylsilyloxy group, a triethylsilyloxy group, a tripropylsilyloxy group, a tri-iso-propylsilyloxy group, a dimethyl-iso-propylsilyloxy group, a diethyl-iso-propylsilyloxy group, a tert-butylsilyldimethylsilyloxy group, a pentyldimethylsilyloxy group, a hexyldimethylsilyloxy group, a heptyldimethylsilyloxy group, an octyldimethylsilyloxy group, a 2-ethylhexyl-dimethylsilyloxy group, a nonyldimethylsilyloxy group, a decyldimethylsilyloxy group, a 3,7-dimethyloctyl-dimethylsilyloxy group, a lauryldimethylsilyloxy group, a phenyl-$C_1$ to $C_{12}$ alkylsilyloxy group, a $C_1$ to $C_{12}$ alkyloxyphenyl-$C_1$ to $C_{12}$ alkylsilyloxy group, a $C_1$ to $C_{12}$ alkylphenyl-$C_1$ to $C_{12}$ alkylsilyloxy group, a 1-naphthyl-$C_1$ to $C_{12}$ alkylsilyloxy group, a 2-naphthyl-$C_1$ to $C_{12}$ alkylsilyloxy group, a phenyl-$C_1$ to $C_{12}$ alkyldimethylsilyloxy group, a triphenylsilyloxy group, a tri-p-xylylsilyloxy group, a tribenzylsilyloxy group, a diphenylmethylsilyloxy group, a tert-butyldiphenylsilyloxy group and a dimethylphenylsilyloxy group.

The substituted silylthio group represented by $R^{P1}$, $R^{P2}$, $R^{P3}$, $R^{P4}$ and $R^{P6}$ means a silylthio group in which one, two or three hydrogen atoms of a silylthio group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silylthio group. The substituted silylthio group has usually 1 to 60 carbon atoms, and preferably 3 to 48 carbon atoms.

Examples of such substituted silylthio group include a trimethylsilylthio group, a triethylsilylthio group, a tripropylsilylthio group, a tri-iso-propylsilylthio group, a dimethyl-iso-propylsilylthio group, a diethyl-iso-propylsilylthio group, a tert-butylsilyldimethylsilylthio group, a pentyldimethylsilylthio group, a hexyldimethylsilylthio group, a heptyldimethylsilylthio group, an octyldimethylsilylthio group, a 2-ethylhexyl-dimethylsilylthio group, a nonyldimethylsilylthio group, a decyldimethylsilylthio group, a 3,7-dimethyloctyl-dimethylsilylthio group, a lauryldimethylsilylthio group, a phenyl-$C_1$ to $C_{12}$ alkylsilylthio group, a $C_1$ to $C_{12}$ alkyloxyphenyl-$C_1$ to $C_{12}$ alkylsilylthio group, a $C_1$ to $C_{12}$ alkylphenyl-$C_1$ to $C_{12}$ alkylsilylthio group, a 1-naphthyl-$C_1$ to $C_{12}$ alkylsilylthio group, a 2-naphthyl-$C_1$ to $C_{12}$ alkylsilylthio group, a phenyl-$C_1$ to $C_{12}$ alkyldimethylsilylthio group, a triphenylsilylthio group, a tri-p-xylylsilylthio group, a tribenzylsilylthio group, a diphenylmethylsilylthio group, a tert-butyldiphenylsilylthio group and a dimethylphenylsilylthio group.

The substituted silylamino group represented by $R^{P1}$, $R^{P2}$, $R^{P3}$, $R^{P4}$ and $R^{P6}$ means a silylamino group in which one, two or three hydrogen atoms of a silylamino group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic amino group may have a substituent, the number of carbon atoms of the substituent is not included in the number of carbon atoms of the substituted silylamino group. The substituted silylamino group has usually 1 to 60 carbon atoms, and preferably 3 to 48 carbon atoms.

Examples of such substituted silylamino group include a trimethylsilylamino group, a triethylsilylamino group, a tripropylsilylamino group, a tri-iso-propylsilylamino group, a dimethyl-iso-propylsilylamino group, a diethyl-iso-propylsilylamino group, a tert-butylsilyldimethylsilylamino group, a pentyldimethylsilylamino group, a hexyldimethylsilylamino group, a heptyldimethylsilylamino group, an octyldimethylsilylamino group, a 2-ethylhexyl-dimethylsilylamino group, a nonyldimethylsilylamino group, a decyldimethylsilylamino group, a 3,7-dimethyloctyl-dimethylsilylamino group, a lauryldimethylsilylamino group, a phenyl-$C_1$ to $C_{12}$ alkylsilylamino group, a $C_1$ to $C_{12}$ alkyloxyphenyl-$C_1$ to $C_{12}$ alkylsilylamino group, a $C_1$ to $C_{12}$ alkylphenyl-$C_1$ to $C_{12}$ alkylsilylamino group, a 1-naphthyl-$C_1$ to $C_{12}$ alkylsilylamino group, a 2-naphthyl-$C_1$ to $C_{12}$ alkylsilylamino group, a phenyl-$C_1$ to $C_{12}$ alkyldimethylsilylamino group, a triphenylsilylamino group, a tri-p-xylylsilylamino group, a tribenzylsilylamino group, a diphenylmethylsilylamino group, a tert-butyldiphenylsilylamino group and a dimethylphenylsilylamino group.

The monovalent heterocyclic group represented by $R^{P1}$, $R^{P2}$, $R^{P3}$, $R^{P4}$, $R^{P5}$ and $R^{P6}$ means an atomic group remaining after removing one hydrogen atom from a heterocyclic compound. The monovalent heterocyclic group has usually 4 to 60 carbon atoms, and preferably 4 to 20 carbon atoms. The monovalent heterocyclic group may have a substituent. The number of carbon atoms described above does not include the number of carbon atoms of the substituent. Here, the heterocyclic compound refers to a compound containing not only a carbon atom but also a hetero atom such as an oxygen atom, a sulfur atom, a nitrogen atom, a phosphorus atom and a boron atom as an element constituting the ring, among organic compounds having a cyclic structure.

Examples of such monovalent heterocyclic group include a thienyl group, a $C_1$ to $C_{12}$ alkylthienyl group, a pyrrolyl group, a furyl group, a pyridyl group, a $C_1$ to $C_{12}$ alkylpyridyl group, a piperidyl group, a quinolyl group and an isoquinolyl group. Among them, a thienyl group, a $C_1$ to $C_{12}$ alkylthienyl group, a pyridyl group and a $C_1$ to $C_{12}$ alkylpyridyl group are preferred.

The heteroaryloxy group represented by $R^{P1}$, $R^{P2}$, $R^{P3}$, $R^{P4}$ and $R^{P6}$ has usually 6 to 60 carbon atoms, and preferably 7 to 48 carbon atoms. The heteroaryloxy group may have a substituent. The number of carbon atoms described above does not include the number of carbon atoms of the substituent.

Examples of such heteroaryloxy group include a thienyloxy group, a $C_1$ to $C_{12}$ alkyloxythienyloxy group, a $C_1$ to $C_{12}$ alkylthienyloxy group, a pyridyloxy group, a $C_1$ to $C_{12}$ alkyloxypyridyloxy group, a $C_1$ to $C_{12}$ alkylpyridyloxy group and an isoquinolyloxy group. Among them, a $C_1$ to $C_{12}$ alkyloxypyridyloxy group and a $C_1$ to $C_{12}$ alkylpyridyloxy group are preferred.

Examples of the $C_1$ to $C_{12}$ alkylpyridyloxy group include a methylpyridyloxy group, an ethylpyridyloxy group, a dimethylpyridyloxy group, a propylpyridyloxy group, a 1,3,5-trimethylpyridyloxy group, a methylethylpyridyloxy group, an iso-propylpyridyloxy group, a butylpyridyloxy group, an iso-butylpyridyloxy group, a tert-butylpyridyloxy group, a pentylpyridyloxy group, an isoamylpyridyloxy group, a hexylpyridyloxy group, a heptylpyridyloxy group, an octylpyridyloxy group, a nonylpyridyloxy group, a decylpyridyloxy group and a dodecylpyridyloxy group.

The heteroarylthio group represented by $R^{P1}$, $R^{P2}$, $R^{P3}$, $R^{P4}$ and $R^{P6}$ has usually about 6 to 60 carbon atoms, and preferably 7 to 48 carbon atoms. The heteroarylthio group may have a substituent. The number of carbon atoms described above does not include the number of carbon atoms of the substituent.

Examples of such heteroarylthio group include a pyridylthio group, a $C_1$ to $C_{12}$ alkyloxypyridylthio group, a $C_1$ to $C_{12}$ alkylpyridylthio group and an isoquinolylthio group. Among them, a $C_1$ to $C_{12}$ alkyloxypyridylthio group and a $C_1$ to $C_{12}$ alkylpyridylthio group are preferred.

The arylalkenyl group represented by $R^{P1}$, $R^{P2}$, $R^{P3}$, $R^{P4}$ and $R^{P6}$ has usually 7 to 60 carbon atoms, and preferably 7 to 48 carbon atoms. The arylalkenyl group may have a substituent. The number of carbon atoms described above does not include the number of carbon atoms of the substituent.

Examples of such arylalkenyl group include a phenyl-$C_2$ to $C_{12}$ alkenyl group ("$C_2$ to $C_{12}$ alkenyl" means that the alkenyl moiety has 2 to 12 carbon atoms, and the same shall apply hereinafter), a $C_1$ to $C_{12}$ alkyloxyphenyl-$C_2$ to $C_{12}$ alkenyl group, a $C_1$ to $C_{12}$ alkylphenyl-$C_2$ to $C_{12}$ alkenyl group, a 1-naphthyl-$C_2$ to $C_{12}$ alkenyl group and a 2-naphthyl-$C_2$ to $C_{12}$ alkenyl group. Among them, a $C_1$ to $C_{12}$ alkyloxyphenyl-$C_2$ to $C_{12}$ alkenyl group and a $C_2$ to $C_{12}$ alkylphenyl-$C_1$ to $C_{12}$ alkenyl group are preferred.

Examples of the $C_2$ to $C_{12}$ alkenyl include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

The arylalkynyl group represented by $R^{P1}$, $R^{P2}$, $R^{P3}$, $R^{P4}$ and $R^{P6}$ has usually 7 to 60 carbon atoms, and preferably 7 to 48 carbon atoms. The arylalkynyl group may have a substituent. The number of carbon atoms described above does not include the number of carbon atoms of the substituent.

Examples of such arylalkynyl group include a phenyl-$C_2$ to $C_{12}$ alkynyl group ("$C_2$ to $C_{12}$ alkynyl" means that the alkynyl moiety has 2 to 12 carbon atoms, and the same shall apply hereinafter), a $C_1$ to $C_{12}$ alkyloxyphenyl-$C_2$ to $C_{12}$ alkynyl group, a $C_1$ to $C_{12}$ alkylphenyl-$C_2$ to $C_{12}$ alkynyl group, a 1-naphthyl-$C_2$ to $C_{12}$ alkynyl group and a 2-naphthyl-$C_2$ to $C_{12}$ alkynyl group. Among them, a $C_1$ to $C_{12}$ alkyloxyphenyl-$C_2$ to $C_{12}$ alkynyl group and a $C_1$ to $C_{12}$ alkylphenyl-$C_2$ to $C_{12}$ alkynyl group are preferred.

Examples of the above $C_2$ to $C_{12}$ alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl and 1-octynyl.

The substituted carboxyl group represented by $R^{P1}$, $R^{P2}$, $R^{P3}$, $R^{P4}$ and $R^{P6}$ (the substituted carboxyl group is represented by a general formula: $R^e$—O—CO— wherein $R^e$ represents an alkyl group, an aryl group, an arylalkyl group or a monovalent heterocyclic group) has usually 1 to 60 carbon atoms, and preferably 2 to 48 carbon atoms. The substituted carboxyl group means a carboxyl group in which a hydrogen atom is substituted with an alkyl group, an aryl group, an arylalkyl group or a monovalent heterocyclic group. Although the alkyl group, the aryl group, the arylalkyl group or the monovalent heterocyclic group may have a substituent, the number of carbon atoms of the substituent is not included in the number of carbon atoms described above.

Examples of such substituted carboxyl group include a methyloxycarbonyl group, an ethyloxycarbonyl group, a propyloxycarbonyl group, an iso-propyloxycarbonyl group, a butyloxycarbonyl group, an iso-butyloxycarbonyl group, a tert-butyloxycarbonyl group, a pentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a nonyloxycarbonyl group, a decyloxycarbonyl group, a 3,7-dimethyloctyloxycarbonyl group, a dodecyloxycarbonyl group, a trifluoromethyloxycarbonyl group, a pentafluoroethyloxycarbonyl group, a perfluorobutyloxycarbonyl group, a perfluorohexyloxycarbonyl group, a perfluorooctyloxycarbonyl group, a pyridyloxycarbonyl group, a naphthyloxycarbonyl group and a pyridyloxycarbonyl group.

When the groups noted above have a substituent, examples of the substituent include a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group and a cyano group. The details of these groups are the same as those described and exemplified above. The substituent is preferably a halogen atom, an alkyl group, an alkyloxy group, an aryl group or a monovalent heterocyclic group, and more preferably an alkyl group, an aryl group or a monovalent heterocyclic group. When the groups noted above have a substituent, the number of substituents is usually 1 to 3, preferably 1 to 2, and more preferably 1.

In the metal complex of the present invention, the metal atom M is a metal atom selected from the group consisting of a ruthenium atom, a rhodium atom, a palladium atom, an iridium atom and a platinum atom, and is preferably an iridium atom or a platinum atom, more preferably an iridium atom.

In the metal complex of the present invention, it is preferable that any one of $R^{P1}$, $R^{P2}$, $R^{P3}$, $R^{P4}$, $R^{P5}$ and $R^{P6}$ is an electron-donor substituent. The electron-donor substituent include an alkyloxy group and an alkyl group.

Although the bidentate ligand, which is a portion represented by Formula (2), is not limited, the bidentate ligand is preferably monoanionic so that the metal complex of the present invention is neutral. Examples thereof include structures below.

[Chem. 14]

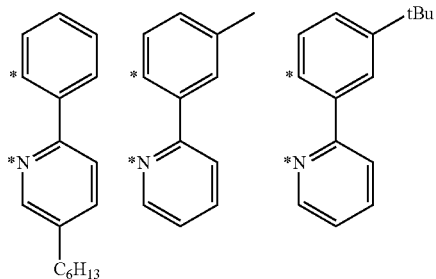

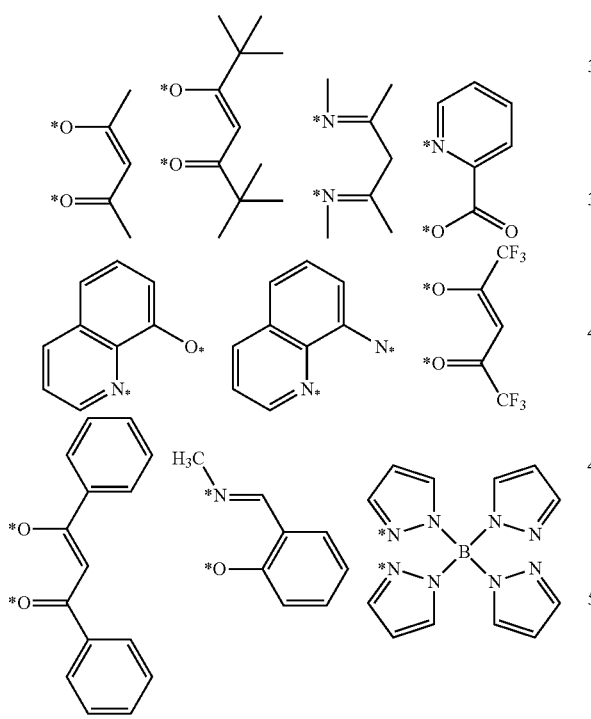

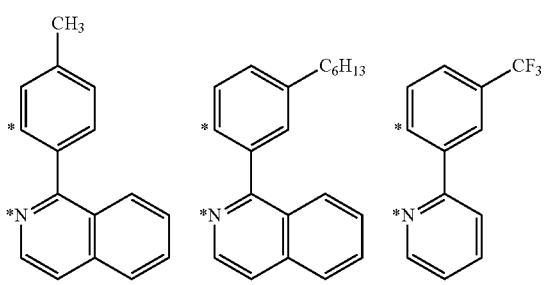

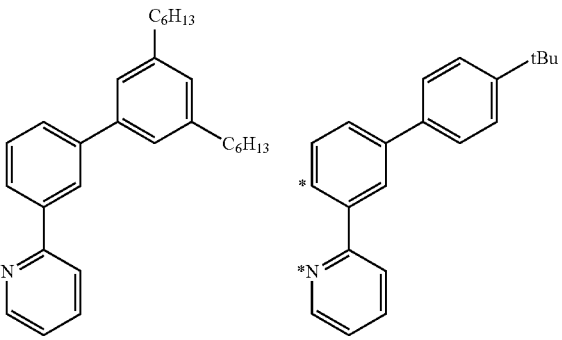

[Chem. 15]

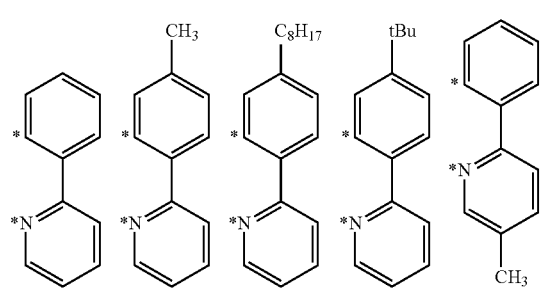

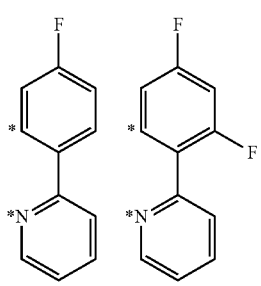

In the formulae, * represents a position bonding to the metal atom M.

Examples of the metal complex of the present invention include structures represented by formulae below.

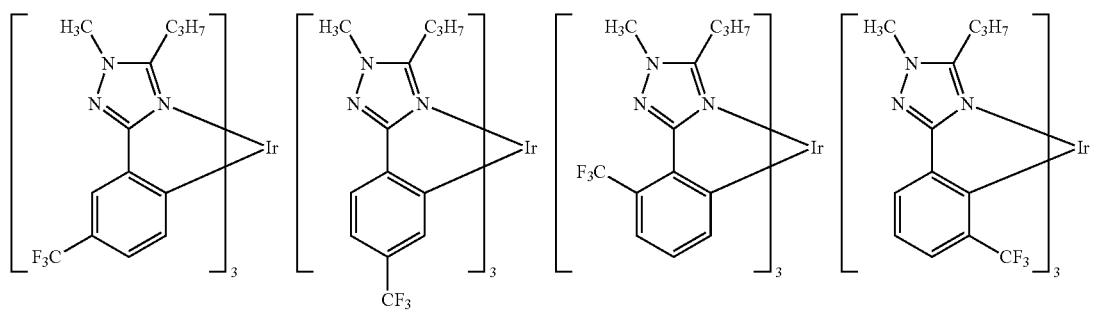
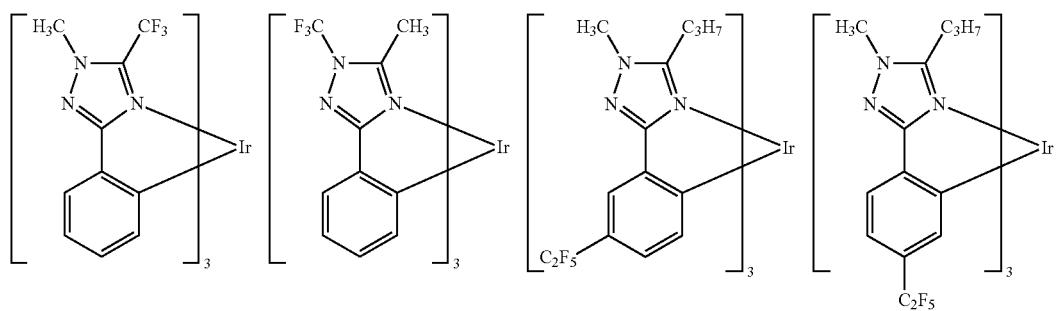
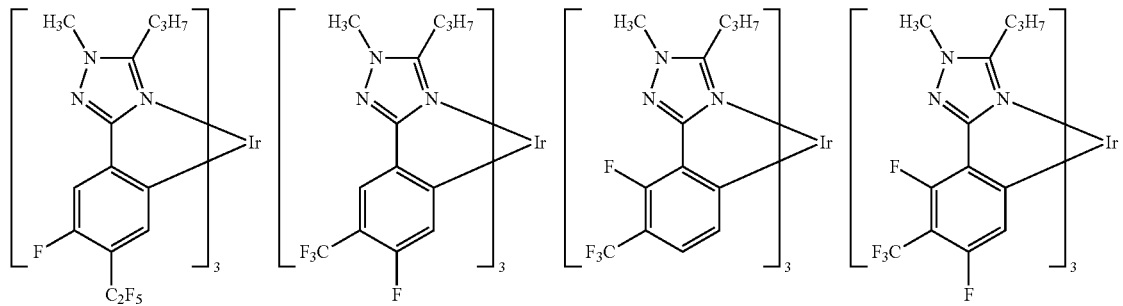
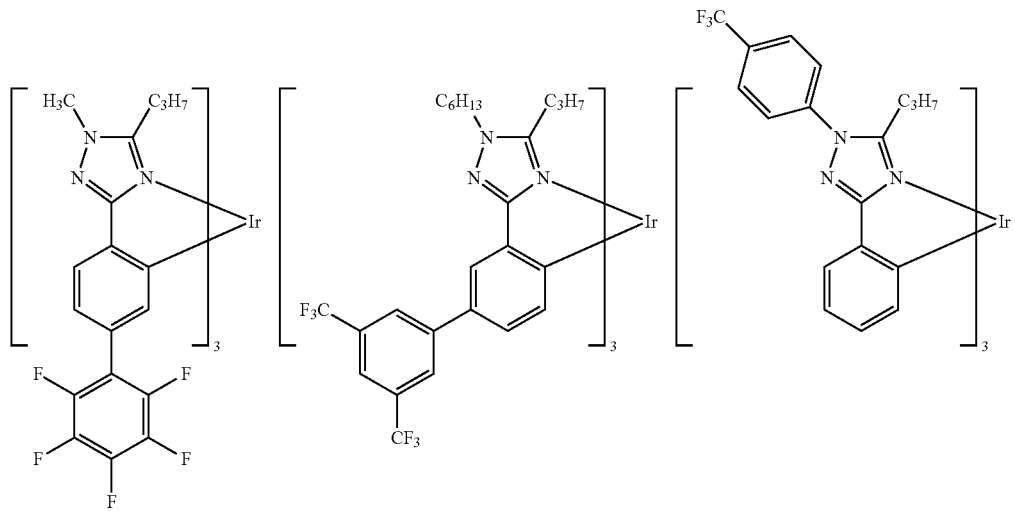
[Chem. 16]

-continued
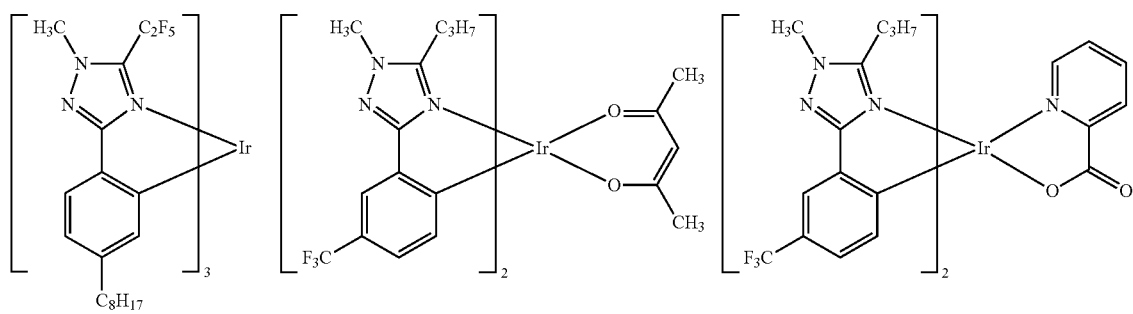
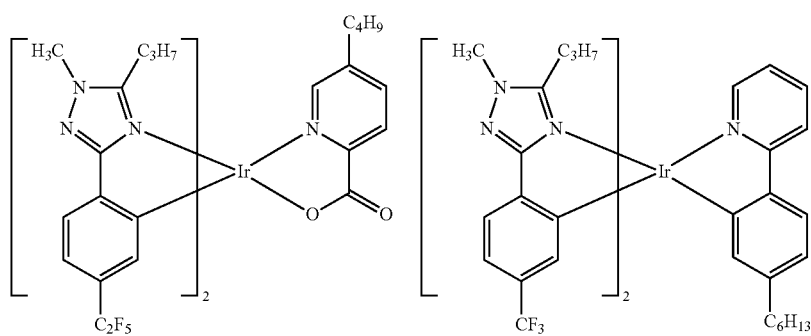
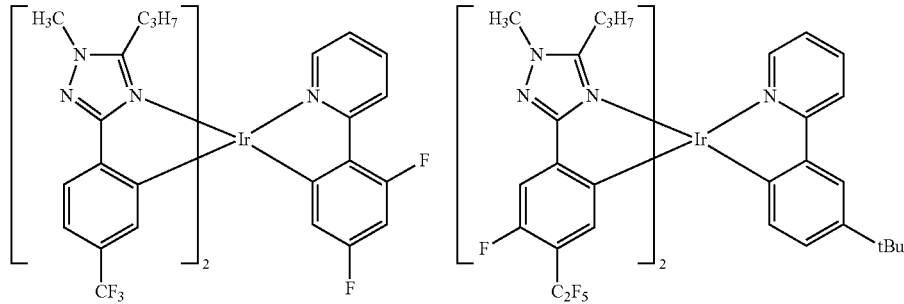
[Chem. 17]
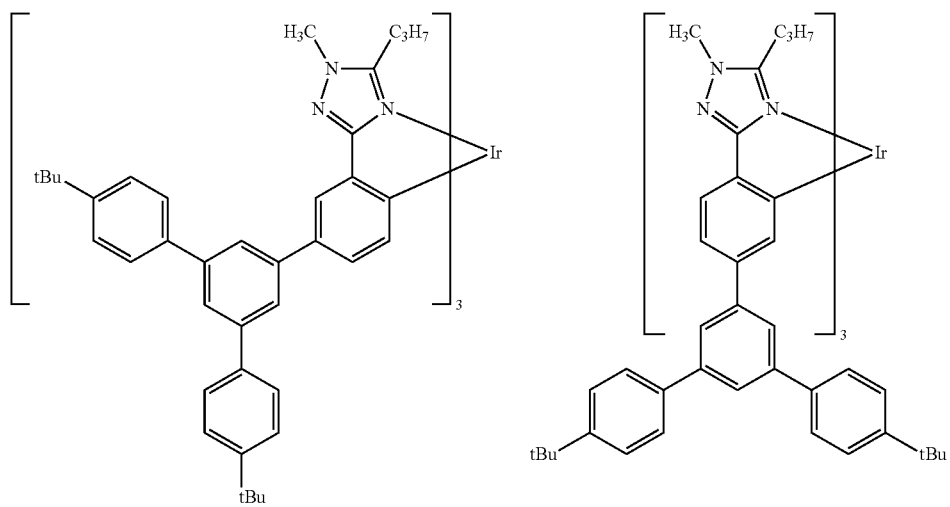

-continued
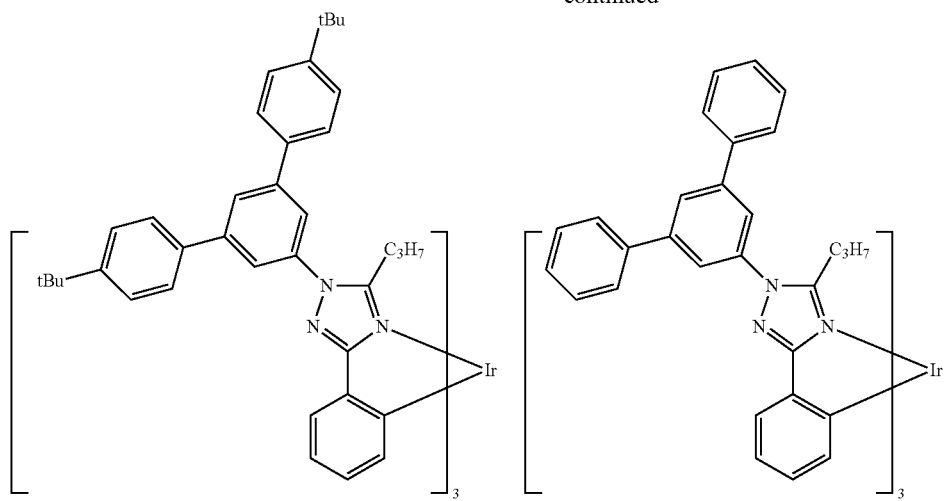
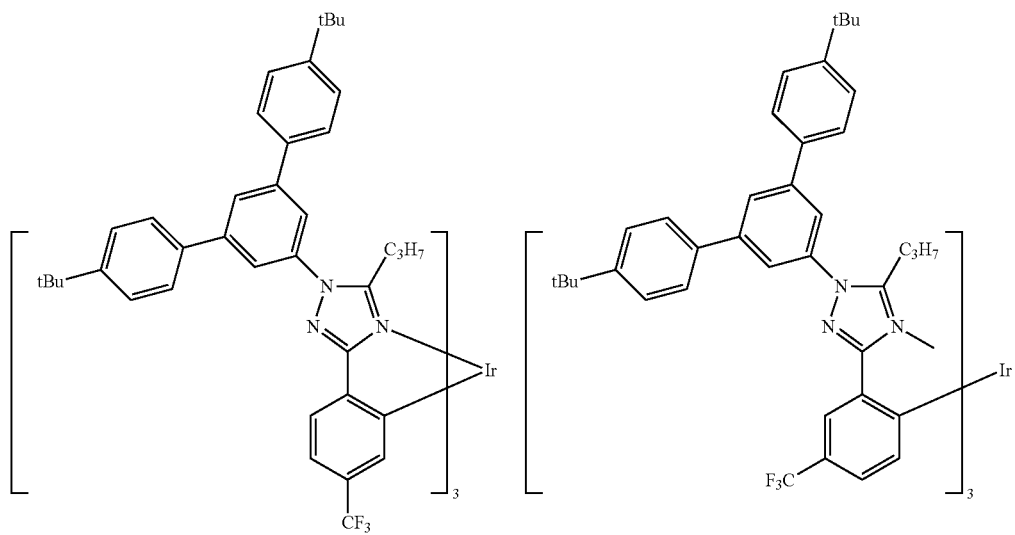
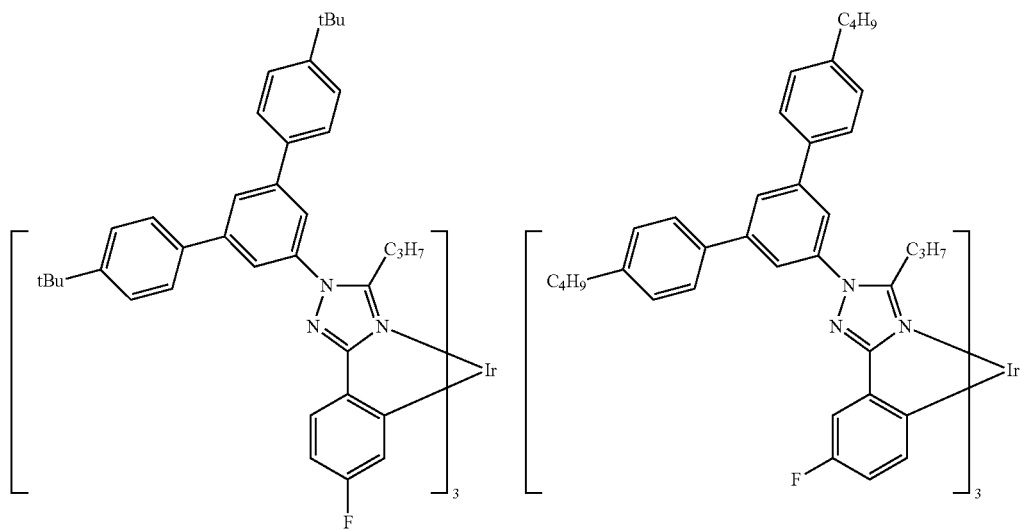

29
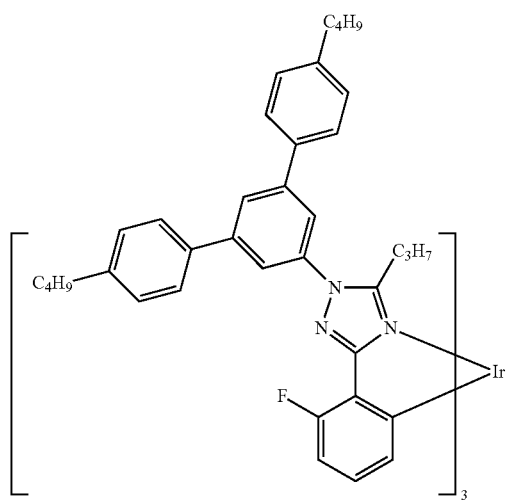
30
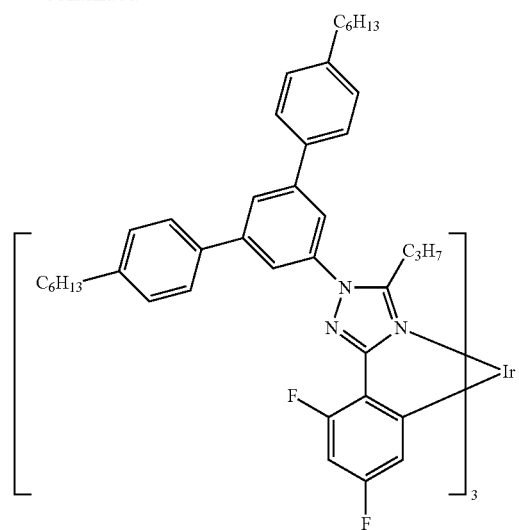
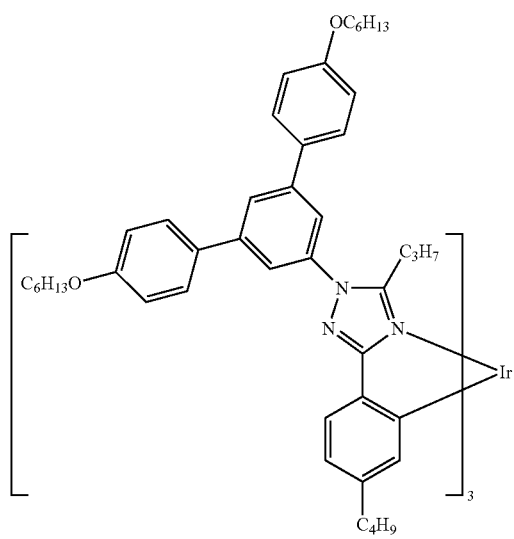
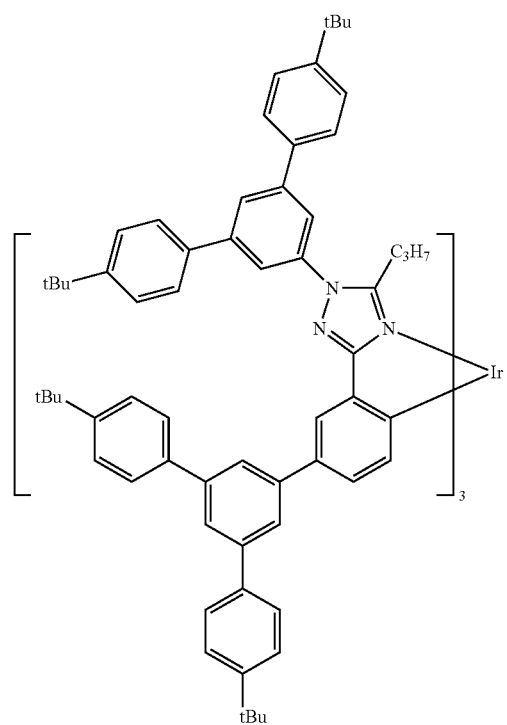

-continued
31
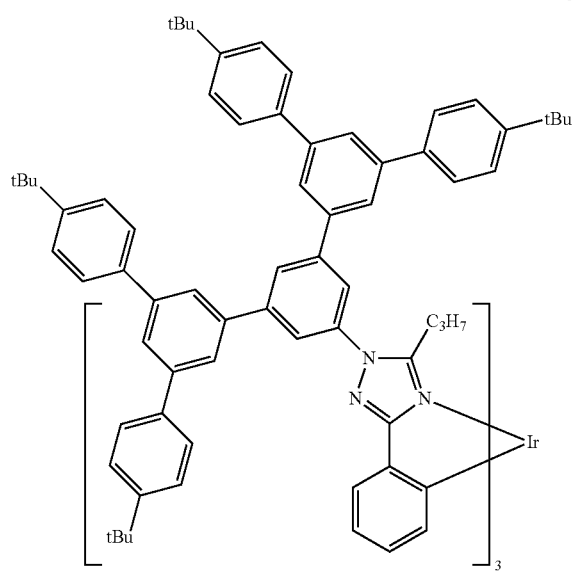
32
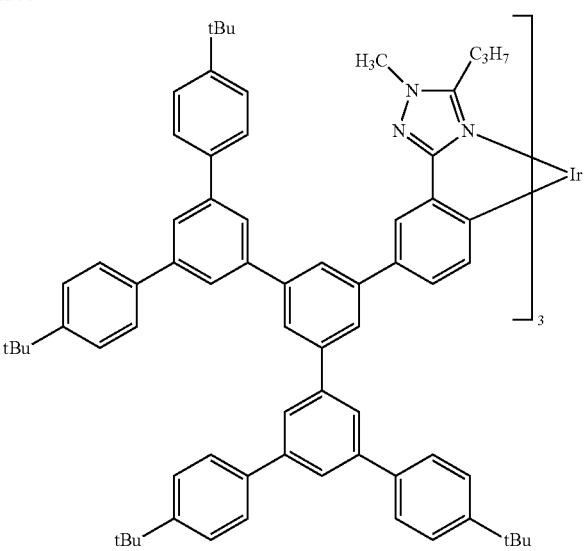
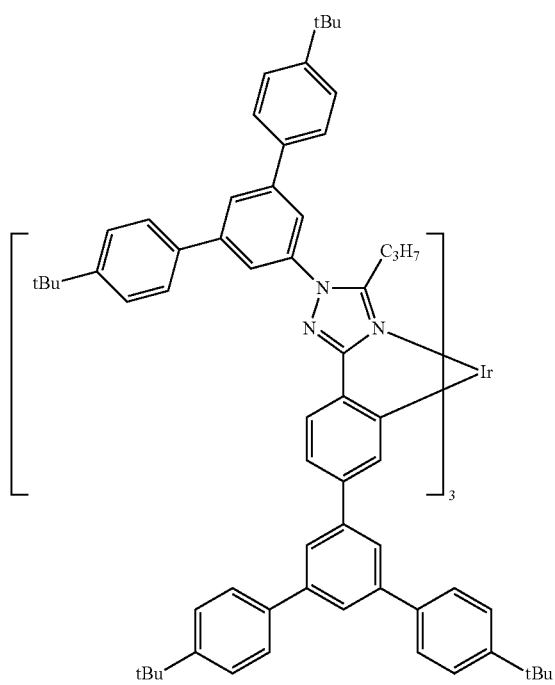

-continued
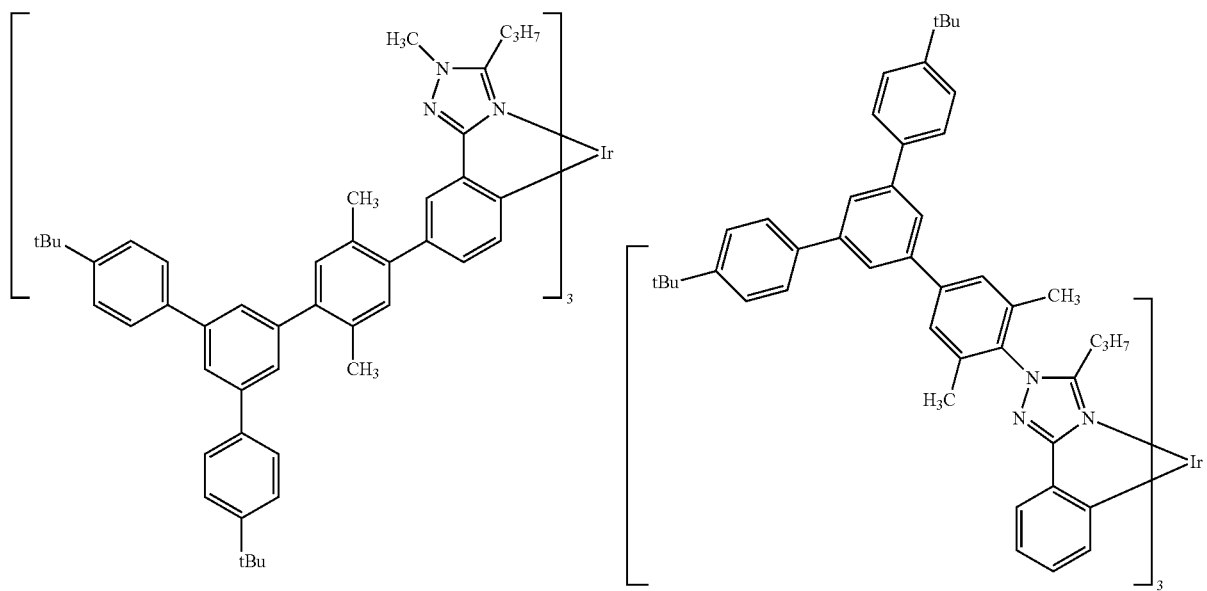
[Chem. 18]
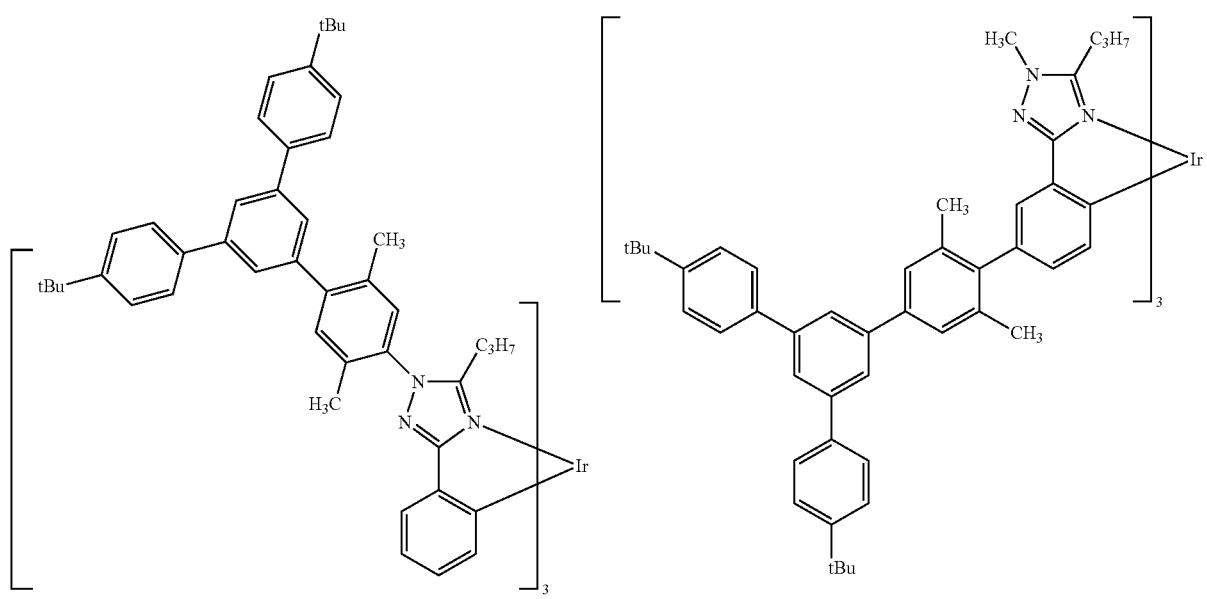

35 36
-continued
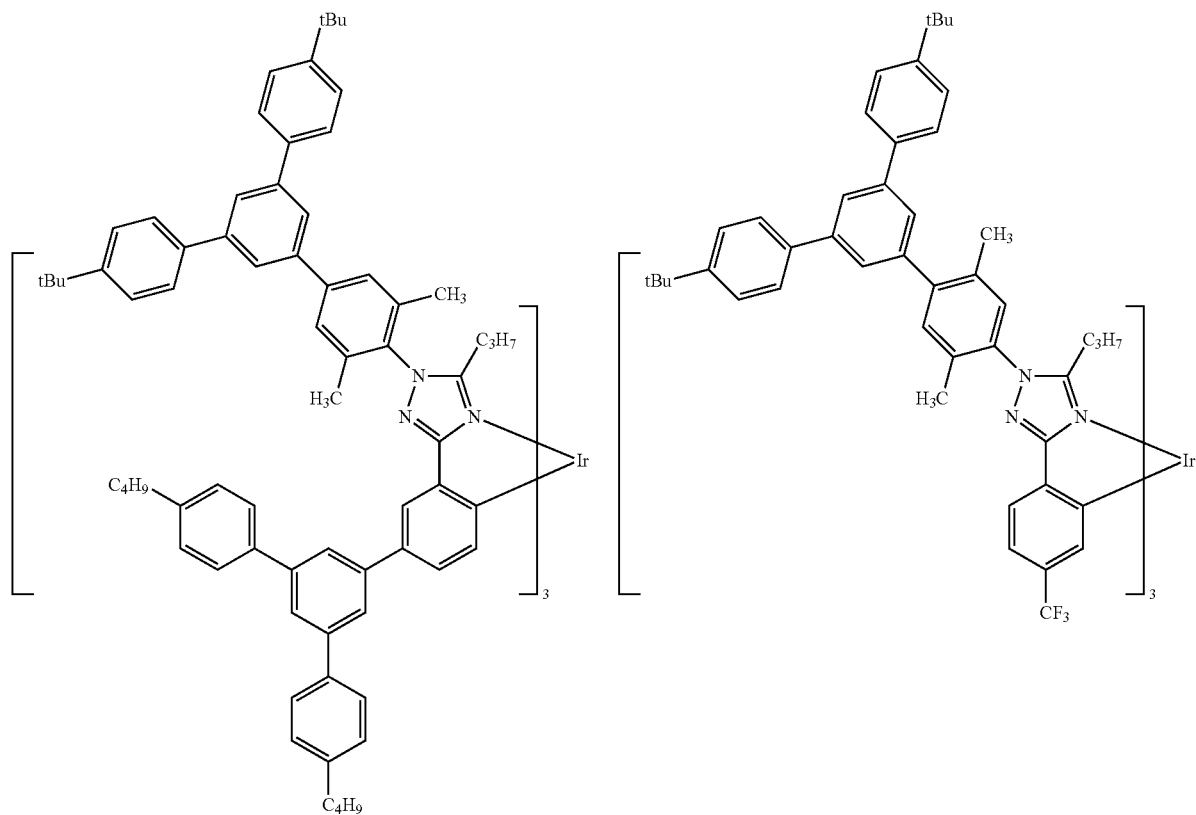
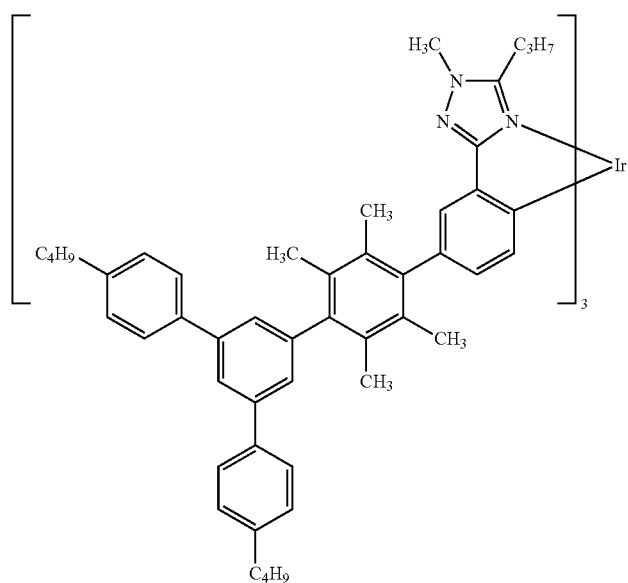

37 38
-continued
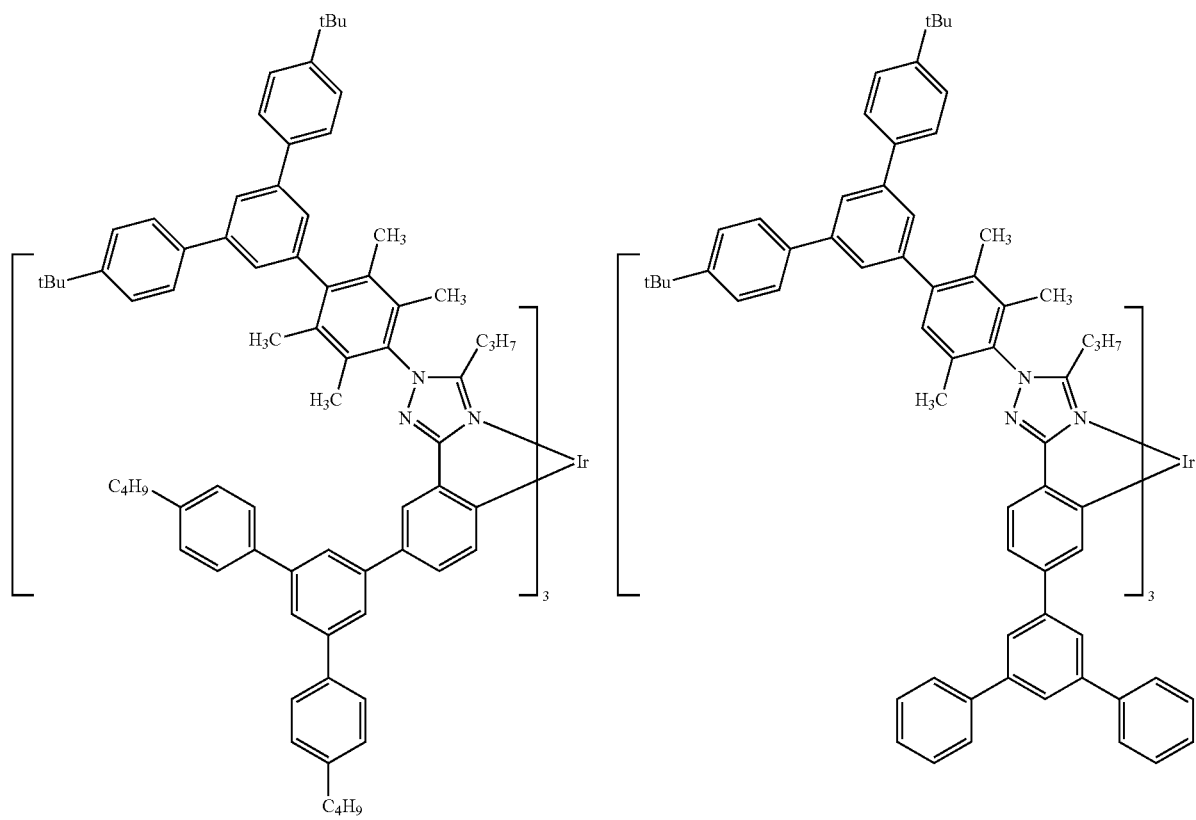
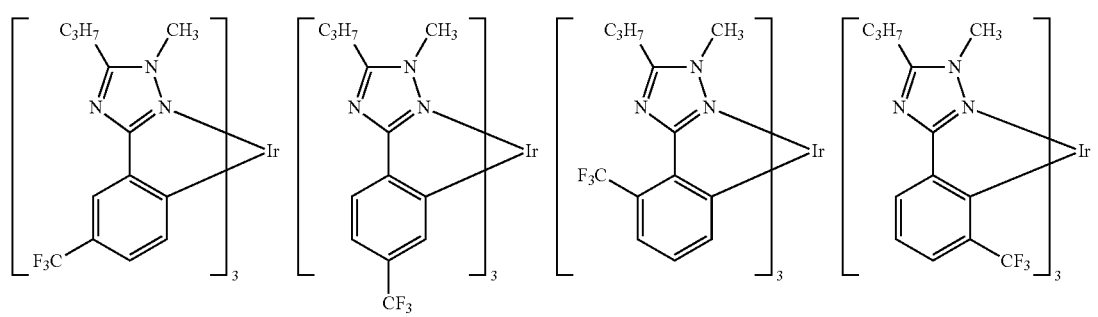
[Chem. 19]
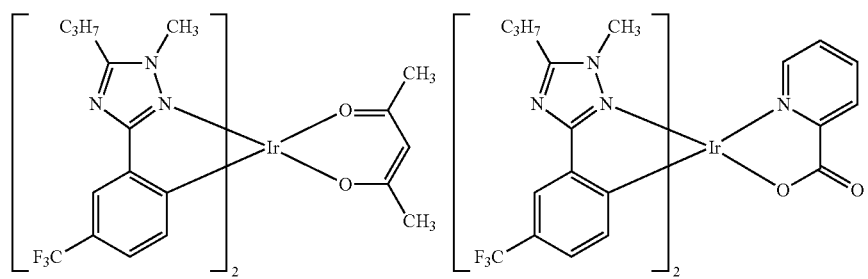

-continued
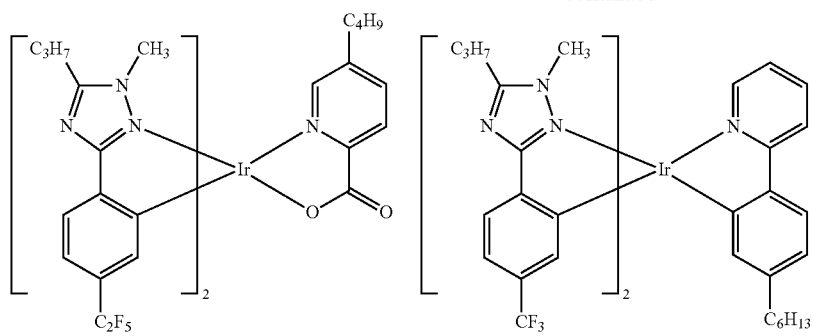
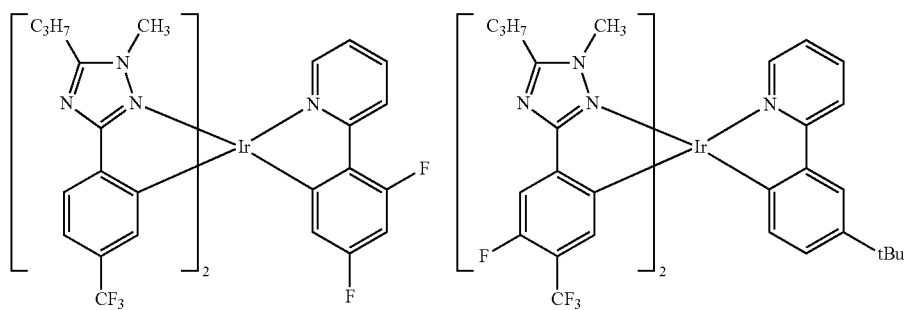
[Chem. 20]
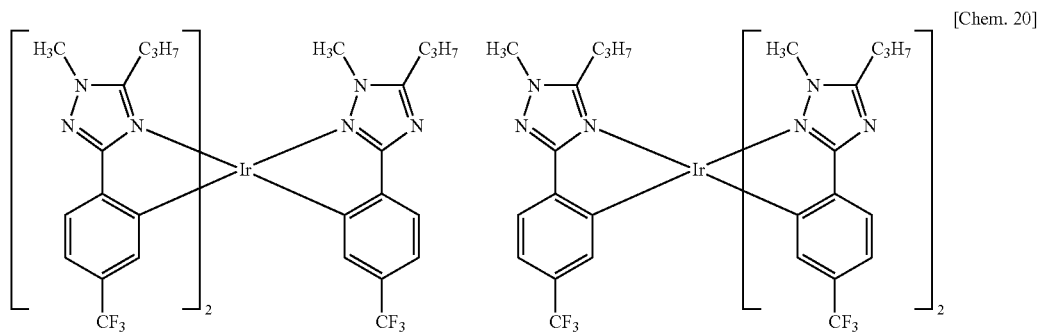
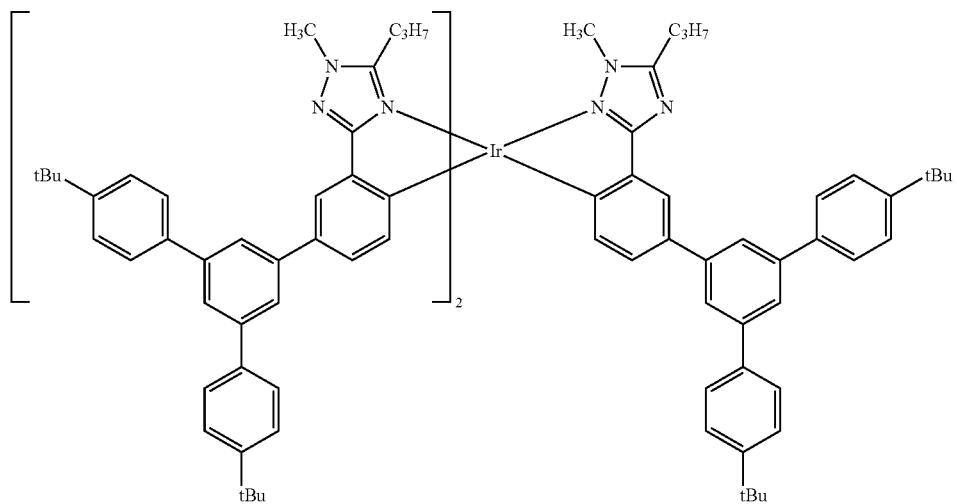

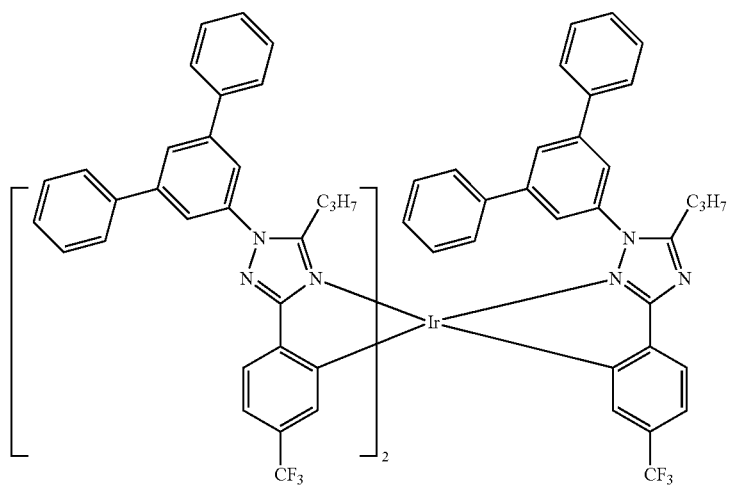
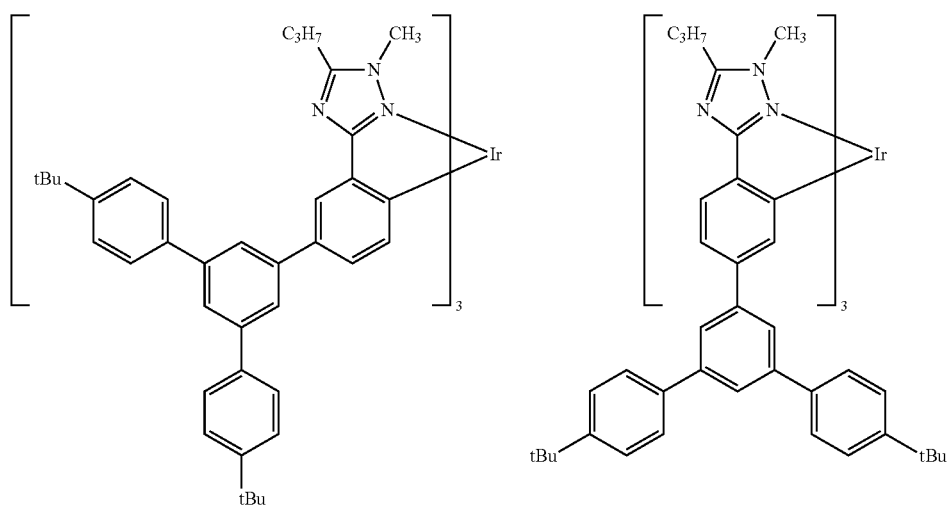
[Chem. 21]
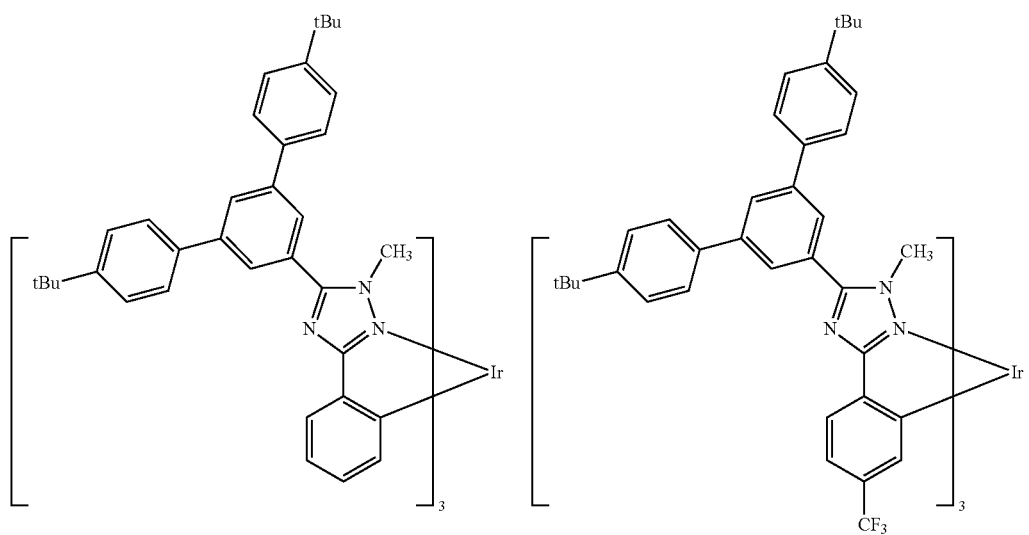

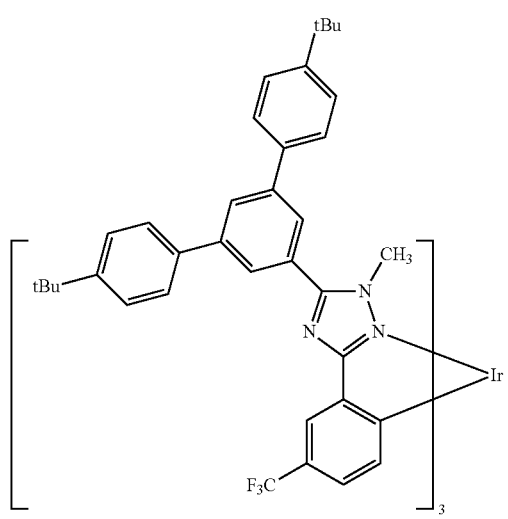
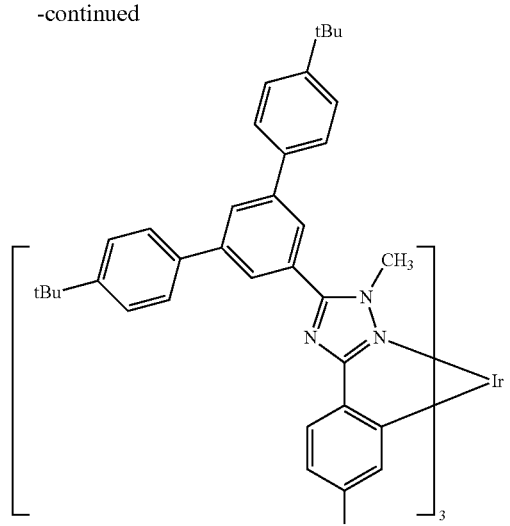
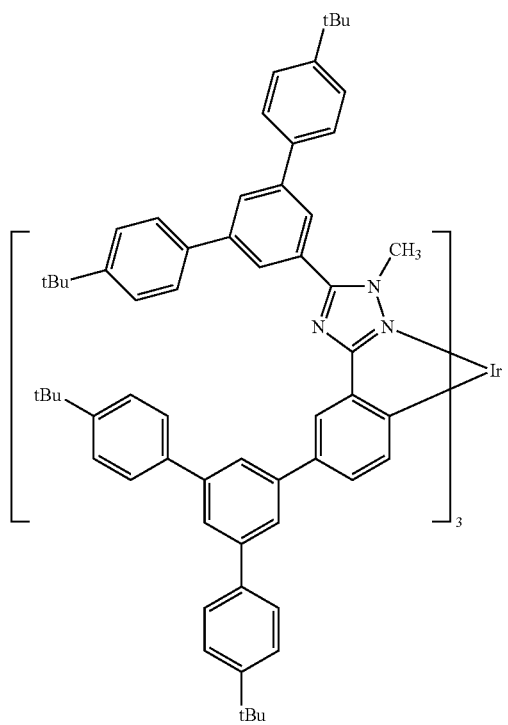
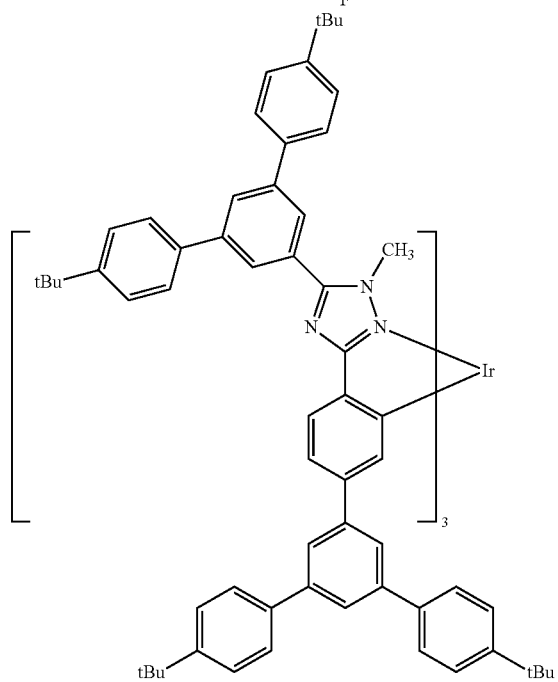

—Method for Manufacturing Metal Complex—

Next, a method for synthesizing the metal complex of the present invention will be described.

The metal complex of the present invention can be synthesized, for example, by reacting a compound to be a ligand with a metal compound in a solvent. If necessary, a base, a silver chloride compound or the like may exist in the reaction system. The metal complex of the present invention can be synthesized by a coupling reaction of a metal complex having a 3-phenyl-1,2,4-triazole derivative as a ligand and an aromatic heterocyclic compound.

The method of complexation (that is, the method for reacting a compound to be a ligand with a metal compound in a solution) include:

in a case of a complex having an iridium atom, methods described in J. Am. Chem. Soc. 1984, 106, 6647; Inorg. Chem. 1991, 30, 1685; Inorg. Chem. 1994, 33, 545; Inorg. Chem. 2001, 40, 1704; Chem. Lett., 2003, 32, 252; and the like, in a case of a complex having a platinum atom, methods described in Inorg. Chem., 1984, 23, 4249; Chem. Mater. 1999, 11, 3709; Organometallics, 1999, 18, 1801; and the like, and in a case of a complex having a palladium atom, methods described in J. Org. Chem., 1987, 52, 73, and the like.

Although a reaction temperature for the complexation is not limited, it is usually between the melting point and the boiling point of a solvent, and preferably from −78° C. to the boiling point of a solvent. Although the reaction time is not limited, it is usually from 30 minutes to 30 hours. When a microwave reaction apparatus is used for the complexation reaction, the reaction can be carried out at the boiling point of a solvent or higher, and although the reaction time is not limited, it is from several minutes to several hours.

The compound to be a ligand can be synthesized, for example, by Suzuki coupling, Grignard coupling, Stille coupling or the like of a 3-phenyl-1,2,4-triazole derivative and an aromatic heterocyclic compound. If necessary, the compound can be synthesized by dissolving reactants in an organic solvent and, for example, reacting them at a temperature of the melting point or higher and the boiling point or lower of the organic solvent, using a base, an appropriate catalyst, etc. For such synthesis, there can be used methods described in, for example: "Organic Syntheses", Collective Volume VI, pp. 407-411, John Wiley & Sons, Inc., 1988; Chem. Rev., vol. 106, p. 2651 (2006); Chem. Rev., vol. 102, p. 1359 (2002); Chem. Rev., vol. 95, p. 2457 (1995); J. Organomet. Chem., vol. 576, p. 147 (1999); and the like.

The aromatic heterocyclic compound can be synthesized by methods described in "HOUBEN-WEYL METHODS OF ORGANIC CHEMISTRY 4$^{TH}$ EDITION", vol. E9b, p. 1 (GEORG THIEME VERLAG STUTTGART); HOUBEN-WEYL METHODS OF ORGANIC CHEMISTRY 4$^{TH}$ EDITION, vol. E9c, p. 667 (GEORG THIEME VERLAG STUTTGART); and the like.

An identification and an analysis of the obtained compound can be performed with CHN elementary analysis, NMR analysis, MS analysis and X-ray crystal structure analysis.

<Composition>

The composition of the present invention contains the metal complex of the present invention and a charge transport compound (that is, charge transport material), and may further contain a light-emitting material.

The charge transport material is classified into a hole transport material and an electron transport material. Specifically, an organic compound (a low molecular compound and/or a polymer compound) can be used for the charge transport material. The charge transport material is preferably a polymer compound.

The hole transport material includes compounds publicly known as hole transport materials for organic electroluminescent device, such as aromatic amines, carbazole derivatives and polyparaphenylene derivatives. The electron transport material includes compounds publicly known as electron transport materials for organic electroluminescent device, for example, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, and metal complexes of 8-hydroxyquinoline and derivatives thereof. The low molecular compound for the charge transport material means a host compound and a charge transport compound used for a low molecular organic electroluminescent device. Specific examples thereof include compounds described in "Organic EL display" (co-authored by Shizuo Tokito, Chihaya Adachi and Hideyuki Murata, Ohmsha, Ltd.) p. 107, "Monthly Display" (vol. 9, No. 9, 2003, pp. 26-30), JP-A-2004-244400, JP-A-2004-277377, and the like. Although depending on the type of the charge transport material, it is generally preferable for obtaining satisfactory light emission from the metal complex that the lowest triplet excitation energy of the charge transport material is higher than the lowest triplet excitation energy of the metal complex.

Specifically, the low molecular compound for the charge transport material may include compounds below.

[Chem. 22]

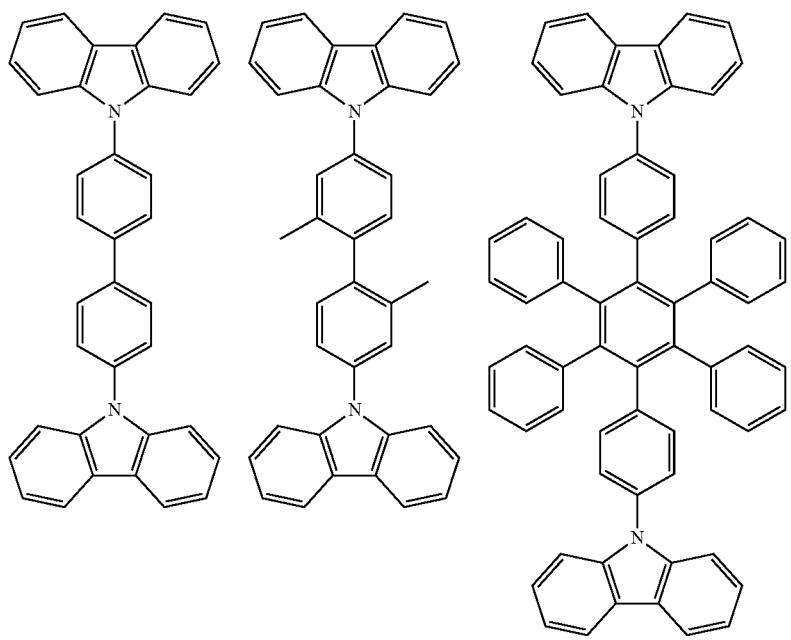

-continued
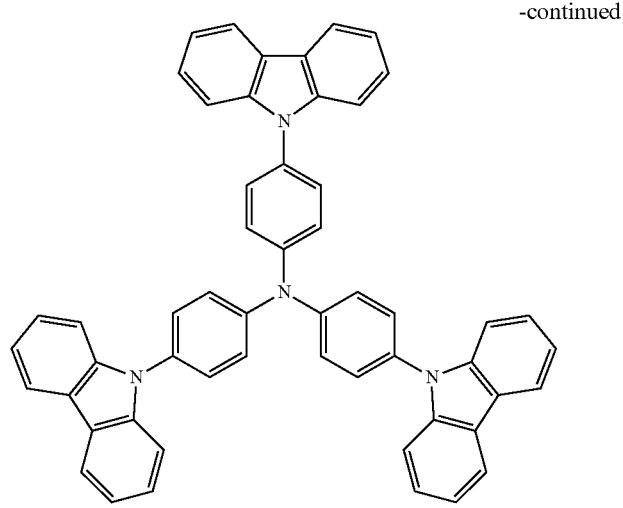
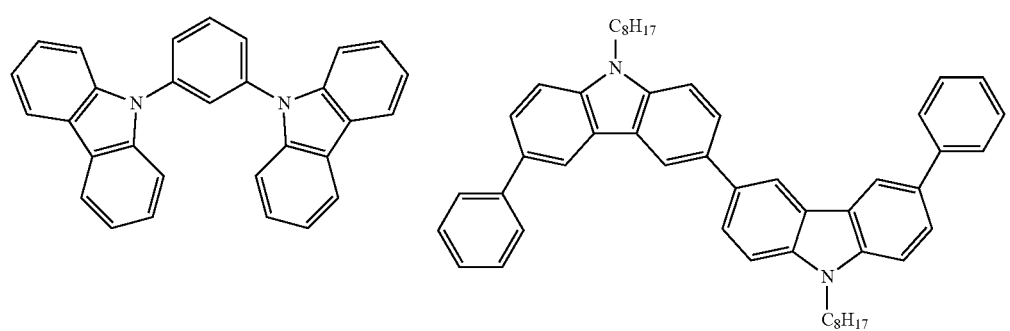
[Chem. 23]
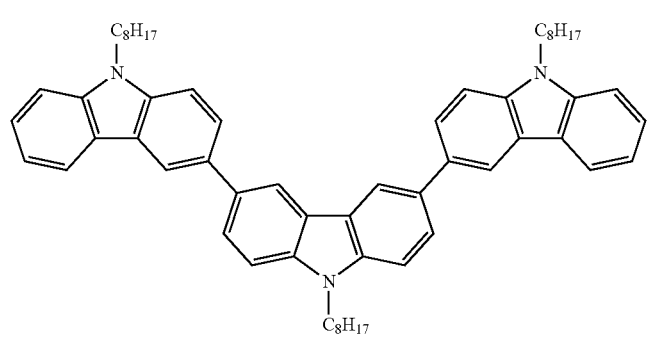
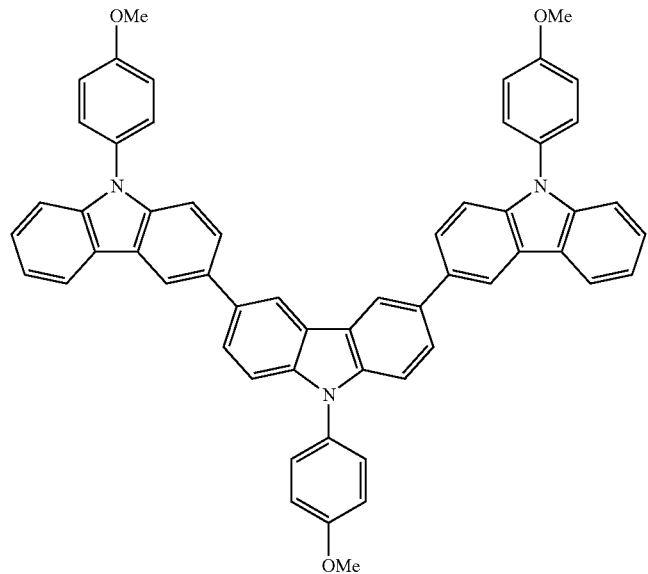

-continued
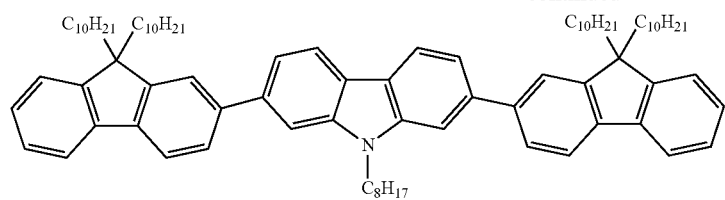
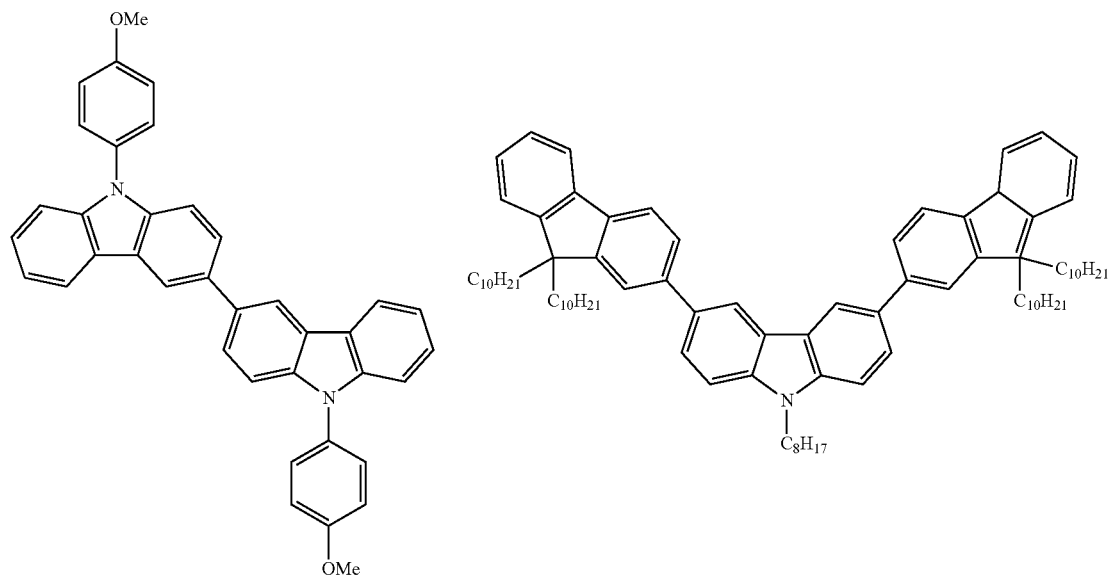
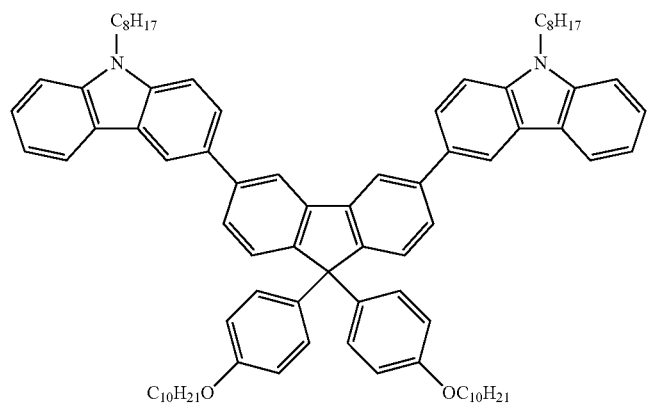
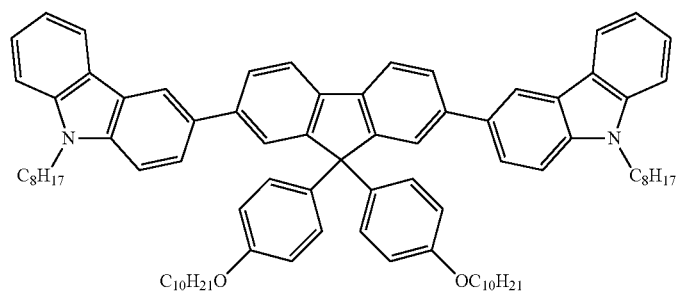

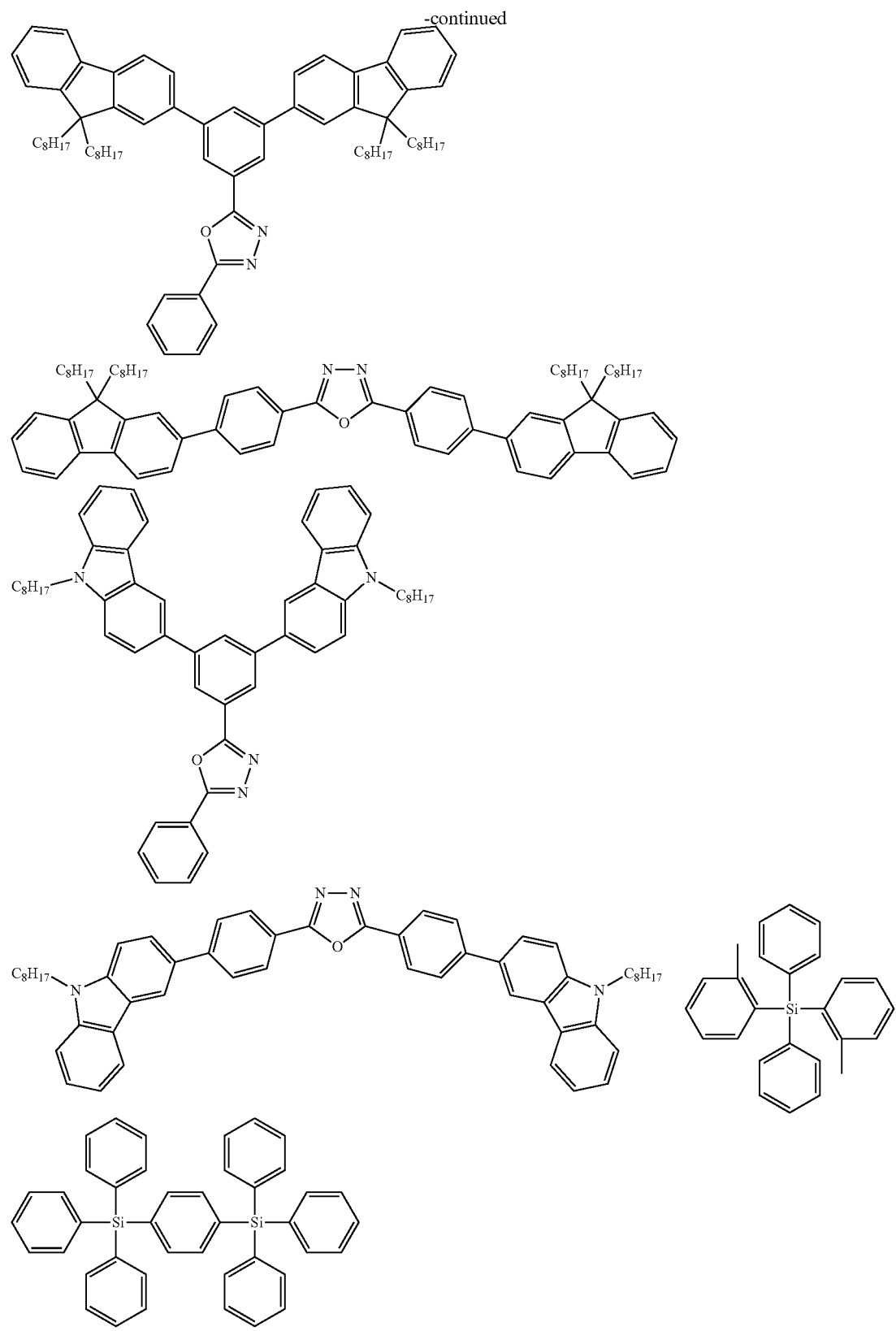
The polymer compound for the charge transport material includes a non-conjugated polymer compound and a conjugated polymer compound. The non-conjugated polymer compound includes polyvinyl carbazole and the like. Examples of the conjugated polymer compound may include polymer compounds containing an aromatic ring in the main chain thereof, such as polymer compounds containing, as a repeating unit in the main chain thereof, a phenylene group optionally having a substituent, a fluorenediyl group optionally having a substituent, a dibenzothiophenediyl group optionally having a substituent, a dibenzofurandiyl group optionally having a substituent, a dibenzosilolediyl group optionally having a substituent or the like; and copolymers of these groups with each other. Specifically, the conjugated polymer compound includes a polymer compound having, as a partial structure of a repeating unit thereof, a benzene ring optionally having a substituent. Other examples thereof include polymer compounds described in, for example, JP-A-2003-231741, JP-A-2004-059899, JP-A-2004-002654, JP-A-2004-292546, U.S. Pat. No. 5,708,130, WO99/54385, WO00/46321, WO02/077060, "Organic EL display" (co-authored by Shizuo Tokito, Chihaya Adachi and Hideyuki Murata, Ohmsha, Ltd.) p. 111, Monthly Display (vol. 9, No. 9, 2002), pp. 47-51, and the like.

The polymer compound for the charge transport material is preferably a polymer compound containing a group represented by Formula (I):

$$—Ar—\quad\quad(I)$$

wherein Ar represents an arylene group, a divalent heterocyclic group or a divalent aromatic amine residue, and these groups may have a substituent.

Examples of the arylene group represented by Ar in Formula (I) include a phenylene group optionally having a substituent, a naphthylene group optionally having a substituent, and a divalent group represented by Formula (4a).

[Chem. 24]

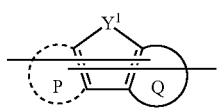

(4a)

In the formula, a ring P and a ring Q each independently represent an aromatic ring, and the ring P may or may not exist. With regard to two bonds, when the ring P exists, two bonds exist on the ring P or the ring Q, or one bond exists on the ring P and another bond exists on the ring Q. When the ring P does not exist, two bonds exist on a 5-membered ring containing $Y^1$ (which may also be a 6-membered ring) or the ring Q, or one bond exists on the 5-membered ring containing $Y^1$ (which may also be a 6-membered ring) and another bond exists on the ring Q. The ring P, the ring Q, and the 5-membered ring containing $Y^1$ (which may also be a 6-membered ring) may each independently have at least one substituent selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group.

$Y^1$ represents $—C(R^{11})(R^{12})—$, $—C(R^{14})(R^{15})—C(R^{16})(R^{17})—$, or $—C(R^{32})=C(R^{33})—$. $R^{11}$, $R^{12}$, $R^{14}$ to $R^{17}$, $R^{32}$ and $R^{33}$ each independently represent a hydrogen atom, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

In Formula (I), an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group which are substituents that the ring P, the ring Q, and the 5-membered ring containing $Y^1$ (which may also be a 6-membered ring) may have are the same as the groups and atoms described and exemplified above as the groups and atoms represented by R.

In Formula (I), an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group and a halogen atom represented by $R^{11}$, $R^{12}$, $R^{14}$ to $R^{17}$, $R^{32}$ and $R^{33}$ are the same as the groups and atoms described and exemplified above as the groups and atoms represented by R.

In Formula (I), the divalent heterocyclic group represented by Ar refers to an atomic group remaining after removing two hydrogen atoms from a heterocyclic compound, and the group may have a substituent. The heterocyclic compound refers to a compound containing not only a carbon atom but also one or more types of atoms selected from the group consisting of an oxygen atom, a nitrogen atom, a silicon atom, a germanium atom, a tin atom, a phosphorus atom, a boron atom, a sulfur atom, a selenium atom and a tellurium atom as an element constituting the ring, among organic compounds having a cyclic structure. Among divalent heterocyclic groups, a divalent aromatic heterocyclic group is preferred. The divalent heterocyclic group has usually 3 to 60 carbon atoms without the number of carbon atoms of the substituent. The total number of carbon atoms of the divalent heterocyclic group including the number of carbon atoms of the substituent is usually 3 to 100.

Examples of the divalent heterocyclic group represented by Ar in Formula (I) include a divalent group represented by Formula (4b).

[Chem. 25]

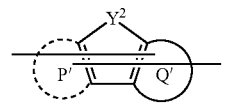

(4b)

In the formula, a ring P' and a ring Q' each independently represent an aromatic ring and the ring P' may or may not exist. With regard to two bonds, when the ring P' exists, two bonds exist on the ring P' or the ring Q', or one bond exists on the ring P' and another bond exists on the ring Q. When the ring P' does not exist, two bonds exist on a 5-membered ring containing $Y^2$ (which may also be a 6-membered ring)

or the ring Q', or one bond exists on the 5-membered ring containing $Y^2$ (which may also be a 6-membered ring) and another bond exists on the ring Q'. The ring P', the ring Q', and the 5-membered ring containing $Y^2$ (which may also be a 6-membered ring) may each independently have at least one substituent selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group.

$Y^2$ represents —O—, —S—, —Se—, —B($R^6$)—, —Si($R^7$)($R^8$)—, —P($R^9$)—, —$PR^{10}$(=O)—, —N($R^{13}$)—, —O—C($R^{18}$)($R^{19}$)—, —S—C($R^{20}$)($R^{21}$)—, —N—C($R^{22}$)($R^{23}$)—, —Si($R^{24}$)($R^{25}$)—C($R^{26}$)($R^{27}$)—, —Si($R^{28}$)($R^{29}$)—Si($R^{30}$)($R^{31}$)—, —N=C($R^{34}$)—, or —Si($R^{35}$)=C($R^{36}$)—. $R^6$ to $R^{10}$, $R^{13}$, $R^{18}$ to $R^{31}$ and $R^{34}$ to $R^{36}$ each independently represent a hydrogen atom, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

In the formula, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group which are substituents that the ring P', the ring Q', and the 5-membered ring containing $Y^2$ (which may also be a 6-membered ring) may have are the same as the groups and atoms described and exemplified above as the groups and atoms represented by R.

In the formula, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group and a halogen atom represented by $R^6$ to $R^{10}$, $R^{13}$, $R^{18}$ to $R^{31}$ and $R^{34}$ to $R^{36}$ are the same as those described and exemplified above as the groups represented by R.

In Formula (I), the divalent aromatic amine residue represented by Ar means an atomic group remaining after removing two hydrogen atoms from an aromatic amine. The divalent aromatic amine residue has usually 5 to 100 carbon atoms, and preferably 15 to 60 carbon atoms. The number of carbon atoms of the divalent aromatic amine residue does not include the number of carbon atoms of the substituent.

Examples of the divalent aromatic amine residue represented by Ar in Formula (I) include a divalent group represented by Formula (6):

[Chem. 26]

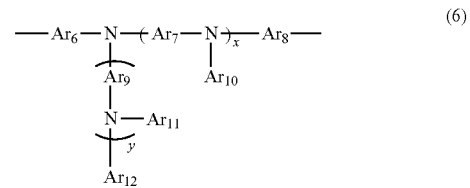

wherein $Ar_6$, $Ar_7$, $Ar_8$ and $Ar_9$ each independently represent an arylene group or a divalent heterocyclic group, $Ar_{10}$, $Ar_{11}$ and $Ar_{12}$ each independently represent an aryl group or a monovalent heterocyclic group, and $Ar_6$ to $Ar_{12}$ may have a substituent; and x and y are each independently 0 or 1.

In Formula (6), the arylene group represented by $Ar_6$ to $Ar_9$ is an atomic group remaining after removing two hydrogen atoms from an aromatic hydrocarbon. The arylene group also includes a group having a fused ring and a group in which two or more selected from among an independent benzene ring and a fused ring are bonded with each other either directly or through a group such as a vinylene group. The arylene group may have a substituent. The arylene group has usually 6 to 60 carbon atoms, and preferably 6 to 20 carbon atoms without the number of carbon atoms of the substituent. The total number of carbon atoms of the arylene group including the number of carbon atoms of the substituent is usually 6 to 100.

In Formula (6), the divalent heterocyclic group represented by $Ar_6$ to $Ar_9$ is the same as the group described and exemplified above as the divalent heterocyclic group represented by Ar.

In Formula (6), the aryl group and the monovalent heterocyclic group represented by $Ar_{10}$ to $Ar_{12}$ are the same as the groups described and exemplified above as the aryl group and the monovalent heterocyclic group represented by R.

In Formula (6), the substituent that the arylene group, the divalent heterocyclic group, the aryl group and the monovalent heterocyclic group may have includes an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group, a cyano group and a nitro group. These substituents are the same as the groups and atoms described and exemplified above as the groups and atoms represented by R.

Examples of the groups represented by Formula (4a) and Formula (4b) include a group represented by Formula (4-1), Formula (4-2) or Formula (4-3):

[Chem. 27]

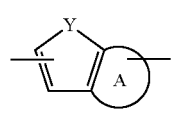

Formula (4-1)

-continued

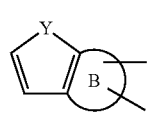
Formula (4-2)

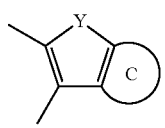
Formula (4-3)

wherein a ring A, a ring B and a ring C each independently represent an aromatic ring;

Y represents the same meaning as $Y^1$ or the same meaning as $Y^2$;

the ring A, the ring B, the ring C and a 5-membered ring containing Y (which may also be a 6-membered ring) may each independently have one or more substituents selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group; and a group represented by Formula (4-4) or Formula (4-5):

[Chem. 28]

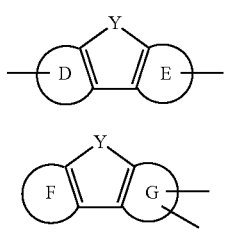

Formula (4-4)

Formula (4-5)

wherein a ring D, a ring E, a ring F and a ring G each independently represent an aromatic ring;

Y represents the same meaning as $Y^1$ or the same meaning as $Y^2$;

the ring D, the ring E, the ring F, the ring G and a 5-membered ring containing Y (which may also be a 6-membered ring) may each independently have one or more substituents selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group.

Among them, a group represented by Formula (4-4) or Formula (4-5) is preferred.

In Formula (4-1) to Formula (4-5), Y is preferably —S—, —O—, —C($R^{11}$) ($R^{12}$)— or —N($R^{13}$)—, and more preferably —S—, —O— or —N($R^{13}$)— from the viewpoint of the luminous efficiency of the light-emitting device manufactured using the composition of the present invention.

Examples of the aromatic rings in Formulae (4-1) to (4-5) include: aromatic rings such as a benzene ring, a naphthalene ring, an anthracene ring, a tetracene ring, a pentacene ring, a pyrene ring and a phenanthrene ring; and aromatic heterocyclic rings such as a pyridine ring, a bipyridine ring, a phenanthroline ring, a quinoline ring, an isoquinoline ring, a thiophene ring, a furan ring and a pyrrole ring.

As the substituent that the groups represented by Formulae (4-1) to (4-5) may have, preferred is an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, an acyloxy group, an imine residue, a carbamoyl group, an amido group, an acid imido group, a monovalent heterocyclic group, a carboxyl group and a substituted carboxyl group, and more preferred is an alkyl group, an alkyloxy group, an aryl group and a monovalent heterocyclic group.

The polymer compound for the charge transport material is, for example, a polymer compound containing a group among the following (that is, a group in parentheses in the following examples), and particularly preferably a polymer compound containing a group among the following as a repeating unit.

[Chem. 29]

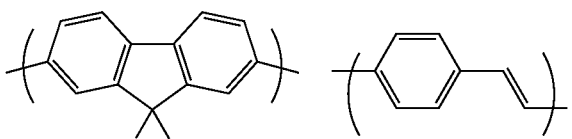

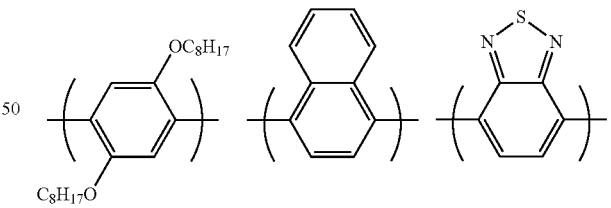

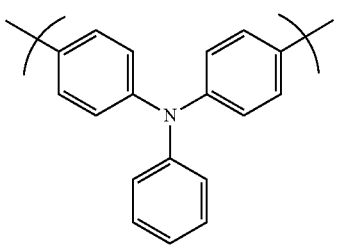

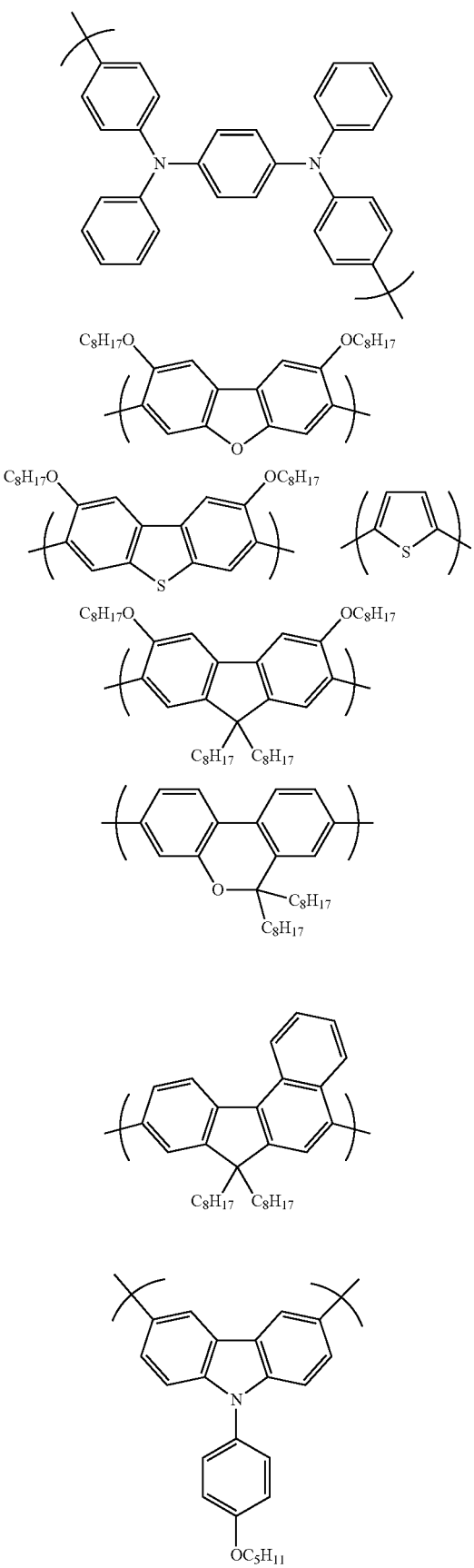

The lowest triplet excitation energy of the low molecular compound or polymer compound for the charge transport material (TH) and the lowest triplet excitation energy of the metal complex of the present invention (TM) satisfy: preferably a relation of $TH>TM-0.1$ (eV);

more preferably a relation of $TH>TM$; and further preferably a relation of $TH>TM+0.1$ (eV).

When using the polymer compound for the charge transport material, the polymer compound has a polystyrene-equivalent number average molecular weight of preferably $10^3$ to $10^8$, and more preferably $10^4$ to $10^6$. The polymer compound has a polystyrene-equivalent weight average molecular weight of preferably $10^3$ to $10^8$, and more preferably $5\times10^4$ to $5\times10^6$.

For the light-emitting material, a publicly known light-emitting material can be used. Examples thereof include low molecular light-emitting materials such as naphthalene derivatives; anthracene and derivatives thereof; perylene and derivatives thereof; dyes such as polymethine-based, xanthene-based, coumarin-based and cyanine-based dyes; metal complexes of 8-hydroxyquinoline and derivatives thereof; aromatic amines; tetraphenylcyclopentadiene and derivatives thereof; and tetraphenylbutadiene and derivatives thereof.

The amount of the metal complex of the present invention in the composition of the present invention is usually 0.1 to 80 parts by weight, preferably 0.1 to 60 parts by weight, and more preferably 0.1 to 40 parts by weight, when the total amount of the composition of the present invention is defined as 100 parts by weight. The metal complexes of the present invention may be used alone or in combination of two or more types thereof.

<Light-Emitting Device>

One embodiment of the light-emitting device of the present invention is a device including: a pair of electrodes composed of an anode and a cathode; and a film composed of a single layer (monolayer type) or a plurality of layers (multilayer type) between the electrodes, wherein the film includes at least a light-emitting layer. At least one layer of the film layer contains the metal complex of the present invention. The content of the metal complex of the present invention in the film is usually 0.1 to 100% by weight, preferably 0.1 to 80% by weight, more preferably 0.1 to 60% by weight, and further preferably 0.1 to 40% by weight, based on the total weight of the light-emitting layer. In the light-emitting device of the present invention, it is preferable that the light-emitting layer contains the metal complex of the present invention as the light-emitting material.

When the light-emitting device of the present invention is of the monolayer type, the film is the light-emitting layer and the light-emitting layer contains the metal complex of the present invention. When the light-emitting device of the present invention is of the monolayer type or the multilayer type, the light-emitting device takes, for example, the following layer configurations:

a) Anode/Light-emitting layer/Cathode
b) Anode/Hole transport layer/Light-emitting layer/Cathode
c) Anode/Light-emitting layer/Electron transport layer/Cathode
d) Anode/Hole transport layer/Light-emitting layer/Electron transport layer/Cathode
e) Anode/Charge injection layer/Light-emitting layer/Cathode
f) Anode/Light-emitting layer/Charge injection layer/Cathode
g) Anode/Charge injection layer/Light-emitting layer/Charge injection layer/Cathode
h) Anode/Charge injection layer/Hole transport layer/Light-emitting layer/Cathode
i) Anode/Hole transport layer/Light-emitting layer/Charge injection layer/Cathode
j) Anode/Charge injection layer/Hole transport layer/Light-emitting layer/Charge injection layer/Cathode
k) Anode/Charge injection layer/Light-emitting layer/Charge transport layer/Cathode
l) Anode/Light-emitting layer/Electron transport layer/Charge injection layer/Cathode
m) Anode/Charge injection layer/Light-emitting layer/Electron transport layer/Charge injection layer/Cathode
n) Anode/Charge injection layer/Hole transport layer/Light-emitting layer/Charge transport layer/Cathode
o) Anode/Hole transport layer/Light-emitting layer/Electron transport layer/Charge injection layer/Cathode
p) Anode/Charge injection layer/Hole transport layer/Light-emitting layer/Electron transport layer/Charge injection layer/Cathode The symbol "/" indicates that the layers are stacked adjacent to each other. The same shall apply hereinafter.

The anode of the light-emitting device of the present invention is an electrode for supplying holes to the hole injection layer, the hole transport layer, the light-emitting layer, and the like. It is effective that the anode has a work function of 4.5 eV or more. As a material for the anode, a metal, an alloy, a metal oxide, an electroconductive compound, a mixture thereof, and the like can be used. Specifically, the material includes: conductive metal oxides such as tin oxide, zinc oxide, indium oxide and indium-tin-oxide (ITO); metals such as gold, silver, chromium and nickel; a mixture or a layered product of the conductive metal oxide and the metal; inorganic conductive substances such as copper iodide and copper sulfide; organic conductive materials such as polyanilines, polythiophenes (such as PEDOT), and polypyrroles; and a layered product of these with ITO.

The cathode of the light-emitting device of the present invention is an electrode for supplying electrons to the electron injection layer, the electron transport layer, the light-emitting layer, and the like. As a material for the cathode, a metal, an alloy, a metal halide, a metal oxide, an electroconductive compound, and a mixture thereof can be used. Examples of the material for the cathode include alkali metals (such as lithium, sodium and potassium) and fluorides and oxides thereof; alkaline earth metals (such as magnesium, calcium, barium and cesium) and fluorides and oxides thereof; gold, silver, lead, aluminum, and alloys and mixed metals (such as a sodium-potassium alloy, a sodium-potassium mixed metal, a lithium-aluminum alloy, a lithium-aluminum mixed metal, a magnesium-silver alloy and a magnesium-silver mixed metal); and rare earth metals (such as indium and ytterbium).

The hole injection layer and the hole transport layer of the light-emitting device of the present invention are layers that have only to have any one of a function of injecting holes from the anode, a function of transporting holes, and a function of blocking electrons injected from the cathode. As a material for these layers, a publicly known material can be appropriately selected and used. Examples thereof include carbazole derivatives, triazole derivatives, oxazole derivatives, oxadiazole derivatives, imidazole derivatives, polyaryl alkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, polysilane-based compounds, poly(N-vinylcarbazole) derivatives, organic silane derivatives, the metal complex of the present invention, and polymers containing these compounds. Other examples thereof include: aniline-based copolymers; and conductive polymers and oligomers such as thiophene oligomer and polythiophene. These materials may be used alone or in combination of two or more types thereof. The hole injection layer and the hole transport layer may have either a monolayer structure composed of one type or two or more types of the above materials or a multilayer structure composed of a plurality of layers having the same composition or different compositions.

The electron injection layer and the electron transport layer of the light-emitting device of the present invention are layers that have only to have any one of a function of injecting electrons from the cathode, a function of transporting electrons, and a function of blocking holes injected from the anode. As a material for these layers, a publicly known material can be appropriately selected and used. Examples thereof include triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidene methane derivatives, distyrylpyrazine derivatives, tetracarboxylic anhydrides of aromatic ring such as naphthalene and perylene, phthalocyanine derivatives, various metal complexes typified by metal complexes of 8-quinolinol derivatives, metal phthalocyanines and a metal complex having benzoxazole or benzothiazole as a ligand, organic silane derivatives, and the metal complex compound of the present invention. The electron injection layer and the electron transport layer may have either a monolayer structure composed of one type or two or more types of the above materials or a multilayer structure composed of a plurality of layers having the same composition or different compositions.

In the light-emitting device of the present invention, an inorganic compound that is an insulator or a semiconductor can also be used as the material for the electron injection layer and the electron transport layer. When the electron injection layer and the electron transport layer are formed of an insulator or a semiconductor, a leak of current can be effectively prevented to enhance electron injecting property. For such insulator, there can be used at least one metal compound selected from the group consisting of alkali metal chalcogenides, alkaline earth metal chalcogenides, alkali metal halides and alkaline earth metal halides. Preferred examples of alkali metal chalcogenides include CaO, BaO, SrO, BeO, BaS and CaSe. The semiconductor that constitutes the electron injection layer and the electron transport layer includes oxides, nitrides and oxide-nitrides containing at least one element selected from the group consisting of Ba, Ca, Sr, Yb, Al, Ga, In, Li, Na, Cd, Mg, Si, Ta, Sb and Zn. These oxides, nitrides and oxide-nitrides may be used alone or in combination of two or more types thereof.

In the present invention, a reductive dopant may be added to an interface region between the cathode and a film in contact with the cathode. The reductive dopant is preferably at least one compound selected from the group consisting of alkali metals, oxides of alkaline earth metals, alkaline earth metals, rare-earth metals, oxides of alkali metals, halides of alkali metals, oxides of alkaline earth metals, halides of alkaline earth metals, oxides of rare-earth metals, halides of rare-earth metals, complexes of alkali metals, complexes of alkaline earth metals and complexes of rare-earth metals.

The light-emitting layer of the light-emitting device of the present invention is a layer having a function of capable of injecting holes from the anode, the hole injection layer or the hole transport layer and capable of injecting electrons from the cathode, the electron injection layer or the electron transport layer when the electric field is applied; a function of moving the injected charges (electrons and holes) by the force of the electric field; and a function of providing a site where electrons and holes are recombined and thereby leading to light emission. The light-emitting layer of the light-emitting device of the present invention preferably contains the metal complex of the present invention, and may also contain a host material such that the metal complex serves as a guest material. The host material includes the charge transport materials noted above. A light-emitting layer in which the light-emitting material is doped in the host material can be formed, for example, by mixing the host material and the light-emitting material such as the metal complex and applying the mixture, or by conducting co-evaporation of the host material and the light-emitting material.

In the light-emitting device of the present invention, the method for forming each of the layers is not particularly limited and publicly known methods can be used. Specifically, the method includes a vacuum deposition method (such as a resistance heating deposition method and an electron beam method), a sputtering method, an LB method, a molecular layering method, and an application method (such as a casting method, a spin coating method, a bar coating method, a blade coating method, a roll coating method, a gravure printing method, a screen printing method and an inkjet printing method). Among them, the application method is preferred because the manufacturing step could be simplified. In the applying method, each layer can be formed by: dissolving the metal complex of the present invention into a solvent to prepare an applying liquid; applying the applying liquid onto a desired layer (or electrode); and drying the liquid. The applying liquid may contain a resin as a host material and/or a binder. The resin may be present in a solvent either in a dissolved state or in a dispersed state. Depending on purposes, the resin can be selected from among polyvinyl chloride, a polycarbonate, polystyrene, polymethyl methacrylate, polybutyl methacrylate, a polyester, a polysulfone, polyphenylene oxide, polybutadiene, poly(N-vinylcarbazole), a hydrocarbon resin, a ketone resin, a phenyloxy resin, a polyamide, ethyl cellulose, vinyl acetate, an ABS resin, polyurethane, a melamine resin, an unsaturated polyester resin, an alkyd resin, an epoxy resin, a silicone resin, and the like. Depending on purposes, the solution may contain an antioxidant, a viscosity control agent, and the like as an optional component.

<Photoelectric Device>

The metal complex of the present invention can be used for the manufacture of a photoelectric device.

Examples of the photoelectric device include a photoelectric conversion device, specifically, a device in which a layer containing the metal complex of the present invention is disposed between two electrodes at least one of which is transparent or semi-transparent, a device in which an interdigital electrode is formed on a layer that contains the metal complex of the present invention and that is provided as a film on a substrate. For enhancing the characteristics, there may be blended fullerene, carbon nanotube, and the like.

The method for manufacturing the photoelectric conversion device includes a method disclosed in Japanese Patent No. 3146296. Specific examples thereof include a method that involves forming a layer (film) containing the metal complex of the present invention on a substrate having a first electrode and forming a second electrode on the layer, and a method that involves forming a layer (film) containing the metal complex of the present invention on a pair of interdigital electrodes formed on a substrate. Either of the first electrode or the second electrode is transparent or semi-transparent.

Although the method for forming the layer (film) containing the metal complex of the present invention and the method for blending fullerene or carbon nanotube are not particularly limited, the method shown as an example with respect to the light-emitting device can be suitably used.

<Liquid Composition>

The liquid composition of the present invention contains the metal complex of the present invention and a solvent or dispersion medium. As the solvent or dispersion medium used for the liquid composition of the present invention, a solvent or dispersion medium that is capable of homogeneously dissolving or dispersing the component of the film and that is stable can be appropriately selected for use from publicly known solvents. Such a solvent includes chlorine-based solvents (such as chloroform, methylene chloride, 1,2-dichloroethane, 1,1,2-trichloroethane, chlorobenzene and o-dichlorobenzene), ether solvents (such as tetrahydrofuran and dioxane), aromatic hydrocarbon solvents (such as benzene, toluene and xylene), aliphatic hydrocarbon solvents (such as cyclohexane, methylcyclohexane, n-pentane, n-hexane, n-heptane, n-octane, n-nonane and n-decane), ketone solvents (such as acetone, methyl ethyl ketone and cyclohexanone), ester solvents (such as ethyl acetate, butyl acetate and ethylcellosolve acetate), polyhydric alcohols and derivatives thereof (such as ethylene glycol, ethylene glycol monobutyl ether, ethylene glycol monoethyl ether, ethylene glycol monomethyl ether, di(methyloxy)ethane, propylene glycol, di(ethyloxy)methane, triethylene glycol monoethyl ether, glycerin and 1,2-hexanediol), alcohol solvents (such as methanol, ethanol, propanol, isopropanol and cyclohexanol), sulfoxide solvents (such as dimethylsulfoxide), and amide solvents (such as N-methyl-2-pyrrolidone and N,N-dimethylformamide). These solvents may be used alone or in combination of two or more types thereof.

When the liquid composition is applied to an inkjet method, the liquid composition may contain a publicly known additive for favorable discharge properties of the liquid composition and reproducibility thereof. The publicly known additive includes a solvent having a high boiling point (such as anisole and bicyclohexylbenzene) for suppressing evaporation through a nozzle. The liquid composition comprising the publicly known additive preferably has a viscosity at 25° C. of 1 to 100 mPa·s.

A preferred thickness of each layer of the light-emitting device of the present invention varies depending on the type of material and the layer configuration and is not particularly limited. Generally, too small thickness of layer tends to cause a defect such as a pinhole and too large thickness requires a high applied voltage, leading to low luminous efficiency. Thus, it is usually preferable that the thickness is from several nm to 1 μm.

The use application of the light-emitting device of the present invention includes, but is not limited to, a planar light source, a light source for illumination apparatus (or a light source), a light source for a signal, a light source for a backlight, a display device, a printer head, and the like. In the display device, configurations such as a segment-type and a dot matrix-type can be selected by using a publicly known driving technology, driving circuit, and the like.

<Other Use Applications>

The metal complex of the present invention is not only useful for the manufacture of the light-emitting device, but also can be used, for example, as a semiconductor material such as an organic semiconductor material, a light-emitting material, an optical material and a conductive material (for example, the metal complex is applied by doping). Accordingly, the metal complex can be used to manufacture a film (that is, a film containing the metal complex) such as a light-emitting film, a conductive film and an organic semiconductor film.

The metal complex of the present invention can be formed into a conductive film and a semiconductor film by the same method as the method for manufacturing a light-emitting film used for the light-emitting layer of the light-emitting device. Either larger one of the electron mobility or the hole mobility of the semiconductor film is preferably $10^{-5}$ cm$^2$/V/sec or more. The organic semiconductor film can be suitably used for an organic solar cell, an organic transistor, and the like.

EXAMPLES

The present invention will be described in more detail below with reference to Examples, but it should not be construed that the present invention is limited to these Examples.

Example 1: Synthesis of Compound (MC-1)

[Chem. 30]

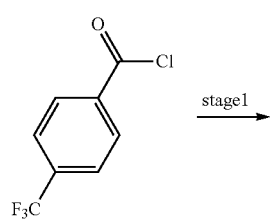

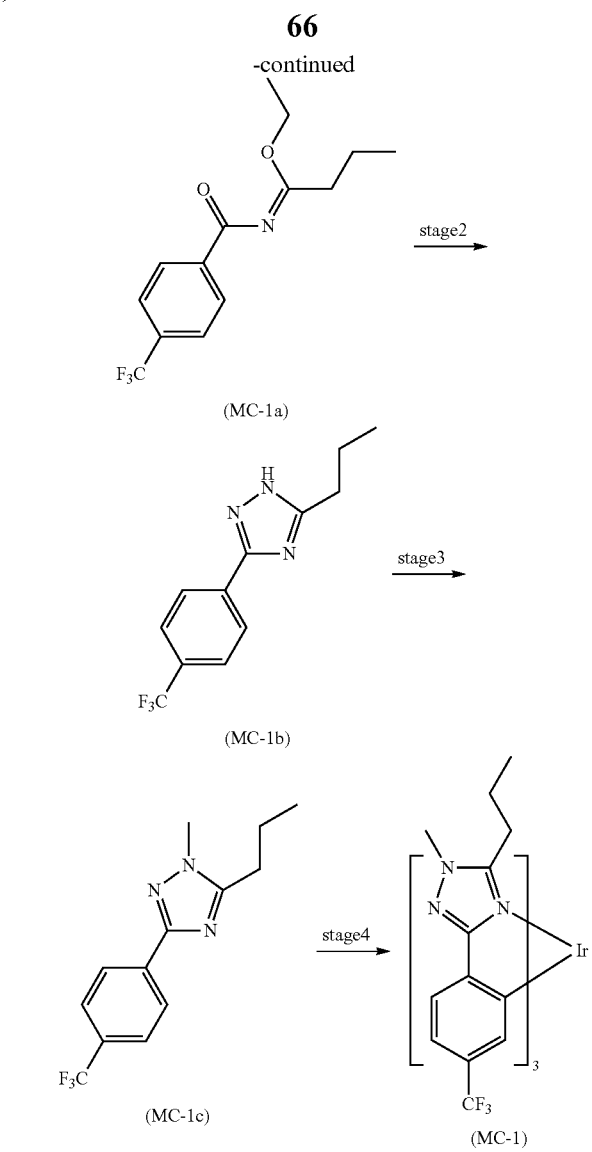

<Stage 1>

Six point two (6.2) grams (30 mmol) of 4-trifluoromethylbenzoyl chloride and 4.5 g (30 mmol) of ethyl butyrimidate hydrochloride were weighed and dissolved in 300 mL of chloroform, and the resultant was placed under a nitrogen atmosphere. Thereafter, 25 mL of a chloroform solution of 8.4 mL (60 mmol) of triethylamine was added dropwise thereto and the resultant was stirred at room temperature under a nitrogen atmosphere. After 15 hours, chloroform as a solvent was concentrated and the concentrate was suspended in 200 mL of water, followed by extracting the resultant with dichloromethane. The resultant solution was concentrated under reduced pressure, thus obtaining 8.0 g (28 mmol) of a compound (MC-1a) as a light yellow liquid.

<Stage 2>

Into 60 mL of chloroform, 3.0 g (10 mmol) of the compound (MC-1a) was dissolved and the resultant was placed under a nitrogen atmosphere. Thereto, 0.55 mL (11 mmol) of hydrazine hydrate was added dropwise under a nitrogen atmosphere at room temperature. After the dropwise addition, the resultant was stirred under a nitrogen atmosphere at room temperature for 17 hours and then 50 mL of water was added therein to quench the reaction. The reaction liquid was transferred into a separating funnel and was washed with water, followed by recovering and concentrating an oil layer. The obtained crude product was recrystallized from a mixed solvent of toluene-hexane, thus obtaining 2.1 g of a compound (MC-1b) as a white solid in a yield of 82%. The result of the $^1$H-NMR analysis is shown below.

$^1$H-NMR (400 MHz/CDCl$_3$): δ (ppm) 8.15 (d, 2H), 7.66 (d, 2H), 2.78 (t, 2H), 1.82 (m, 2H), 0.94 (t, 3H).

<Stage 3>

Two point four (2.4) grams (9.2 mmol) of the compound (MC-1b) and 2.3 g (41 mmol) of potassium hydroxide were weighed and thereto, 35 mL of acetone was poured, followed by placing the inside of the reaction system under a nitrogen atmosphere. Thereto, 1.28 g (9.0 mmol) of methyl iodide was added, and the resultant was stirred under a nitrogen atmosphere at room temperature for 1 hour. After the completion of the reaction, a precipitate was subjected to suction filtration and acetone was removed therefrom. The resultant was dissolved in dichloromethane and then passed through a silica gel column to be purified using a mixed solvent of dichloromethane-ethyl acetate. The obtained eluate was recovered and concentrated, thus obtaining 1.33 g (4.9 mmol) of a compound (MC-1c) as a yellow white solid in a yield of 54%. The result of the $^1$H-NMR analysis is shown below.

$^1$H-NMR (400 MHz/CDCl$_3$): δ (ppm) 8.16 (d, 2H), 7.66 (d, 2H), 3.87 (s, 3H), 2.77 (t, 2H), 1.88-1.81 (m, 2H), 1.05 (t, 3H).

<Stage 4>

Four hundred forty (440) milligrams (1.2 mmol) of iridium chloride and 700 mg (2.6 mmol) of the compound (MC-1c) were weighed and thereto, 20 mL of 2-ethyloxyethanol and 6.5 mL of water were added. The resultant was placed under a nitrogen atmosphere and was heated and refluxed for 14 hours. After cooling down, the reaction liquid was concentrated. To the residue, water and dichloromethane were added to wash the resultant oil layer with water. The oil layer was recovered, and was concentrated and dried to obtain 900 mg of a yellow brown solid. Then, 900 mg of the yellow brown solid and 1.7 g (6.2 mmol) of the compound (MC-1c) were weighed and thereto, 600 mg (2.4 mmol) of silver trifluoromethanesulfonate was added, followed by replacing the inside of the reaction system with argon. The resultant was heated for reaction at 165° C. for 18 hours and was left to be cooled down, and thereto, 15 mL of dichloromethane was poured. The suspension was subjected to suction filtration and then passed through an alumina column to be separated and purified using a mixed solvent of dichloromethane-ethyl acetate, thus obtaining 900 mg (0.90 mmol) of a compound (MC-1) [fac-tris(1-methyl-3-(4-trifluoromethylphenyl)-5-propyl-1H-[1,2,4]-triazolato-N,C2') iridium (III)] as yellow powder in a yield of 65%. The identification of the product was performed using the $^1$H-NMR analysis and the X-ray crystal structure analysis. The result of the $^1$H-NMR analysis is shown below.

$^1$H-NMR (400 MHz/CD$_2$Cl$_2$): δ (ppm) 7.57 (d, 3H), 7.01 (d, 3H), 6.62 (s, 3H), 3.71 (s, 9H), 2.20-1.98 (m, 6H), 1.23-1.13 (m, 3H), 0.90-0.78 (m, 3H), 0.56 (t, 9H).

Example 2: Synthesis of Compound (MC-2)

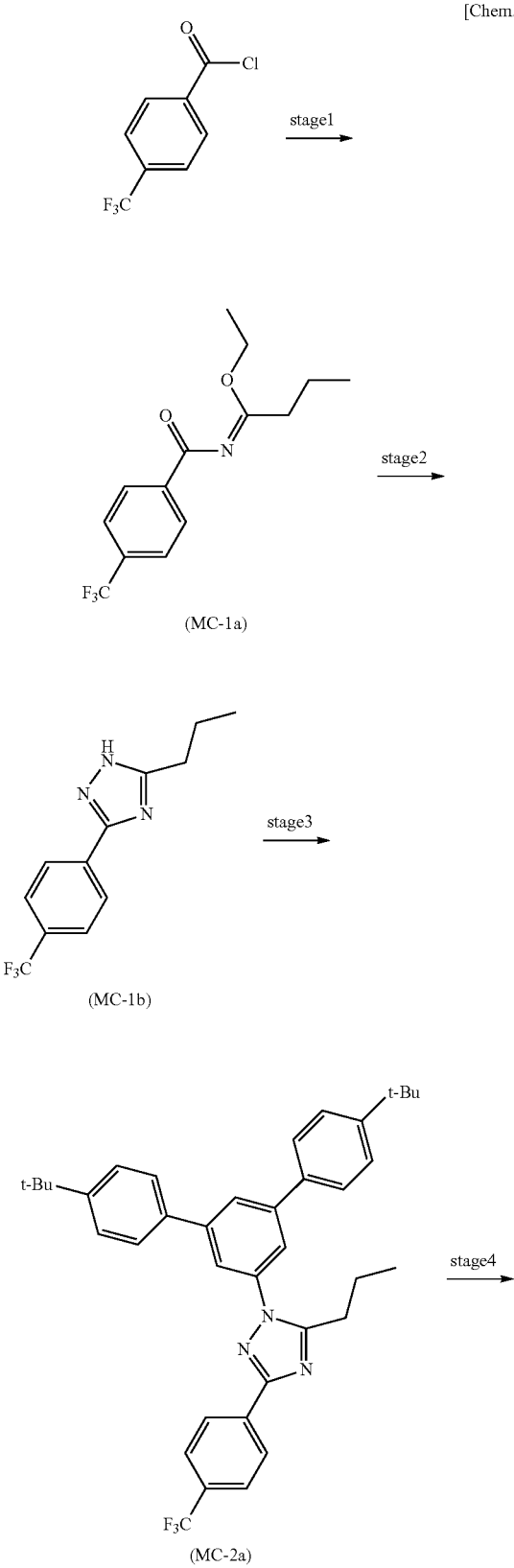

[Chem. 31]

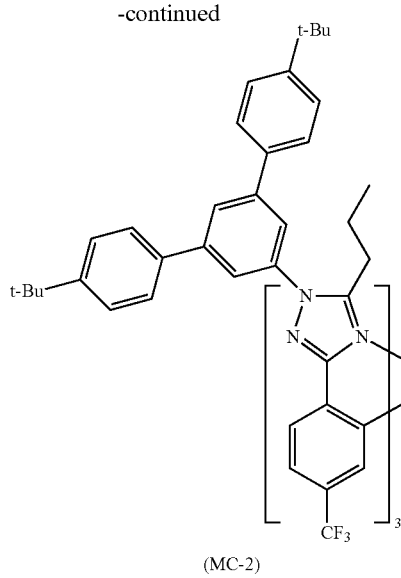

(MC-2)

<Stage 1>
A compound (MC-1a) was obtained by the method described in stage 1 in the synthesis of the compound (MC-1).

<Stage 2>
A compound (MC-1b) was obtained by the method described in stage 2 in the synthesis of the compound (MC-1).

<Stage 3>
Twenty (20) grams (80 mmol) of the compound (MC-1b), 41 g (107 mmol) of 3,5-di(4-tert-butylphenyl)phenylboronic acid, 24.4 g (135 mmol) of copper (II) acetate, and 50 g of Molecular Sieves 3A (manufactured by Wako Pure Chemical Industries, Ltd.) were weighed and thereto, 1 L of dichloromethane and 50 mL of pyridine were added, followed by stirring the resultant at room temperature for 60 hours. After 60 hours, the suspension was subjected to suction filtration and washed with 500 mL of dichloromethane. The filtrate was concentrated and then dissolved in dichloromethane, followed by washing the resultant with 300 mL of water for several times. The oil layer was dried and then passed through a silica gel column to be separated and purified using a mixed solvent of dichloroethane-hexane. The obtained compound was recrystallized from a mixed solvent of methanol-tetrahydrofuran, thus obtaining 15 g (25 mmol) of a compound (MC-2a) as a light yellow solid in a yield of 31%. The result of the $^1$H-NMR analysis is shown below.

$^1$H-NMR (400 MHz/(CD$_3$)$_2$CO): δ (ppm) 8.24 (d, 2H), 7.94 (t, 1H), 7.72 (d, 2H), 7.70 (d, 2H), 7.65 (d, 4H), 7.44 (dt, 4H), 2.85 (t, 2H), 1.76 (td, 2H), 1.24 (s, 18H), 0.87 (t, 3H).

<Stage 4>
Two hundred ninety (290) milligrams (0.82 mmol) of iridium chloride and 1.23 g (2.1 mmol) of the compound (MC-2a) were weighed and thereto, 6 mL of water and 18 mL of 2-butoxyethanol were added. The inside of the reaction system was placed under an argon atmosphere and the resultant was heated and refluxed for 15 hours. After cooling down, the reaction liquid was concentrated under reduced pressure. The residue was dissolved in dichloromethane and was washed. The oil layer was concentrated, dried, and recrystallized from a mixed solvent of dichloromethane-hexane to obtain 1.2 g of a powdery yellow solid. Then, 1.2 g of the powdery yellow solid and 2.44 g (4.1 mmol) of the compound (MC-2a) were weighed and thereto, 210 mg (0.82 mmol) of silver trifluoromethanesulfonate was added under an argon atmosphere. Thereto, 6 mL of diethylene glycol dimethyl ester was poured. Under an argon atmosphere, the resultant was heated and refluxed for 24 hours and was left to be cooled down. To the reaction mixture, 20 mL of dichloromethane was poured and the resultant was subjected to suction filtration. The filtrate was concentrated and dried. The resultant crude product was passed through a silica gel column to be separated and purified using a mixed solvent of dichloromethane-hexane. The eluate was concentrated and the resultant was recrystallized from a mixed solvent of methanol-tetrahydrofuran and then recrystallized from a mixed solvent of dichloromethane-hexane, thus obtaining 680 mg (0.34 mmol) of a compound (MC-2) [fac-tris(1-(3,5-di(4-tert-butylphenyl)phenyl)-3-(4-trifluoromethylphenyl)-5-propyl-1H-[1,2,4]-triazolato-N,C2') iridium (III)] as a light yellow crystal in a yield of 42%. The identification of the product was performed using the $^1$H-NMR analysis and the X-ray crystal structure analysis. The result of the $^1$H-NMR analysis is shown below.

$^1$H-NMR (400 MHz/CDCl$_3$): δ (ppm) 7.90 (t, 3H), 7.83 (d, 3H), 7.59 (d, 6H), 7.55 (dd, 12H), 7.48 (dd, 12H), 7.19 (dd, 3H), 6.86 (d, 3H), 2.60 (dt, 3H), 2.44 (dt, 3H), 1.35 (s, 54H), 1.29 (m, 3H), 1.08 (m, 3H), 0.64 (t, 9H).

Comparative Example 1: Synthesis of Compound (MC-3)

[Chem. 32]

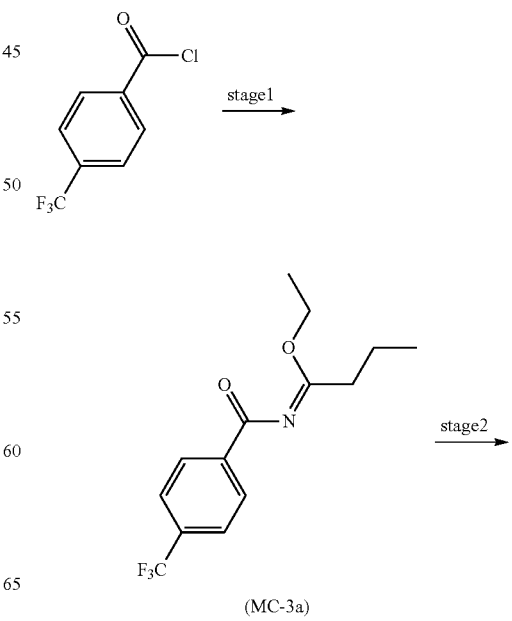

(MC-3a)

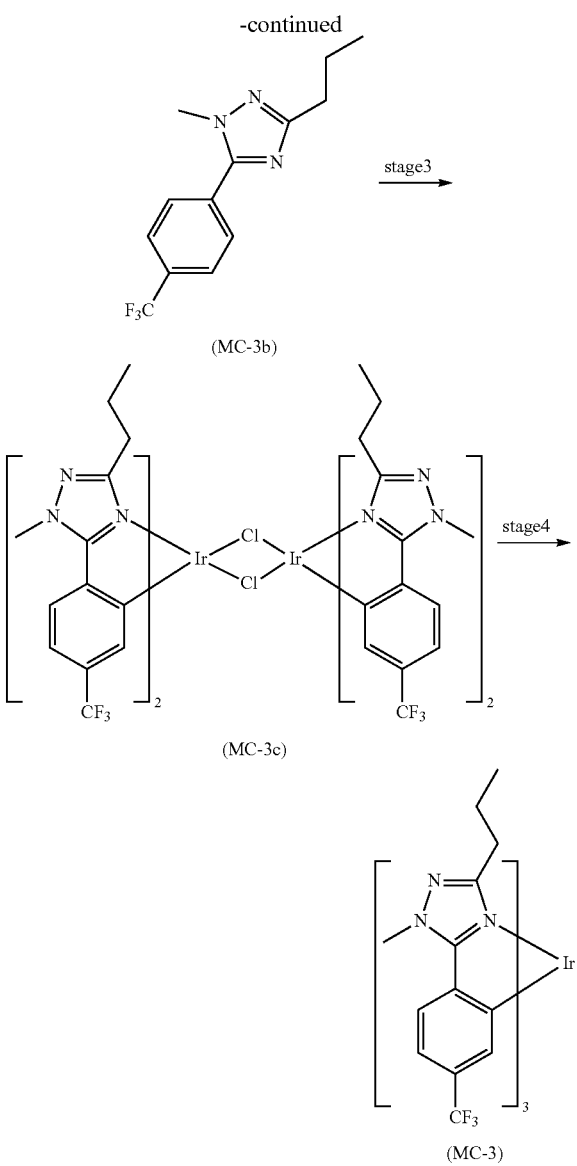

(MC-3b)

(MC-3c)

(MC-3)

<Stage 1>

Six point two (6.2) grams (30 mmol) of 4-trifluoromethylbenzoyl chloride and 4.5 g (30 mmol) of ethyl butyrimidate hydrochloride were weighed and dissolved in 300 mL of chloroform, and the resultant was placed under a nitrogen atmosphere. Thereafter, 25 mL of a chloroform solution of 8.4 mL (60 mmol) of triethylamine was added dropwise thereto and the resultant was stirred at room temperature under a nitrogen atmosphere. After 15 hours, chloroform as the solvent was concentrated and the concentrate was suspended in 200 mL of water, followed by extracting the resultant solution with dichloromethane. The resultant solution was concentrated under reduced pressure, thus obtaining 8.0 g (28 mmol) of a compound (MC-3a) as a light yellow liquid.

<Stage 2>

Into 200 mL of chloroform, 8.0 g (28 mmol) of the compound (MC-3a) was dissolved and the resultant was placed under a nitrogen atmosphere. Thereto, 25 mL of a chloroform solution containing 1.6 g (35 mmol) of methylhydrazine and 0.7 mL of water was added dropwise under a nitrogen atmosphere at room temperature. After the dropwise addition, the resultant was stirred at room temperature under a nitrogen atmosphere for 15 hours and 100 mL of water was added therein to quench the reaction. Then, the reaction liquid was transferred into a separating funnel and was washed with water, followed by recovering and concentrating an oil layer. The resultant crude product was passed through a silica gel column to be purified using a mixed solvent of dichloromethane-ethyl acetate. The eluate was concentrated, thus obtaining 4.8 g of a compound (MC-3b) as a colorless liquid in a yield of 64%. The result of the $^1$H-NMR analysis is shown below.

$^1$H-NMR (400 MHz/CDCl$_3$): δ (ppm) 7.80 (m, 4H), 3.97 (s, 3H), 2.74 (t, 2H), 1.83 (m, 2H), 1.02 (t, 3H).

<Stage 3>

Four hundred seventy (470) milligrams (1.3 mmol) of iridium chloride and 1 g (3.7 mmol) of the compound (MC-3b) were weighed and thereto, 18 mL of 2-ethyloxyethanol and 6 mL of water were added. The resultant was placed under a nitrogen atmosphere and was heated and refluxed for 12 hours. After cooling down, the reaction liquid was concentrated. To the residue, water and dichloromethane were added to wash the oil layer with water. The oil layer was recovered and was concentrated and dried, thus obtaining 900 mg of a compound (MC-3c) as a yellow oily substance.

<Stage 4>

Seven hundred sixty (760) milligrams (0.5 mmol) of the compound (MC-3c) and 1.35 g (5.0 mmol) of the compound (MC-3b) were weighed and thereto, 260 mg of silver trifluoromethanesulfonate was added, followed by replacing the inside of the reaction system with argon. The resultant was heated for reaction at 165° C. for 15 hours and was left to be cooled down, and thereto, 15 mL of dichloromethane was poured. The suspension was subjected to suction filtration and then passed through a silica gel column to be separated and purified using a mixed solvent of dichloromethane-ethyl acetate, thus obtaining 900 mg of a compound (MC-3) [fac-tris(1-methyl-3-propyl-5-(4-trifluoromethylphenyl)-1H-[1,2,4]-triazolato-N,C2') iridium (III)] as yellow powder in a yield of 90%. The result of the $^1$H-NMR analysis is shown below.

$^1$H-NMR (400 MHz/CDCl$_3$): δ (ppm) 7.58 (d, 3H), 7.18 (d, 3H), 6.75 (s, 3H), 4.23 (s, 9H), 2.16-2.27 (m, 3H), 1.81-1.90 (m, 3H), 1.45-1.29 (m, 3H), 1.22-1.07 (m, 3H), 0.70 (t, 9H)

Comparative Example 2: Synthesis of Compound (MC-4)

[Chem. 33]

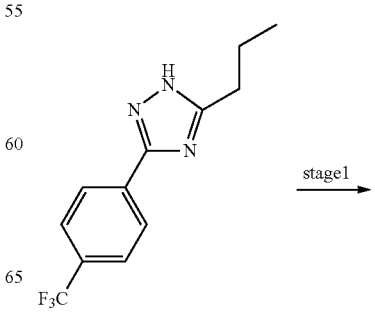

stage1

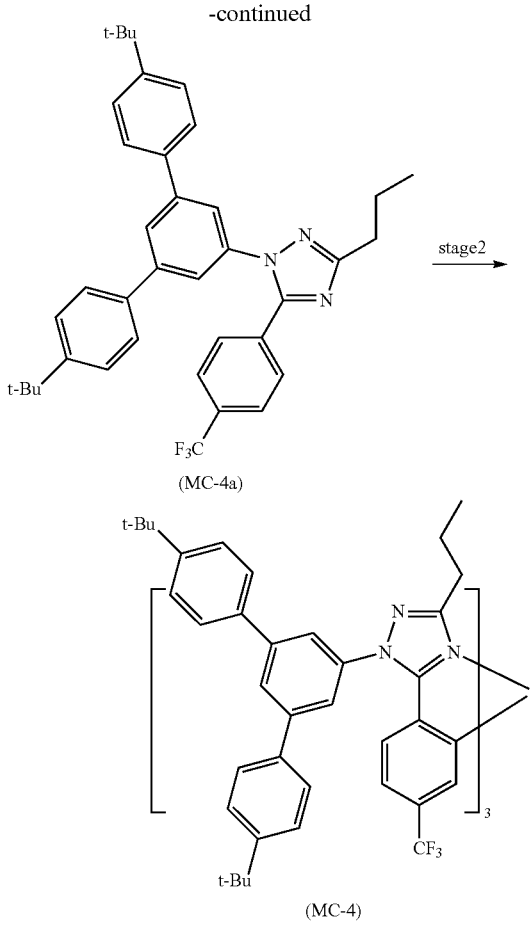

(MC-4a)

(MC-4)

<Stage 1>
The compound (MC-4a) generated according to the reaction described in stage 3 in the synthesis of the compound (MC-2) was separated by silica gel column purification. The resultant eluate was concentrated and was recrystallized from a mixed solvent of methanol-tetrahydrofuran, thus obtaining 2.2 g (3.7 mmol) of the compound (MC-4a) as yellow white powder. The result of the $^1$H-NMR analysis is shown below.

$^1$H-NMR (400 MHz/(CD$_3$)$_2$CO): δ (ppm) 7.99 (t, 1H), 7.86 (d, 2H), 7.79 (d, 2H), 7.62 (d, 2H), 7.60 (ddd, 4H), 7.50 (ddd, 4H), 2.78 (t, 2H), 1.87 (td, 2H), 1.34 (s, 18H), 1.06 (t, 3H).

<Stage 2>
One hundred forty (140) milligrams (0.4 mmol) of iridium chloride and 600 mg (1.0 mmol) of the compound (MC-4a) were weighed and thereto, 3 mL of water and 9 mL of 2-butoxyethanol were added, followed by placing the inside of the reaction system under an argon atmosphere. The resultant was heated and refluxed for 15 hours. After cooling down, the reaction mixture was concentrated under reduced pressure. The resultant residue was dissolved in dichloromethane and was washed. The oil layer was concentrated, dried, and recrystallized from a mixed solvent of dichloromethane-hexane to obtain 680 mg of a powdery yellow solid. Then, 680 mg of the powdery yellow solid and 1.23 g (2.1 mmol) of the compound (MC-4a) were weighed and thereto, 120 mg (0.47 mmol) of silver trifluoromethanesulfonate was added under an argon atmosphere. Thereto, 3 mL of diethylene glycol dimethyl ester was poured. Thereafter, the resultant was heated and refluxed under an argon atmosphere for 24 hours. The reaction mixture was left to be cooled down and thereto, 20 mL of dichloromethane was poured, followed by subjecting the resultant to suction filtration. The filtrate was concentrated and dried. The resultant crude product was passed through a silica gel column to be separated and purified using a mixed solvent of dichloromethane-hexane. The eluate was concentrated and the resultant was recrystallized from a mixed solvent of methanol-tetrahydrofuran and then recrystallized from a mixed solvent of dichloromethane-hexane, thus obtaining 710 mg (0.36 mmol) of a compound (MC-4) [fac-tris(1-(3,5-di(4-tert-butylphenyl)phenyl)-3-propyl-5-(4-trifluoromethylphenyl)-1H-[1,2,4]-triazolato-N,C2')iridium (III)] as a light yellow crystal in a yield of 90%. The result of the $^1$H-NMR analysis is shown below.

$^1$H-NMR (400 MHz/CDCl$_3$): δ (ppm) 8.04 (dd, 3H), 7.65 (d, 6H), 7.61 (d, 12H), 7.50 (d, 12H), 7.07 (d, 3H), 6.94 (d, 3H), 6.84 (s, 3H), 2.49 (hep, 3H), 2.27 (hep, 3H), 1.69-1.56 (m, 3H), 1.52-1.38 (m, 3H), 1.37 (s, 54H), 0.88 (t, 9H).

Example 3: Synthesis of Compound (MC-5)

[Chem. 34]

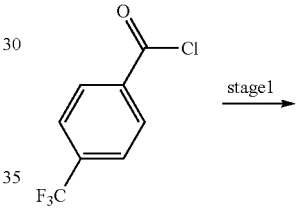

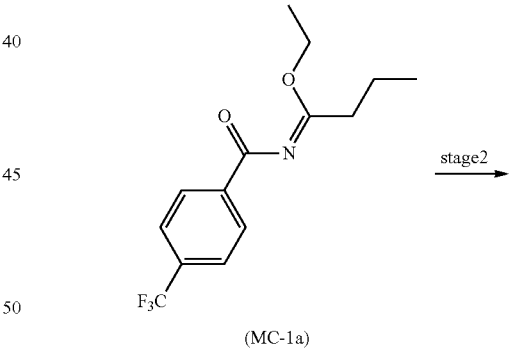

(MC-1a)

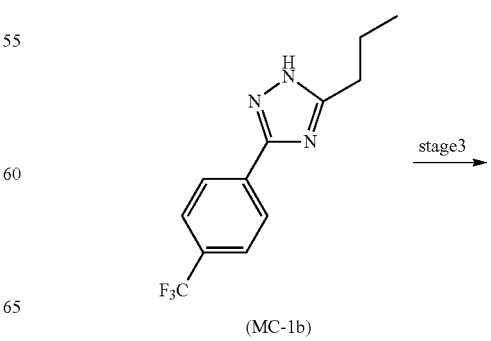

(MC-1b)

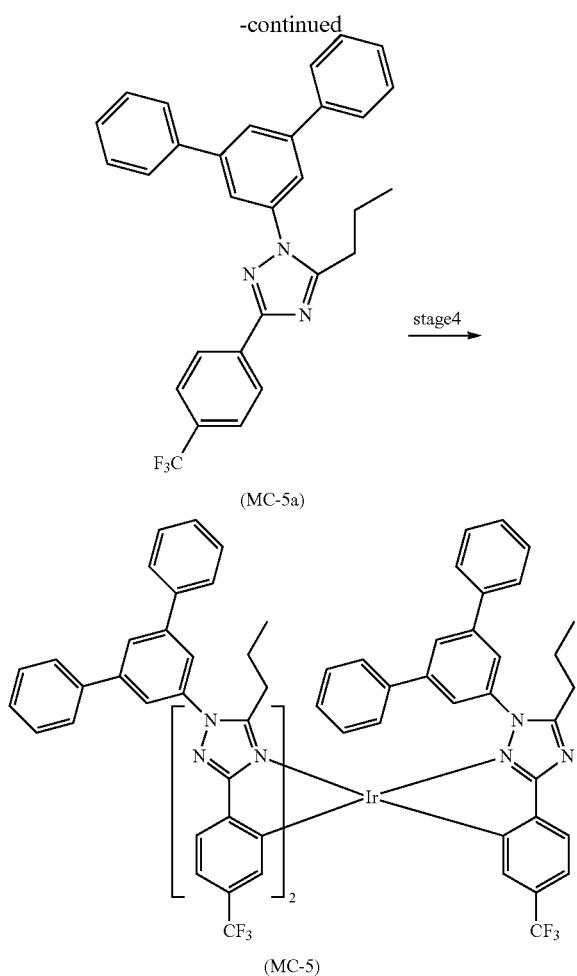

(MC-5a)

(MC-5)

<Stage 1>

Six point two (6.2) grams (30 mmol) of 4-trifluoromethylbenzoyl chloride and 4.5 g (30 mmol) of ethyl butyrimidate hydrochloride were weighed and dissolved in 300 mL of chloroform, and the resultant was placed under a nitrogen atmosphere. Thereafter, 25 mL of a chloroform solution of 8.4 mL (60 mmol) of triethylamine was added dropwise thereto and the resultant was stirred at room temperature under a nitrogen atmosphere. After 15 hours, chloroform as a solvent was concentrated and the concentrate was suspended in 200 mL of water, followed by extracting the resultant with dichloromethane. The resultant solution was concentrated under reduced pressure, thus obtaining 8.0 g (28 mmol) of a compound (MC-1a) as a light yellow liquid.

<Stage 2>

Into 60 mL of chloroform, 3.0 g (10 mmol) of the compound (MC-1a) was dissolved and the resultant was placed under a nitrogen atmosphere. Thereto, 0.55 mL (11 mmol) of hydrazine hydrate was added dropwise at room temperature under a nitrogen atmosphere. After the dropwise addition, the resultant was stirred at room temperature under a nitrogen atmosphere for 17 hours and then 50 mL of water was added therein to quench the reaction. Then, the reaction liquid was transferred into a separating funnel and was washed with water, followed by recovering and concentrating an oil layer. The obtained crude product was recrystallized from a mixed solvent of toluene-hexane, thus obtaining 2.1 g of a compound (MC-1b) as a white solid in a yield of 82%. The result of the $^1$H-NMR analysis is shown below.

$^1$H-NMR (400 MHz/CDCl$_3$): δ (ppm) 8.15 (d, 2H), 7.66 (d, 2H), 2.78 (t, 2H), 1.82 (hex, 2H), 0.94 (t, 3H).

<Stage 3>

Seven hundred twenty (720) milligrams (2.8 mmol) of the compound (MC-1b), 1.6 g (5.8 mmol) of 3,5-diphenylphenylboronic acid, 810 mg (4.5 mmol) of copper (II) acetate, and 10 g of Molecular Sieves 3A (manufactured by Wako Pure Chemical Industries, Ltd.) were weighed and thereto, 20 mL of dichloromethane and 10 mL of pyridine were added. The resultant was stirred at room temperature for 48 hours. Thereto, 50 mL of dichloromethane was poured, and the suspension was subjected to suction filtration. The filtrate was concentrated, and the concentrate was dissolved in dichloromethane and washed with 100 mL of water. The oil layer was dried and then passed through a silica gel column to be separated and purified using dichloromethane, thus obtaining 750 mg of a compound (MC-5a) as a white solid in a yield of 55%. The result of the $^1$H-NMR analysis is shown below.

$^1$H-NMR (400 MHz/CDCl$_3$): δ (ppm) 8.30 (d, 2H), 7.92 (t, 1H), 7.71-7.66 (m, 8H), 7.49 (t, 4H), 7.41 (t, 2H), 2.91 (t, 3H), 1.90 (hex, 2H), 1.01 (t, 3H).

<Stage 4>

One hundred (100) milligrams (0.28 mmol) of iridium chloride and 280 mg (0.58 mmol) of the compound (MC-5a) were weighed and thereto, 12 mL of 2-ethyloxyethanol and 4 mL of water were added. The resultant mixture was placed under a nitrogen atmosphere and was heated and refluxed for 12 hours. After cooling down, the reaction liquid was concentrated under reduced pressure. The resultant crude product was dissolved in dichloromethane and washed, followed by concentrating and drying an organic layer to obtain 240 mg of a powdery yellow solid. Then, 180 mg of the powdery yellow solid and 270 mg (0.56 mmol) of the compound (MC-5a) were weighed and thereto, 42 mg (0.16 mmol) of silver trifluoromethanesulfonate was added under an argon atmosphere. Thereafter, the resultant was heated for reaction at 166° C. in an argon atmosphere for 61 hours. After cooling down, 15 mL of dichloromethane was added thereto and the resultant was subjected to suction filtration. To the filtrate, water and dichloromethane were added to wash an oil layer. The oil layer was dried and then passed through a silica gel column to be separated and purified using a mixed solvent of dichloromethane-ethyl acetate. The eluate was concentrated and was recrystallized from a mixed solvent of dichloromethane-hexane, thus obtaining 120 mg of a compound (MC-5) [fac-tris(1-(3,5-diphenylphenyl)-3-(4-trifluoromethylphenyl)-5-propyl-1H-[1,2,4]-triazolato-N,C2') iridium (III)] as a yellow needle-like crystal of light yellow in a yield of 65%. The identification of the product was performed using the $^1$H-NMR analysis and the X-ray crystal structure analysis. The result of the $^1$H-NMR analysis is shown below.

$^1$H-NMR (400 MHz/CDCl$_3$): δ (ppm) 7.93 (d, 1H), 7.92 (s, 1H), 7.84 (t, 1H), 7.75 (d, 1H), 7.65-7.61 (m, 7H), 7.56-7.42 (m, 20H), 7.39-7.31 (m, 4H), 7.27-7.25 (m, 4H), 7.20-7.19 (m, 4H), 7.12 (dd, 1H), 6.80 (s, 2H), 6.71 (t, 1H), 6.62 (d, 1H), 2.80-2.72 (m, 1H), 2.64-2.49 (m, 3H), 2.12-1.95 (m, 2H), 1.76 (hex, 2H), 1.14-1.02 (m, 2H), 0.89 (m, 5H), 0.68 (t, 3H), 0.41 (t, 3H).

Test Example 1: Measurement of Emission Spectrum of Compound (MC-1)

The compound (MC-1) was dissolved in THF (manufactured by Kanto Chemical Co., Inc.: grade for spectroscopy) so as to have a concentration of 1×10$^{-6}$ mol/L and argon gas was passed through the solution. Then, an emission spectrum at room temperature (excitation wavelength: 350 nm) was measured using an absolute PL quantum yield measurement system (C9920) manufactured by Hamamatsu Photonics K.K. The result is shown in Table 1. In Table 1, $\lambda_{RT}$ represents a peak wavelength of the emission spectrum at room temperature in THF (under an argon atmosphere) and CIE (x, y)@RT represents luminescent chromaticity at room temperature in THF (under an argon atmosphere).

The compound (MC-1) was dissolved in 2-MeTHF (manufactured by Sigma-Aldrich Co. LLC.: anhydrous, inhibitor-free) so as to have a concentration of 1×10⁻⁶ mol/L. Then, an emission spectrum at 77K (excitation wavelength: 350 nm) was measured using an absolute PL quantum yield measurement system (C9920) manufactured by Hamamatsu Photonics K.K. The result is shown in Table 1. In Table 1, $\lambda_{77}$ represents a peak wavelength of the emission spectrum at 77K in 2-MeTHF and CIE (x, y)@77K represents luminescent chromaticity at 77K in 2-MeTHF.

Test Example 2: Measurement of Emission Spectrum of Compound (MC-2)

The emission spectra of the compound (MC-2) at room temperature and at 77K were measured in the same manner as in Test Example 1, except that the compound (MC-2) was used instead of the compound (MC-1) in Test Example 1. The results are shown in Table 1.

Test Comparative Example 1: Measurement of Emission Spectrum of Compound (MC-3)

The emission spectra of the compound (MC-3) at room temperature and at 77K were measured in the same manner as in Test Example 1, except that the compound (MC-3) was used instead of the compound (MC-1) in Test Example 1. The results are shown in Table 1.

Test Comparative Example 2: Measurement of Emission Spectrum of Compound (MC-4)

The emission spectra of the compound (MC-4) at room temperature and at 77K were measured in the same manner as in Test Example 1, except that the compound (MC-4) was used instead of the compound (MC-1) in Test Example 1. The results are shown in Table 1.

TABLE 1

|  | Compound | $\lambda_{RT}$ | CIE (x, y)@RT | $\lambda_{77}$ | CIE (x, y)@77 K |
|---|---|---|---|---|---|
| Test Example 1 | (MC-1) | 444 nm | (0.16, 0.17) | 445 nm | (0.16, 0.17) |
| Test Example 2 | (MC-2) | 448 nm | (0.16, 0.18) | 447 nm | (0.15, 0.16) |
| Test Comparative Example 1 | (MC-3) | 468 nm | (0.17, 0.32) | 462 nm | (0.16, 0.25) |
| Test Comparative Example 2 | (MC-4) | 495 nm | (0.25, 0.53) | 477 nm | (0.18, 0.41) |

The results in Table 1 have revealed that the metal complex of the present invention exhibits blue light emission of high color purity and has a color purity of small temperature dependence in a blue region.

The invention claimed is:
1. A metal complex represented by Formula (1a):

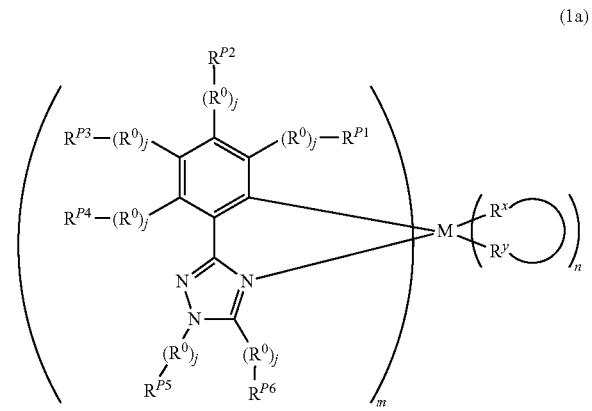

(1a)

wherein
M is a metal atom selected from the group consisting of a ruthenium atom, a rhodium atom, a palladium atom, an osmium atom, an iridium atom and a platinum atom;
each $R^0$ is independently a divalent linking group selected from the group consisting of a group represented by Formula (L-1), a group represented by Formula (L-2) and a group represented by Formula (L-3):

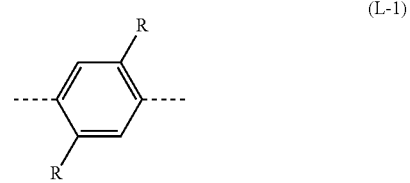

(L-1)

(L-2)

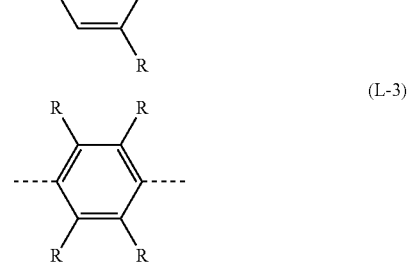

(L-3)

wherein each R independently represents an alkyl group;
each j independently represents 0 or 1;
$R^{P1}$, $R^{P2}$, $R^{P3}$ and $R^{P4}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group;

$R^{P5}$ represents a halogen atom, an alkyl group, an alkyloxy group, an aryl group or a monovalent heterocyclic group;

$R^{P6}$ represents an alkyl group, an aryl group or a monovalent heterocyclic group;

wherein at least one of $R^{P1}$, $R^{P2}$, $R^{P3}$, $R^{P4}$, $R^{P5}$ and $R^{P6}$ is a dendron, the dendron is a phenyl group having two or more substituents, and each of the two or more substituents is a phenyl group which is substituted only by one alkyl group;

$R^{P1}$, and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure;

m is an integer of from 1 to 3, n is an integer of from 0 to 2, and m+n is 2 or 3; and the portion represented by Formula (2):

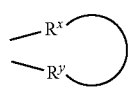

(2)

represents a bidentate ligand;

wherein $R^x$ and $R^y$ are an atom bonding to the metal atom M, and each independently represent a carbon atom, an oxygen atom or a nitrogen atom.

2. The metal complex according to claim 1, wherein n is 0.

3. A metal complex represented by Formula (1b):

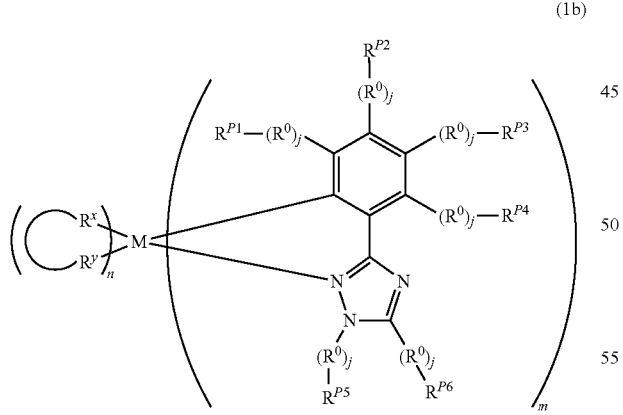

(1b)

wherein

M is a metal atom selected from the group consisting of a ruthenium atom, a rhodium atom, a palladium atom, an osmium atom, an iridium atom and a platinum atom;

each $R^0$ is independently a divalent linking group selected from the group consisting of a group represented by Formula (L-1), a group represented by Formula (L-2) and a group represented by Formula (L-3):

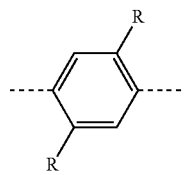

(L-1)

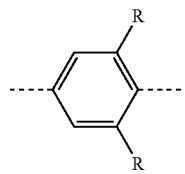

(L-2)

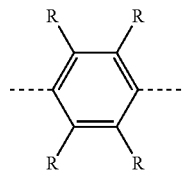

(L-3)

wherein each R independently represents an alkyl group;

each j independently represents 0 or 1;

$R^{P1}$, $R^{P2}$, $R^{P3}$ and $R^{P4}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group;

$R^{P5}$ represents a halogen atom, an alkyl group, an alkyloxy group, an aryl group or a monovalent heterocyclic group;

$R^{P6}$ represents an alkyl group, an aryl group or a monovalent heterocyclic group;

wherein at least one of $R^{P1}$, $R^{P2}$, $R^{P3}$, $R^{P4}$, $R^{P5}$ and $R^{P6}$ is a dendron, the dendron is a phenyl group having two or more substituents, and each of the two or more substituents is an unsubstituted phenyl group or a phenyl group which is substituted only by one alkyl group;

$R^{P1}$ and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure;

m is an integer of from 1 to 3, n is an integer of from 0 to 2, and m+n is 2 or 3; and the portion represented by Formula (2):

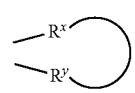

(2)

represents a bidentate ligand;
wherein $R^x$ and $R^y$ are an atom bonding to the metal atom M, and each independently represent a carbon atom, an oxygen atom or a nitrogen atom.

4. The metal complex according to claim 3, wherein n is 0.

5. A metal complex represented by Formula (1c):

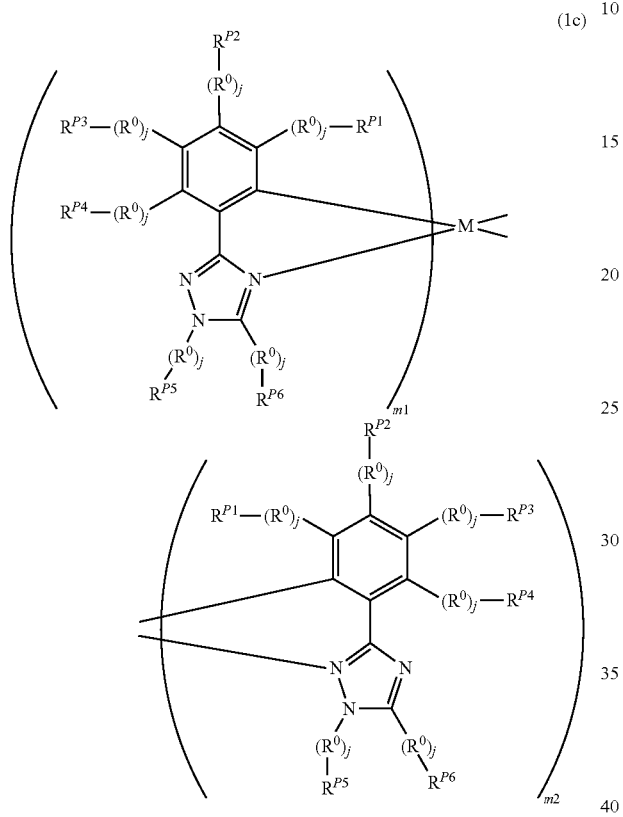

(1c)

wherein
M is a metal atom selected from the group consisting of a ruthenium atom, a rhodium atom, a palladium atom, an osmium atom, an iridium atom and a platinum atom;
each $R^0$ is independently a divalent linking group selected from the group consisting of a group represented by Formula (L-1), a group represented by Formula (L-2) and a group represented by Formula (L-3):

(L-1)

(L-2)

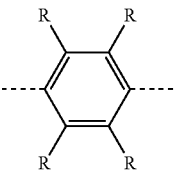

(L-3)

wherein each R independently represents an alkyl group;
each j independently represents 0 or 1;
$R^{P1}$, $R^{P2}$, $R^{P3}$ and $R^{P4}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, and $R^{P1}$, $R^{P2}$, $R^{P4}$ and $R^{P6}$, which are plurally present, may be the same or different;
$R^{P5}$ represents a halogen atom, an alkyl group, an alkyloxy group, an aryl group or a monovalent heterocyclic group, and a plurality of $R^{P5}$ may be the same or different;
$R^{P6}$ represents an alkyl group, an aryl group or a monovalent heterocyclic group;
wherein at least one of $R^{P1}$, $R^{P2}$, $R^{P3}$, $R^{P4}$, $R^{P5}$ and $R^{P6}$ is a dendron, the dendron is a phenyl group having two or more substituents, and each of the two or more substituents is an unsubstituted phenyl group or a phenyl group which is substituted only by one alkyl group;
$R^{P1}$ and $R^{P2}$ may be connected to form a ring structure, $R^{P2}$ and $R^{P3}$ may be connected to form a ring structure, $R^{P3}$ and $R^{P4}$ may be connected to form a ring structure, and $R^{P5}$ and $R^{P6}$ may be connected to form a ring structure; and
m1 and m2 are each independently 1 or 2, and m1+m2 is 2 or 3.

6. The metal complex according to claim 1, wherein M is a platinum atom or an iridium atom.

7. The metal complex according to claim 1, wherein a peak wavelength of an emission spectrum of a dilute solution of the metal complex is from 430 nm to 630 nm, wherein the dilute solution contains the metal complex in an organic solvent at a concentration of from $1\times10^{-6}$ to $1\times10^{-7}$ mol/L, and wherein the emission spectrum is a PL spectrum measured at room temperature.

8. A composition comprising:
(a) the metal complex according to claim 1; and
(b) a charge transport compound.

9. The composition according to claim 8, wherein the charge transport compound is a polymer compound.

10. A film comprising the composition according to claim 8.

11. A light-emitting device including:
(a) electrodes composed of an anode and a cathode; and
(b) a layer comprising the composition according to claim 8, which is provided between the electrodes.

12. A planar light source including the light-emitting device according to claim 11.

13. An illumination apparatus including the light-emitting device according to claim 11.

14. A composition comprising:
(a) the metal complex according to claim 1; and
(b) a solvent or dispersion medium.

15. A film comprising:
(a) the metal complex according to claim 1.

16. A light-emitting device including:
(a) electrodes composed of an anode and a cathode; and
(b) a layer comprising the metal complex according to claim 1, which is provided between the electrodes.

17. A planar light source including the light-emitting device according to claim 16.

18. An illumination apparatus including the light-emitting device according to claim 16.

19. The metal complex according to claim 1, wherein $R^{P3}$ and $R^{P5}$ are the dendron.

20. The metal complex according to claim 3, wherein $R^{P3}$ and $R^{P5}$ are the dendron.

21. The metal complex according to claim 5, wherein $R^{P3}$ and $R^{P5}$ are the dendron.

22. The metal complex according to claim 1, wherein at least one of $R^{P1}$, $R^{P2}$, $R^{P3}$, and $R^{P4}$ is an alkyl group, an aryl group, or a monovalent heterocyclic group.

23. The metal complex according to claim 1, wherein $R^{P3}$ is the dendron.

* * * * *